US012649917B2

(12) United States Patent
Beisel et al.

(10) Patent No.: US 12,649,917 B2
(45) Date of Patent: Jun. 9, 2026

(54) COMPOSITIONS, METHODS, AND SYSTEMS FOR GENOME EDITING TECHNOLOGY

(71) Applicant: North Carolina State University, Raleigh, NC (US)

(72) Inventors: Chase Lawrence Beisel, Raleigh, NC (US); Scott Collins, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 762 days.

(21) Appl. No.: 17/905,934

(22) PCT Filed: Mar. 9, 2021

(86) PCT No.: PCT/US2021/021493
§ 371 (c)(1),
(2) Date: Sep. 8, 2022

(87) PCT Pub. No.: WO2021/183504
PCT Pub. Date: Sep. 16, 2021

(65) Prior Publication Data
US 2023/0040261 A1 Feb. 9, 2023

Related U.S. Application Data

(60) Provisional application No. 62/988,262, filed on Mar. 11, 2020.

(51) Int. Cl.
*C12N 15/10* (2006.01)
*C12N 9/22* (2006.01)
*C12N 15/90* (2006.01)

(52) U.S. Cl.
CPC .............. *C12N 15/102* (2013.01); *C12N 9/22* (2013.01); *C12N 15/907* (2013.01);
(Continued)

(58) Field of Classification Search
CPC ........ C12Y 305/04005; C07K 2319/00; C12N 2310/20
See application file for complete search history.

(56) References Cited

U.S. PATENT DOCUMENTS

2017/0321210 A1 11/2017 Nishida et al.
2019/0249182 A1 8/2019 Beetham et al.
(Continued)

FOREIGN PATENT DOCUMENTS

WO WO 2018/071868 4/2018
WO WO 2018/165629 9/2018
(Continued)

OTHER PUBLICATIONS

Hidalgo-Cantabrana, Claudio, and Rodolphe Barrangou. "Characterization and Applications of Type I CRISPR-Cas Systems." Biochemical Society Transactions, vol. 48, No. 1, Jan. 10, 2020, pp. 15-23, https://doi.org/10.1042/bst20190119. Accessed Sep. 10, 2020. (Year: 2020).*
(Continued)

*Primary Examiner* — Kimberly Chong
*Assistant Examiner* — Africa M Mcleod
(74) *Attorney, Agent, or Firm* — Casimir Jones, S.C.; Peter J. Schlueter

(57) ABSTRACT

The present disclosure provides compositions, methods, and systems related to genome editing technology. In particular, the present disclosure provides a novel CRISPR-based genome editing technology that involves the generation of abasic sites to facilitate genetic recombination, without the need for breaks in the DNA. The compositions, methods, and systems described herein address many of the drawbacks of currently available approaches, including off-target effects and cellular toxicity.

38 Claims, 17 Drawing Sheets

Specification includes a Sequence Listing.

Targeting

Recombination

Successful editing
Results in active enzyme

(52) U.S. Cl.
CPC .. *C12Y 305/04005* (2013.01); *C07K 2319/00*
(2013.01); *C12N 2310/20* (2017.05)

(56) References Cited

U.S. PATENT DOCUMENTS

| | | |
|---|---|---|
| 2020/0010856 A1 | 1/2020 | Nishida et al. |
| 2020/0063127 A1 | 2/2020 | Lu et al. |

FOREIGN PATENT DOCUMENTS

| | | | | |
|---|---|---|---|---|
| WO | WO 2018/176009 | 9/2018 | | |
| WO | WO 2019/139645 | 7/2019 | | |
| WO | WO 2019/161251 | 8/2019 | | |
| WO | WO 2019/217942 | 11/2019 | | |
| WO | WO-2019241452 A1 * | 12/2019 | ..... | C12Y 301/21004 |

OTHER PUBLICATIONS

Pinilla-Redondo, Rafael, et al. "Type IV CRISPR-Cas Systems Are Highly Diverse and Involved in Competition between Plasmids." Nucleic Acids Research, vol. 48, No. 4, Dec. 27, 2019, pp. 2000-2012, https://doi.org/10.1093/nar/gkz1197. (Year: 2019).*

Bae, Sang-Jeong, et al. "Multiplex Gene Disruption by Targeted Base Editing of Yarrowia Lipolytica Genome Using Cytidine Deaminase Combined with the CRISPR/Cas9 System." Biotechnology Journal, vol. 15, Oct. 28, 2019, p. 1900238, https://doi.org/10.1002/biot.201900238. (Year: 2019).*

Arazoe, Takayuki, et al. "Targeted Nucleotide Editing Technologies for Microbial Metabolic Engineering." Biotechnology Journal, vol. 13, No. 9, Jun. 19, 2018, p. 1700596, https://doi.org/10.1002/biot.201700596. Accessed Feb. 23, 2022. (Year: 2018).*

EMBL-EBI. "What Are Protein Domains? | Protein Classification." EMBL-EBI, 2023, www.ebi.ac.uk/training/online/courses/protein-classification-intro-ebi-resources/protein-classification/what-are-protein-domains/. (Year: 2023).*

International Search Report and Written Opinion for PCT/US2021/021493. Mailed Jun. 15, 2021. 10 pages.

Anzalone et al., Genome editing with CRISPR-Cas nucleases, base editors, transposases and prime editors. Nat Biotechnol. Jul. 2020;38(7):824-844.

Anzalone et al., Search-and-replace genome editing without double-strand breaks or donor DNA. Nature. Dec. 2019;576(7785):149-157.

Bassalo et al., Rapid and Efficient One-Step Metabolic Pathway Integration in *E. coli*. ACS Synth Biol. Jul. 15, 2016;5(7):561-8.

Chrabaszcz et al., DNA lesions proximity modulates damage tolerance pathways in *Escherichia coli*. Nucleic Acids Res. May 4, 2018;46(8):4004-4012.

De Paepe et al., Temperate phages acquire DNA from defective prophages by relaxed homologous recombination: the role of Rad52-like recombinases. PLOS Genet. Mar. 6, 2014;10(3):e1004181. 15 pages.

Gaudelli et al., Programmable base editing of A•T to G•C in genomic DNA without DNA cleavage. Nature. Nov. 23, 2017;551(7681):464-471.

Gehrke et al., An APOBEC3A-Cas9 base editor with minimized bystander and off-target activities. Nat Biotechnol. Nov. 2018;36(10):977-982.

Haapaniemi et al., CRISPR-Cas9 genome editing induces a p53-mediated DNA damage response. Nat Med. Jul. 2018;24(7):927-930.

Ihry et al., p53 inhibits CRISPR-Cas9 engineering in human pluripotent stem cells. Nat Med. Jul. 2018;24(7):939-946.

Jinek et al., A programmable dual-RNA-guided DNA endonuclease in adaptive bacterial immunity. Science. Aug. 17, 2012;337(6096):816-21.

Kitts et al., A method for producing recombinant baculovirus expression vectors at high frequency. Biotechniques. May 1993;14(5):810-7.

Komor et al., Programmable editing of a target base in genomic DNA without double-stranded DNA cleavage. Nature. May 19, 2016;533(7603):420-4.

Kosicki et al., Repair of double-strand breaks induced by CRISPR-Cas9 leads to large deletions and complex rearrangements. Nat Biotechnol. Sep. 2018;36(8):765-771.

Li et al., Metabolic engineering of *Escherichia coli* using CRISPR-Cas9 meditated genome editing. Metab Eng. Sep. 2015:31:13-21.

Lucklow et al., Efficient generation of infectious recombinant baculoviruses by site-specific transposon-mediated insertion of foreign genes into a baculovirus genome propagated in *Escherichia coli*. J Virol. Aug. 1993;67(8):4566-79.

Lucklow, Baculovirus systems for the expression of human gene products. Curr Opin Biotechnol. Oct. 1993;4(5):564-72.

Mohni et al., HMCES Maintains Genome Integrity by Shielding Abasic Sites in Single-Strand DNA. Cell. Jan. 10, 2019;176(1-2):144-153.e13.

Noia et al., Molecular mechanisms of antibody somatic hypermutation. Annu Rev Biochem. 2007:76:1-22.

Pattanayak et al., High-throughput profiling of off-target DNA cleavage reveals RNA-programmed Cas9 nuclease specificity. Nat Biotechnol. Sep. 2013;31(9):839-43.

Pines et al., Bacterial Recombineering: Genome Engineering via Phage-Based Homologous Recombination. ACS Synth Biol. Nov. 20, 2015;4(11):1176-85.

Ran et al., Genome engineering using the CRISPR-Cas9 system. Nat Protoc. Nov. 2013;8(11):2281-2308.

Rees et al., Improving the DNA specificity and applicability of base editing through protein engineering and protein delivery. Nat Commun. Jun. 6, 2017:8:15790. 10 pages.

Richardson et al., Enhancing homology-directed genome editing by catalytically active and inactive CRISPR-Cas9 using asymmetric donor DNA. Nat Biotechnol. Mar. 2016;34(3):339-44.

Sun et al., Recent advances in micro/nanoscale intracellular delivery. Nanotechnology and Precision Engineering, Mar. 2020; 3(1): 18-31.

Urlaub et al., Isolation of Chinese hamster cell mutants deficient in dihydrofolate reductase activity. Proc Natl Acad Sci U S A. Jul. 1980;77(7):4216-20.

Xia et al., Holliday junction trap shows how cells use recombination and a junction-guardian role of RecQ helicase. Sci Adv. Nov. 18, 2016;2(11):e1601605. 20 pages.

* cited by examiner

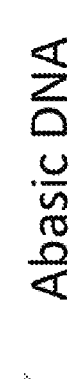
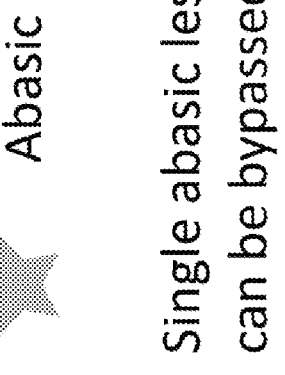
Abasic DNA
Single abasic lesions can be bypassed and repaired
Two lesions in a certain order leave an unrepaired gap in the DNA
Homologous Recombination
FIG. 1A
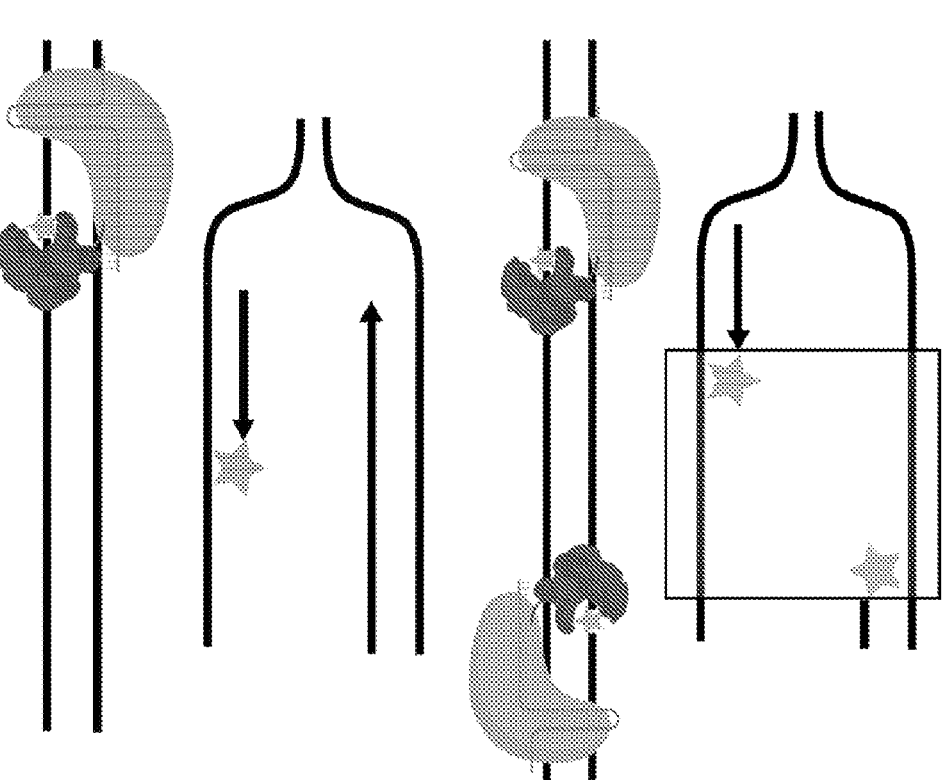

Gap editor sgRNAs

Repair template

No Targeting          Dual Targeting

*E. coli ΔxthA*

Mutation confirmed by sequencing

Efficient, non-cytotoxic editing with dual targeting in *E. coli*

*E. coli ΔxthA ΔrecF*

RecF is required for editing

SEQUENCE LISTING

```
<160> NUMBER OF SEQ ID NOS: 7

<210> SEQ ID NO 1
<211> LENGTH: 1612
<212> TYPE: PRT
<213> ORGANISM: Artificial Sequence
<220> FEATURE:
<223> OTHER INFORMATION: Synthetic

<400> SEQUENCE: 1

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
        50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
            115                 120                 125

Gln Gly Leu Arg Asp Leu Ile Ser Ser Gly Val Thr Ile Gln Ile Met
        130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
        210                 215                 220

Ala Thr Gly Leu Lys Ser Gly Ser Glu Thr Pro Gly Thr Ser Glu Ser
225                 230                 235                 240

Ala Thr Pro Glu Ser Asp Lys Lys Tyr Ser Ile Gly Leu Ala Ile Gly
                245                 250                 255

Thr Asn Ser Val Gly Trp Ala Val Ile Thr Asp Glu Tyr Lys Val Pro
            260                 265                 270

Ser Lys Lys Phe Lys Val Leu Gly Asn Thr Asp Arg His Ser Ile Lys
        275                 280                 285
```

```
Lys Asn Leu Ile Gly Ala Leu Leu Phe Asp Ser Gly Glu Thr Ala Glu
290                 295                 300

Ala Thr Arg Leu Lys Arg Thr Ala Arg Arg Arg Tyr Thr Arg Arg Lys
305                 310                 315                 320

Asn Arg Ile Cys Tyr Leu Gln Glu Ile Phe Ser Asn Glu Met Ala Lys
                325                 330                 335

Val Asp Asp Ser Phe Phe His Arg Leu Glu Glu Ser Phe Leu Val Glu
                340                 345                 350

Glu Asp Lys Lys His Glu Arg His Pro Ile Phe Gly Asn Ile Val Asp
                355                 360                 365

Glu Val Ala Tyr His Glu Lys Tyr Pro Thr Ile Tyr His Leu Arg Lys
370                 375                 380

Lys Leu Val Asp Ser Thr Asp Lys Ala Asp Leu Arg Leu Ile Tyr Leu
385                 390                 395                 400

Ala Leu Ala His Met Ile Lys Phe Arg Gly His Phe Leu Ile Glu Gly
                405                 410                 415

Asp Leu Asn Pro Asp Asn Ser Asp Val Asp Lys Leu Phe Ile Gln Leu
                420                 425                 430

Val Gln Thr Tyr Asn Gln Leu Phe Glu Glu Asn Pro Ile Asn Ala Ser
                435                 440                 445

Gly Val Asp Ala Lys Ala Ile Leu Ser Ala Arg Leu Ser Lys Ser Arg
    450                 455                 460

Arg Leu Glu Asn Leu Ile Ala Gln Leu Pro Gly Glu Lys Lys Asn Gly
465                 470                 475                 480

Leu Phe Gly Asn Leu Ile Ala Leu Ser Leu Gly Leu Thr Pro Asn Phe
                485                 490                 495

Lys Ser Asn Phe Asp Leu Ala Glu Asp Ala Lys Leu Gln Leu Ser Lys
                500                 505                 510

Asp Thr Tyr Asp Asp Asp Leu Asp Asn Leu Leu Ala Gln Ile Gly Asp
                515                 520                 525

Gln Tyr Ala Asp Leu Phe Leu Ala Ala Lys Asn Leu Ser Asp Ala Ile
    530                 535                 540

Leu Leu Ser Asp Ile Leu Arg Val Asn Thr Glu Ile Thr Lys Ala Pro
545                 550                 555                 560

Leu Ser Ala Ser Met Ile Lys Arg Tyr Asp Glu His His Gln Asp Leu
                565                 570                 575

Thr Leu Leu Lys Ala Leu Val Arg Gln Gln Leu Pro Glu Lys Tyr Lys
                580                 585                 590

Glu Ile Phe Phe Asp Gln Ser Lys Asn Gly Tyr Ala Gly Tyr Ile Asp
    595                 600                 605

Gly Gly Ala Ser Gln Glu Glu Phe Tyr Lys Phe Ile Lys Pro Ile Leu
    610                 615                 620

Glu Lys Met Asp Gly Thr Glu Glu Leu Leu Val Lys Leu Asn Arg Glu
625                 630                 635                 640

Asp Leu Leu Arg Lys Gln Arg Thr Phe Asp Asn Gly Ser Ile Pro His
                645                 650                 655

Gln Ile His Leu Gly Glu Leu His Ala Ile Leu Arg Arg Gln Glu Asp
                660                 665                 670

Phe Tyr Pro Phe Leu Lys Asp Asn Arg Glu Lys Ile Glu Lys Ile Leu
    675                 680                 685

Thr Phe Arg Ile Pro Tyr Tyr Val Gly Pro Leu Ala Arg Gly Asn Ser
    690                 695                 700
```

-continued

```
Arg Phe Ala Trp Met Thr Arg Lys Ser Glu Glu Thr Ile Thr Pro Trp
705                 710             715                 720

Asn Phe Glu Glu Val Val Asp Lys Gly Ala Ser Ala Gln Ser Phe Ile
                725             730             735

Glu Arg Met Thr Asn Phe Asp Lys Asn Leu Pro Asn Glu Lys Val Leu
            740             745             750

Pro Lys His Ser Leu Leu Tyr Glu Tyr Phe Thr Val Tyr Asn Glu Leu
            755             760             765

Thr Lys Val Lys Tyr Val Thr Glu Gly Met Arg Lys Pro Ala Phe Leu
770                 775             780

Ser Gly Glu Gln Lys Lys Ala Ile Val Asp Leu Leu Phe Lys Thr Asn
785                 790             795                 800

Arg Lys Val Thr Val Lys Gln Leu Lys Glu Asp Tyr Phe Lys Lys Ile
                805             810             815

Glu Cys Phe Asp Ser Val Glu Ile Ser Gly Val Glu Asp Arg Phe Asn
                820             825             830

Ala Ser Leu Gly Thr Tyr His Asp Leu Leu Lys Ile Ile Lys Asp Lys
            835             840             845

Asp Phe Leu Asp Asn Glu Glu Asn Glu Asp Ile Leu Glu Asp Ile Val
    850             855             860

Leu Thr Leu Thr Leu Phe Glu Asp Arg Glu Met Ile Glu Glu Arg Leu
865                 870             875                 880

Lys Thr Tyr Ala His Leu Phe Asp Asp Lys Val Met Lys Gln Leu Lys
                885             890             895

Arg Arg Arg Tyr Thr Gly Trp Gly Arg Leu Ser Arg Lys Leu Ile Asn
            900             905             910

Gly Ile Arg Asp Lys Gln Ser Gly Lys Thr Ile Leu Asp Phe Leu Lys
            915             920             925

Ser Asp Gly Phe Ala Asn Arg Asn Phe Met Gln Leu Ile His Asp Asp
    930             935             940

Ser Leu Thr Phe Lys Glu Asp Ile Gln Lys Ala Gln Val Ser Gly Gln
945                 950             955                 960

Gly Asp Ser Leu His Glu His Ile Ala Asn Leu Ala Gly Ser Pro Ala
                965             970             975

Ile Lys Lys Gly Ile Leu Gln Thr Val Lys Val Val Asp Glu Leu Val
            980             985             990

Lys Val Met Gly Arg His Lys Pro  Glu Asn Ile Val Ile  Glu Met Ala
            995             1000                1005

Arg Glu Asn Gln Thr Thr Gln  Lys Gly Gln Lys Asn  Ser Arg Glu
    1010            1015               1020

Arg Met Lys Arg Ile Glu Glu  Gly Ile Lys Glu Leu  Gly Ser Gln
    1025            1030               1035

Ile Leu Lys Glu His Pro Val  Glu Asn Thr Gln Leu  Gln Asn Glu
    1040            1045               1050

Lys Leu Tyr Leu Tyr Tyr Leu  Gln Asn Gly Arg Asp  Met Tyr Val
    1055            1060               1065

Asp Gln Glu Leu Asp Ile Asn  Arg Leu Ser Asp Tyr  Asp Val Asp
    1070            1075               1080

Ala Ile Val Pro Gln Ser Phe  Leu Lys Asp Asp Ser  Ile Asp Asn
    1085            1090               1095

Lys Val Leu Thr Arg Ser Asp  Lys Asn Arg Gly Lys  Ser Asp Asn
    1100            1105               1110

Val Pro Ser Glu Glu Val Val  Lys Lys Met Lys Asn  Tyr Trp Arg
```

```
            1115                1120                1125

Gln Leu  Leu Asn Ala Lys Leu  Ile Thr Gln Arg Lys  Phe Asp Asn
    1130                1135                1140

Leu Thr  Lys Ala Glu Arg Gly  Gly Leu Ser Glu Leu  Asp Lys Ala
    1145                1150                1155

Gly Phe  Ile Lys Arg Gln Leu  Val Glu Thr Arg Gln  Ile Thr Lys
    1160                1165                1170

His Val  Ala Gln Ile Leu Asp  Ser Arg Met Asn Thr  Lys Tyr Asp
    1175                1180                1185

Glu Asn  Asp Lys Leu Ile Arg  Glu Val Lys Val Ile  Thr Leu Lys
    1190                1195                1200

Ser Lys  Leu Val Ser Asp Phe  Arg Lys Asp Phe Gln  Phe Tyr Lys
    1205                1210                1215

Val Arg  Glu Ile Asn Asn Tyr  His His Ala His Asp  Ala Tyr Leu
    1220                1225                1230

Asn Ala  Val Val Gly Thr Ala  Leu Ile Lys Lys Tyr  Pro Lys Leu
    1235                1240                1245

Glu Ser  Glu Phe Val Tyr Gly  Asp Tyr Lys Val Tyr  Asp Val Arg
    1250                1255                1260

Lys Met  Ile Ala Lys Ser Glu  Gln Glu Ile Gly Lys  Ala Thr Ala
    1265                1270                1275

Lys Tyr  Phe Phe Tyr Ser Asn  Ile Met Asn Phe Phe  Lys Thr Glu
    1280                1285                1290

Ile Thr  Leu Ala Asn Gly Glu  Ile Arg Lys Arg Pro  Leu Ile Glu
    1295                1300                1305

Thr Asn  Gly Glu Thr Gly Glu  Ile Val Trp Asp Lys  Gly Arg Asp
    1310                1315                1320

Phe Ala  Thr Val Arg Lys Val  Leu Ser Met Pro Gln  Val Asn Ile
    1325                1330                1335

Val Lys  Lys Thr Glu Val Gln  Thr Gly Gly Phe Ser  Lys Glu Ser
    1340                1345                1350

Ile Leu  Pro Lys Arg Asn Ser  Asp Lys Leu Ile Ala  Arg Lys Lys
    1355                1360                1365

Asp Trp  Asp Pro Lys Lys Tyr  Gly Gly Phe Asp Ser  Pro Thr Val
    1370                1375                1380

Ala Tyr  Ser Val Leu Val Val  Ala Lys Val Glu Lys  Gly Lys Ser
    1385                1390                1395

Lys Lys  Leu Lys Ser Val Lys  Glu Leu Leu Gly Ile  Thr Ile Met
    1400                1405                1410

Glu Arg  Ser Ser Phe Glu Lys  Asn Pro Ile Asp Phe  Leu Glu Ala
    1415                1420                1425

Lys Gly  Tyr Lys Glu Val Lys  Lys Asp Leu Ile Ile  Lys Leu Pro
    1430                1435                1440

Lys Tyr  Ser Leu Phe Glu Leu  Glu Asn Gly Arg Lys  Arg Met Leu
    1445                1450                1455

Ala Ser  Ala Gly Glu Leu Gln  Lys Gly Asn Glu Leu  Ala Leu Pro
    1460                1465                1470

Ser Lys  Tyr Val Asn Phe Leu  Tyr Leu Ala Ser His  Tyr Glu Lys
    1475                1480                1485

Leu Lys  Gly Ser Pro Glu Asp  Asn Glu Gln Lys Gln  Leu Phe Val
    1490                1495                1500

Glu Gln  His Lys His Tyr Leu  Asp Glu Ile Ile Glu  Gln Ile Ser
    1505                1510                1515
```

-continued

```
Glu Phe Ser Lys Arg Val Ile  Leu Ala Asp Ala Asn  Leu Asp Lys
    1520                1525                1530

Val Leu Ser Ala Tyr Asn Lys  His Arg Asp Lys Pro  Ile Arg Glu
    1535                1540                1545

Gln Ala Glu Asn Ile Ile His  Leu Phe Thr Leu Thr  Asn Leu Gly
    1550                1555                1560

Ala Pro Ala Ala Phe Lys Tyr  Phe Asp Thr Thr Ile  Asp Arg Lys
    1565                1570                1575

Arg Tyr Thr Ser Thr Lys Glu  Val Leu Asp Ala Thr  Leu Ile His
    1580                1585                1590

Gln Ser Ile Thr Gly Leu Tyr  Glu Thr Arg Ile Asp  Leu Ser Gln
    1595                1600                1605

Leu Gly Gly Asp
    1610

<210> SEQ ID NO 2
<211> LENGTH: 1606
<212> TYPE: PRT
<213> ORGANISM: Artificial Sequence
<220> FEATURE:
<223> OTHER INFORMATION: Synthetic

<400> SEQUENCE: 2

Met Gly Gly Phe Gly Glu Ser Trp Lys Lys His Leu Ser Gly Glu Phe
1               5                   10                  15

Gly Lys Pro Tyr Phe Ile Lys Leu Met Gly Phe Val Ala Glu Glu Arg
            20                  25                  30

Lys His Tyr Thr Val Tyr Pro Pro Pro His Gln Val Phe Thr Trp Thr
            35                  40                  45

Gln Met Cys Asp Ile Lys Asp Val Lys Val Val Ile Leu Gly Gln Asp
    50                  55                  60

Pro Tyr His Gly Pro Asn Gln Ala His Gly Leu Cys Phe Ser Val Gln
65                  70                  75                  80

Arg Pro Val Pro Pro Pro Ser Leu Glu Asn Ile Tyr Lys Glu Leu
                85                  90                  95

Ser Thr Asp Ile Glu Asp Phe Val His Pro Gly His Gly Asp Leu Ser
            100                 105                 110

Gly Trp Ala Lys Gln Gly Val Leu Leu Leu Asp Ala Val Leu Thr Val
            115                 120                 125

Arg Ala His Gln Ala Asn Ser His Lys Glu Arg Gly Trp Glu Gln Phe
    130                 135                 140

Thr Asp Ala Val Val Ser Trp Leu Asn Gln Asn Ser Asn Gly Leu Val
145                 150                 155                 160

Phe Leu Leu Trp Gly Ser Tyr Ala Gln Lys Lys Gly Ser Ala Ile Asp
                165                 170                 175

Arg Lys Arg His His Val Leu Gln Thr Ala His Pro Ser Pro Leu Ser
            180                 185                 190

Val Tyr Arg Gly Phe Phe Gly Cys Arg His Phe Ser Lys Thr Asn Glu
            195                 200                 205

Leu Leu Gln Lys Ser Gly Lys Lys Pro Ile Asp Trp Lys Glu Leu Ser
    210                 215                 220

Gly Ser Glu Thr Pro Gly Thr Ser Glu Ser Ala Thr Pro Glu Ser Asp
225                 230                 235                 240

Lys Lys Tyr Ser Ile Gly Leu Ala Ile Gly Thr Asn Ser Val Gly Trp
                245                 250                 255
```

-continued

```
Ala Val Ile Thr Asp Glu Tyr Lys Val Pro Ser Lys Lys Phe Lys Val
            260                 265                 270

Leu Gly Asn Thr Asp Arg His Ser Ile Lys Lys Asn Leu Ile Gly Ala
            275                 280                 285

Leu Leu Phe Asp Ser Gly Glu Thr Ala Glu Ala Thr Arg Leu Lys Arg
            290                 295                 300

Thr Ala Arg Arg Arg Tyr Thr Arg Arg Lys Asn Arg Ile Cys Tyr Leu
305                 310                 315                 320

Gln Glu Ile Phe Ser Asn Glu Met Ala Lys Val Asp Asp Ser Phe Phe
                325                 330                 335

His Arg Leu Glu Glu Ser Phe Leu Val Glu Glu Asp Lys Lys His Glu
            340                 345                 350

Arg His Pro Ile Phe Gly Asn Ile Val Asp Glu Val Ala Tyr His Glu
            355                 360                 365

Lys Tyr Pro Thr Ile Tyr His Leu Arg Lys Lys Leu Val Asp Ser Thr
            370                 375                 380

Asp Lys Ala Asp Leu Arg Leu Ile Tyr Leu Ala Leu Ala His Met Ile
385                 390                 395                 400

Lys Phe Arg Gly His Phe Leu Ile Glu Gly Asp Leu Asn Pro Asp Asn
                405                 410                 415

Ser Asp Val Asp Lys Leu Phe Ile Gln Leu Val Gln Thr Tyr Asn Gln
                420                 425                 430

Leu Phe Glu Glu Asn Pro Ile Asn Ala Ser Gly Val Asp Ala Lys Ala
            435                 440                 445

Ile Leu Ser Ala Arg Leu Ser Lys Ser Arg Arg Leu Glu Asn Leu Ile
            450                 455                 460

Ala Gln Leu Pro Gly Glu Lys Lys Asn Gly Leu Phe Gly Asn Leu Ile
465                 470                 475                 480

Ala Leu Ser Leu Gly Leu Thr Pro Asn Phe Lys Ser Asn Phe Asp Leu
                485                 490                 495

Ala Glu Asp Ala Lys Leu Gln Leu Ser Lys Asp Thr Tyr Asp Asp Asp
                500                 505                 510

Leu Asp Asn Leu Leu Ala Gln Ile Gly Asp Gln Tyr Ala Asp Leu Phe
            515                 520                 525

Leu Ala Ala Lys Asn Leu Ser Asp Ala Ile Leu Leu Ser Asp Ile Leu
            530                 535                 540

Arg Val Asn Thr Glu Ile Thr Lys Ala Pro Leu Ser Ala Ser Met Ile
545                 550                 555                 560

Lys Arg Tyr Asp Glu His His Gln Asp Leu Thr Leu Leu Lys Ala Leu
                565                 570                 575

Val Arg Gln Gln Leu Pro Glu Lys Tyr Lys Glu Ile Phe Phe Asp Gln
                580                 585                 590

Ser Lys Asn Gly Tyr Ala Gly Tyr Ile Asp Gly Gly Ala Ser Gln Glu
            595                 600                 605

Glu Phe Tyr Lys Phe Ile Lys Pro Ile Leu Glu Lys Met Asp Gly Thr
            610                 615                 620

Glu Glu Leu Leu Val Lys Leu Asn Arg Glu Asp Leu Leu Arg Lys Gln
625                 630                 635                 640

Arg Thr Phe Asp Asn Gly Ser Ile Pro His Gln Ile His Leu Gly Glu
                645                 650                 655

Leu His Ala Ile Leu Arg Arg Gln Glu Asp Phe Tyr Pro Phe Leu Lys
            660                 665                 670
```

-continued

Asp Asn Arg Glu Lys Ile Glu Lys Ile Leu Thr Phe Arg Ile Pro Tyr
        675                 680                 685

Tyr Val Gly Pro Leu Ala Arg Gly Asn Ser Arg Phe Ala Trp Met Thr
        690                 695                 700

Arg Lys Ser Glu Glu Thr Ile Thr Pro Trp Asn Phe Glu Glu Val Val
705                 710                 715                 720

Asp Lys Gly Ala Ser Ala Gln Ser Phe Ile Glu Arg Met Thr Asn Phe
                725                 730                 735

Asp Lys Asn Leu Pro Asn Glu Lys Val Leu Pro Lys His Ser Leu Leu
                740                 745                 750

Tyr Glu Tyr Phe Thr Val Tyr Asn Glu Leu Thr Lys Val Lys Tyr Val
                755                 760                 765

Thr Glu Gly Met Arg Lys Pro Ala Phe Leu Ser Gly Glu Gln Lys Lys
        770                 775                 780

Ala Ile Val Asp Leu Leu Phe Lys Thr Asn Arg Lys Val Thr Val Lys
785                 790                 795                 800

Gln Leu Lys Glu Asp Tyr Phe Lys Lys Ile Glu Cys Phe Asp Ser Val
                805                 810                 815

Glu Ile Ser Gly Val Glu Asp Arg Phe Asn Ala Ser Leu Gly Thr Tyr
                820                 825                 830

His Asp Leu Leu Lys Ile Ile Lys Asp Lys Asp Phe Leu Asp Asn Glu
                835                 840                 845

Glu Asn Glu Asp Ile Leu Glu Asp Ile Val Leu Thr Leu Thr Leu Phe
        850                 855                 860

Glu Asp Arg Glu Met Ile Glu Glu Arg Leu Lys Thr Tyr Ala His Leu
865                 870                 875                 880

Phe Asp Asp Lys Val Met Lys Gln Leu Lys Arg Arg Arg Tyr Thr Gly
                885                 890                 895

Trp Gly Arg Leu Ser Arg Lys Leu Ile Asn Gly Ile Arg Asp Lys Gln
        900                 905                 910

Ser Gly Lys Thr Ile Leu Asp Phe Leu Lys Ser Asp Gly Phe Ala Asn
        915                 920                 925

Arg Asn Phe Met Gln Leu Ile His Asp Asp Ser Leu Thr Phe Lys Glu
        930                 935                 940

Asp Ile Gln Lys Ala Gln Val Ser Gly Gln Gly Asp Ser Leu His Glu
945                 950                 955                 960

His Ile Ala Asn Leu Ala Gly Ser Pro Ala Ile Lys Lys Gly Ile Leu
                965                 970                 975

Gln Thr Val Lys Val Val Asp Glu Leu Val Lys Val Met Gly Arg His
                980                 985                 990

Lys Pro Glu Asn Ile Val Ile Glu  Met Ala Arg Glu Asn  Gln Thr Thr
        995                 1000                 1005

Gln Lys  Gly Gln Lys Asn Ser  Arg Glu Arg Met Lys  Arg Ile Glu
        1010                 1015                 1020

Glu Gly  Ile Lys Glu Leu Gly  Ser Gln Ile Leu Lys  Glu His Pro
        1025                 1030                 1035

Val Glu  Asn Thr Gln Leu Gln  Asn Glu Lys Leu Tyr  Leu Tyr Tyr
        1040                 1045                 1050

Leu Gln  Asn Gly Arg Asp Met  Tyr Val Asp Gln Glu  Leu Asp Ile
        1055                 1060                 1065

Asn Arg  Leu Ser Asp Tyr Asp  Val Asp Ala Ile Val  Pro Gln Ser
        1070                 1075                 1080

Phe Leu  Lys Asp Asp Ser Ile  Asp Asn Lys Val Leu  Thr Arg Ser

-continued

```
        1085                1090                1095

Asp Lys  Asn Arg Gly Lys Ser  Asp Asn Val Pro Ser  Glu Glu Val
    1100                1105                1110

Val Lys  Lys Met Lys Asn Tyr  Trp Arg Gln Leu Leu  Asn Ala Lys
    1115                1120                1125

Leu Ile  Thr Gln Arg Lys Phe  Asp Asn Leu Thr Lys  Ala Glu Arg
    1130                1135                1140

Gly Gly  Leu Ser Glu Leu Asp  Lys Ala Gly Phe Ile  Lys Arg Gln
    1145                1150                1155

Leu Val  Glu Thr Arg Gln Ile  Thr Lys His Val Ala  Gln Ile Leu
    1160                1165                1170

Asp Ser  Arg Met Asn Thr Lys  Tyr Asp Glu Asn Asp  Lys Leu Ile
    1175                1180                1185

Arg Glu  Val Lys Val Ile Thr  Leu Lys Ser Lys Leu  Val Ser Asp
    1190                1195                1200

Phe Arg  Lys Asp Phe Gln Phe  Tyr Lys Val Arg Glu  Ile Asn Asn
    1205                1210                1215

Tyr His  His Ala His Asp Ala  Tyr Leu Asn Ala Val  Val Gly Thr
    1220                1225                1230

Ala Leu  Ile Lys Lys Tyr Pro  Lys Leu Glu Ser Glu  Phe Val Tyr
    1235                1240                1245

Gly Asp  Tyr Lys Val Tyr Asp  Val Arg Lys Met Ile  Ala Lys Ser
    1250                1255                1260

Glu Gln  Glu Ile Gly Lys Ala  Thr Ala Lys Tyr Phe  Phe Tyr Ser
    1265                1270                1275

Asn Ile  Met Asn Phe Phe Lys  Thr Glu Ile Thr Leu  Ala Asn Gly
    1280                1285                1290

Glu Ile  Arg Lys Arg Pro Leu  Ile Glu Thr Asn Gly  Glu Thr Gly
    1295                1300                1305

Glu Ile  Val Trp Asp Lys Gly  Arg Asp Phe Ala Thr  Val Arg Lys
    1310                1315                1320

Val Leu  Ser Met Pro Gln Val  Asn Ile Val Lys Lys  Thr Glu Val
    1325                1330                1335

Gln Thr  Gly Gly Phe Ser Lys  Glu Ser Ile Leu Pro  Lys Arg Asn
    1340                1345                1350

Ser Asp  Lys Leu Ile Ala Arg  Lys Lys Asp Trp Asp  Pro Lys Lys
    1355                1360                1365

Tyr Gly  Gly Phe Asp Ser Pro  Thr Val Ala Tyr Ser  Val Leu Val
    1370                1375                1380

Val Ala  Lys Val Glu Lys Gly  Lys Ser Lys Lys Leu  Lys Ser Val
    1385                1390                1395

Lys Glu  Leu Leu Gly Ile Thr  Ile Met Glu Arg Ser  Ser Phe Glu
    1400                1405                1410

Lys Asn  Pro Ile Asp Phe Leu  Glu Ala Lys Gly Tyr  Lys Glu Val
    1415                1420                1425

Lys Lys  Asp Leu Ile Ile Lys  Leu Pro Lys Tyr Ser  Leu Phe Glu
    1430                1435                1440

Leu Glu  Asn Gly Arg Lys Arg  Met Leu Ala Ser Ala  Gly Glu Leu
    1445                1450                1455

Gln Lys  Gly Asn Glu Leu Ala  Leu Pro Ser Lys Tyr  Val Asn Phe
    1460                1465                1470

Leu Tyr  Leu Ala Ser His Tyr  Glu Lys Leu Lys Gly  Ser Pro Glu
    1475                1480                1485
```

-continued

```
Asp Asn Glu Gln Lys Gln Leu  Phe Val Glu Gln His  Lys His Tyr
    1490            1495           1500

Leu Asp Glu Ile Ile Glu Gln  Ile Ser Glu Phe Ser  Lys Arg Val
    1505            1510           1515

Ile Leu Ala Asp Ala Asn Leu  Asp Lys Val Leu Ser  Ala Tyr Asn
    1520            1525           1530

Lys His Arg Asp Lys Pro Ile  Arg Glu Gln Ala Glu  Asn Ile Ile
    1535            1540           1545

His Leu Phe Thr Leu Thr Asn  Leu Gly Ala Pro Ala  Ala Phe Lys
    1550            1555           1560

Tyr Phe Asp Thr Thr Ile Asp  Arg Lys Arg Tyr Thr  Ser Thr Lys
    1565            1570           1575

Glu Val Leu Asp Ala Thr Leu  Ile His Gln Ser Ile  Thr Gly Leu
    1580            1585           1590

Tyr Glu Thr Arg Ile Asp Leu  Ser Gln Leu Gly Gly  Asp
    1595            1600           1605

<210> SEQ ID NO 3
<211> LENGTH: 1679
<212> TYPE: PRT
<213> ORGANISM: Artificial Sequence
<220> FEATURE:
<223> OTHER INFORMATION: Synthetic

<400> SEQUENCE: 3

Met Lys Leu Lys Arg Glu Tyr Asp Glu Leu Ile Lys Ala Asp Ala Val
1               5               10              15

Lys Glu Ile Ala Lys Glu Leu Gly Ser Arg Pro Leu Glu Val Ala Leu
            20              25              30

Pro Glu Lys Tyr Ile Ala Arg His Glu Glu Lys Phe Asn Met Ala Cys
        35              40              45

Glu His Ile Leu Glu Lys Asp Pro Ser Leu Phe Pro Ile Leu Lys Asn
    50              55              60

Asn Glu Phe Thr Leu Tyr Leu Lys Glu Thr Gln Val Pro Asn Thr Leu
65              70              75              80

Glu Asp Tyr Phe Ile Arg Leu Ala Ser Thr Ile Leu Ser Gln Gln Ile
            85              90              95

Ser Gly Gln Ala Ala Glu Ser Ile Lys Ala Arg Val Val Ser Leu Tyr
        100             105             110

Gly Gly Ala Phe Pro Asp Tyr Lys Ile Leu Phe Glu Asp Phe Lys Asp
        115             120             125

Pro Ala Lys Cys Ala Glu Ile Ala Lys Cys Gly Leu Ser Lys Arg Lys
    130             135             140

Met Ile Tyr Leu Glu Ser Leu Ala Val Tyr Phe Thr Glu Lys Tyr Lys
145             150             155             160

Asp Ile Glu Lys Leu Phe Gly Gln Lys Asp Asn Asp Glu Glu Val Ile
            165             170             175

Glu Ser Leu Val Thr Asn Val Lys Gly Ile Gly Pro Trp Ser Ala Lys
            180             185             190

Met Phe Leu Ile Ser Gly Leu Lys Arg Met Asp Val Phe Ala Pro Glu
        195             200             205

Asp Leu Gly Ile Ala Arg Gly Phe Ser Lys Tyr Leu Ser Asp Lys Pro
    210             215             220

Glu Leu Glu Lys Glu Leu Met Arg Glu Arg Lys Val Val Lys Lys Ser
225             230             235             240
```

-continued

```
Lys Ile Lys His Lys Lys Tyr Asn Trp Lys Ile Tyr Asp Asp Asp Ile
            245                 250                 255

Met Glu Lys Cys Ser Glu Thr Phe Ser Pro Tyr Arg Ser Val Phe Met
            260                 265                 270

Phe Ile Leu Trp Arg Leu Ala Ser Thr Asn Thr Asp Ala Met Met Lys
            275                 280                 285

Ala Glu Glu Asn Phe Val Lys Ser Ser Gly Ser Glu Thr Pro Gly Thr
        290                 295                 300

Ser Glu Ser Ala Thr Pro Glu Ser Asp Lys Lys Tyr Ser Ile Gly Leu
305                 310                 315                 320

Ala Ile Gly Thr Asn Ser Val Gly Trp Ala Val Ile Thr Asp Glu Tyr
                325                 330                 335

Lys Val Pro Ser Lys Lys Phe Lys Val Leu Gly Asn Thr Asp Arg His
            340                 345                 350

Ser Ile Lys Lys Asn Leu Ile Gly Ala Leu Leu Phe Asp Ser Gly Glu
            355                 360                 365

Thr Ala Glu Ala Thr Arg Leu Lys Arg Thr Ala Arg Arg Arg Tyr Thr
        370                 375                 380

Arg Arg Lys Asn Arg Ile Cys Tyr Leu Gln Glu Ile Phe Ser Asn Glu
385                 390                 395                 400

Met Ala Lys Val Asp Asp Ser Phe Phe His Arg Leu Glu Glu Ser Phe
                405                 410                 415

Leu Val Glu Glu Asp Lys Lys His Glu Arg His Pro Ile Phe Gly Asn
            420                 425                 430

Ile Val Asp Glu Val Ala Tyr His Glu Lys Tyr Pro Thr Ile Tyr His
            435                 440                 445

Leu Arg Lys Lys Leu Val Asp Ser Thr Asp Lys Ala Asp Leu Arg Leu
        450                 455                 460

Ile Tyr Leu Ala Leu Ala His Met Ile Lys Phe Arg Gly His Phe Leu
465                 470                 475                 480

Ile Glu Gly Asp Leu Asn Pro Asp Asn Ser Asp Val Asp Lys Leu Phe
                485                 490                 495

Ile Gln Leu Val Gln Thr Tyr Asn Gln Leu Phe Glu Glu Asn Pro Ile
            500                 505                 510

Asn Ala Ser Gly Val Asp Ala Lys Ala Ile Leu Ser Ala Arg Leu Ser
            515                 520                 525

Lys Ser Arg Arg Leu Glu Asn Leu Ile Ala Gln Leu Pro Gly Glu Lys
        530                 535                 540

Lys Asn Gly Leu Phe Gly Asn Leu Ile Ala Leu Ser Leu Gly Leu Thr
545                 550                 555                 560

Pro Asn Phe Lys Ser Asn Phe Asp Leu Ala Glu Asp Ala Lys Leu Gln
                565                 570                 575

Leu Ser Lys Asp Thr Tyr Asp Asp Asp Leu Asp Asn Leu Leu Ala Gln
            580                 585                 590

Ile Gly Asp Gln Tyr Ala Asp Leu Phe Leu Ala Ala Lys Asn Leu Ser
            595                 600                 605

Asp Ala Ile Leu Leu Ser Asp Ile Leu Arg Val Asn Thr Glu Ile Thr
        610                 615                 620

Lys Ala Pro Leu Ser Ala Ser Met Ile Lys Arg Tyr Asp Glu His His
625                 630                 635                 640

Gln Asp Leu Thr Leu Leu Lys Ala Leu Val Arg Gln Gln Leu Pro Glu
                645                 650                 655
```

-continued

```
Lys Tyr Lys Glu Ile Phe Phe Asp Gln Ser Lys Asn Gly Tyr Ala Gly
            660                 665                 670

Tyr Ile Asp Gly Gly Ala Ser Gln Glu Glu Phe Tyr Lys Phe Ile Lys
            675                 680                 685

Pro Ile Leu Glu Lys Met Asp Gly Thr Glu Glu Leu Leu Val Lys Leu
            690                 695                 700

Asn Arg Glu Asp Leu Leu Arg Lys Gln Arg Thr Phe Asp Asn Gly Ser
705                 710                 715                 720

Ile Pro His Gln Ile His Leu Gly Glu Leu His Ala Ile Leu Arg Arg
                725                 730                 735

Gln Glu Asp Phe Tyr Pro Phe Leu Lys Asp Asn Arg Glu Lys Ile Glu
                740                 745                 750

Lys Ile Leu Thr Phe Arg Ile Pro Tyr Tyr Val Gly Pro Leu Ala Arg
                755                 760                 765

Gly Asn Ser Arg Phe Ala Trp Met Thr Arg Lys Ser Glu Glu Thr Ile
            770                 775                 780

Thr Pro Trp Asn Phe Glu Glu Val Val Asp Lys Gly Ala Ser Ala Gln
785                 790                 795                 800

Ser Phe Ile Glu Arg Met Thr Asn Phe Asp Lys Asn Leu Pro Asn Glu
                805                 810                 815

Lys Val Leu Pro Lys His Ser Leu Leu Tyr Glu Tyr Phe Thr Val Tyr
                820                 825                 830

Asn Glu Leu Thr Lys Val Lys Tyr Val Thr Glu Gly Met Arg Lys Pro
                835                 840                 845

Ala Phe Leu Ser Gly Glu Gln Lys Lys Ala Ile Val Asp Leu Leu Phe
            850                 855                 860

Lys Thr Asn Arg Lys Val Thr Val Lys Gln Leu Lys Glu Asp Tyr Phe
865                 870                 875                 880

Lys Lys Ile Glu Cys Phe Asp Ser Val Glu Ile Ser Gly Val Glu Asp
                885                 890                 895

Arg Phe Asn Ala Ser Leu Gly Thr Tyr His Asp Leu Leu Lys Ile Ile
            900                 905                 910

Lys Asp Lys Asp Phe Leu Asp Asn Glu Glu Asn Glu Asp Ile Leu Glu
            915                 920                 925

Asp Ile Val Leu Thr Leu Thr Leu Phe Glu Asp Arg Glu Met Ile Glu
            930                 935                 940

Glu Arg Leu Lys Thr Tyr Ala His Leu Phe Asp Asp Lys Val Met Lys
945                 950                 955                 960

Gln Leu Lys Arg Arg Arg Tyr Thr Gly Trp Gly Arg Leu Ser Arg Lys
                965                 970                 975

Leu Ile Asn Gly Ile Arg Asp Lys Gln Ser Gly Lys Thr Ile Leu Asp
            980                 985                 990

Phe Leu Lys Ser Asp Gly Phe Ala  Asn Arg Asn Phe Met  Gln Leu Ile
            995                 1000                1005

His Asp  Asp Ser Leu Thr Phe  Lys Glu Asp Ile Gln  Lys Ala Gln
    1010                1015                1020

Val Ser  Gly Gln Gly Asp Ser  Leu His Glu His Ile  Ala Asn Leu
    1025                1030                1035

Ala Gly  Ser Pro Ala Ile Lys  Lys Gly Ile Leu Gln  Thr Val Lys
    1040                1045                1050

Val Val  Asp Glu Leu Val Lys  Val Met Gly Arg His  Lys Pro Glu
    1055                1060                1065

Asn Ile  Val Ile Glu Met Ala  Arg Glu Asn Gln Thr  Thr Gln Lys
```

-continued

```
        1070                1075                1080

Gly Gln  Lys Asn Ser Arg Glu  Arg Met Lys Arg Ile  Glu Glu Gly
    1085                1090                1095

Ile Lys  Glu Leu Gly Ser Gln  Ile Leu Lys Glu His  Pro Val Glu
    1100                1105                1110

Asn Thr  Gln Leu Gln Asn Glu  Lys Leu Tyr Leu Tyr  Tyr Leu Gln
    1115                1120                1125

Asn Gly  Arg Asp Met Tyr Val  Asp Gln Glu Leu Asp  Ile Asn Arg
    1130                1135                1140

Leu Ser  Asp Tyr Asp Val Asp  Ala Ile Val Pro Gln  Ser Phe Leu
    1145                1150                1155

Lys Asp  Asp Ser Ile Asp Asn  Lys Val Leu Thr Arg  Ser Asp Lys
    1160                1165                1170

Asn Arg  Gly Lys Ser Asp Asn  Val Pro Ser Glu Glu  Val Val Lys
    1175                1180                1185

Lys Met  Lys Asn Tyr Trp Arg  Gln Leu Leu Asn Ala  Lys Leu Ile
    1190                1195                1200

Thr Gln  Arg Lys Phe Asp Asn  Leu Thr Lys Ala Glu  Arg Gly Gly
    1205                1210                1215

Leu Ser  Glu Leu Asp Lys Ala  Gly Phe Ile Lys Arg  Gln Leu Val
    1220                1225                1230

Glu Thr  Arg Gln Ile Thr Lys  His Val Ala Gln Ile  Leu Asp Ser
    1235                1240                1245

Arg Met  Asn Thr Lys Tyr Asp  Glu Asn Asp Lys Leu  Ile Arg Glu
    1250                1255                1260

Val Lys  Val Ile Thr Leu Lys  Ser Lys Leu Val Ser  Asp Phe Arg
    1265                1270                1275

Lys Asp  Phe Gln Phe Tyr Lys  Val Arg Glu Ile Asn  Asn Tyr His
    1280                1285                1290

His Ala  His Asp Ala Tyr Leu  Asn Ala Val Val Gly  Thr Ala Leu
    1295                1300                1305

Ile Lys  Lys Tyr Pro Lys Leu  Glu Ser Glu Phe Val  Tyr Gly Asp
    1310                1315                1320

Tyr Lys  Val Tyr Asp Val Arg  Lys Met Ile Ala Lys  Ser Glu Gln
    1325                1330                1335

Glu Ile  Gly Lys Ala Thr Ala  Lys Tyr Phe Phe Tyr  Ser Asn Ile
    1340                1345                1350

Met Asn  Phe Phe Lys Thr Glu  Ile Thr Leu Ala Asn  Gly Glu Ile
    1355                1360                1365

Arg Lys  Arg Pro Leu Ile Glu  Thr Asn Gly Glu Thr  Gly Glu Ile
    1370                1375                1380

Val Trp  Asp Lys Gly Arg Asp  Phe Ala Thr Val Arg  Lys Val Leu
    1385                1390                1395

Ser Met  Pro Gln Val Asn Ile  Val Lys Lys Thr Glu  Val Gln Thr
    1400                1405                1410

Gly Gly  Phe Ser Lys Glu Ser  Ile Leu Pro Lys Arg  Asn Ser Asp
    1415                1420                1425

Lys Leu  Ile Ala Arg Lys Lys  Asp Trp Asp Pro Lys  Lys Tyr Gly
    1430                1435                1440

Gly Phe  Asp Ser Pro Thr Val  Ala Tyr Ser Val Leu  Val Val Ala
    1445                1450                1455

Lys Val  Glu Lys Gly Lys Ser  Lys Lys Leu Lys Ser  Val Lys Glu
    1460                1465                1470
```

-continued

```
Leu Leu  Gly Ile Thr Ile Met  Glu Arg Ser Ser Phe  Glu Lys Asn
    1475             1480             1485

Pro Ile  Asp Phe Leu Glu Ala  Lys Gly Tyr Lys Glu  Val Lys Lys
    1490             1495             1500

Asp Leu  Ile Ile Lys Leu Pro  Lys Tyr Ser Leu Phe  Glu Leu Glu
    1505             1510             1515

Asn Gly  Arg Lys Arg Met Leu  Ala Ser Ala Gly Glu  Leu Gln Lys
    1520             1525             1530

Gly Asn  Glu Leu Ala Leu Pro  Ser Lys Tyr Val Asn  Phe Leu Tyr
    1535             1540             1545

Leu Ala  Ser His Tyr Glu Lys  Leu Lys Gly Ser Pro  Glu Asp Asn
    1550             1555             1560

Glu Gln  Lys Gln Leu Phe Val  Glu Gln His Lys His  Tyr Leu Asp
    1565             1570             1575

Glu Ile  Ile Glu Gln Ile Ser  Glu Phe Ser Lys Arg  Val Ile Leu
    1580             1585             1590

Ala Asp  Ala Asn Leu Asp Lys  Val Leu Ser Ala Tyr  Asn Lys His
    1595             1600             1605

Arg Asp  Lys Pro Ile Arg Glu  Gln Ala Glu Asn Ile  Ile His Leu
    1610             1615             1620

Phe Thr  Leu Thr Asn Leu Gly  Ala Pro Ala Ala Phe  Lys Tyr Phe
    1625             1630             1635

Asp Thr  Thr Ile Asp Arg Lys  Arg Tyr Thr Ser Thr  Lys Glu Val
    1640             1645             1650

Leu Asp  Ala Thr Leu Ile His  Gln Ser Ile Thr Gly  Leu Tyr Glu
    1655             1660             1665

Thr Arg  Ile Asp Leu Ser Gln  Leu Gly Gly Asp
    1670             1675

<210> SEQ ID NO 4
<211> LENGTH: 1602
<212> TYPE: PRT
<213> ORGANISM: Artificial Sequence
<220> FEATURE:
<223> OTHER INFORMATION: Synthetic

<400> SEQUENCE: 4

Met Gly His Leu Thr Arg Leu Gly Leu Glu Phe Phe Asp Gln Pro Ala
1               5               10              15

Val Pro Leu Ala Arg Ala Phe Leu Gly Gln Val Leu Val Arg Arg Leu
            20              25              30

Pro Asn Gly Thr Glu Leu Arg Gly Arg Ile Val Glu Thr Glu Ala Tyr
        35              40              45

Leu Gly Pro Glu Asp Glu Ala Ala His Ser Arg Gly Gly Arg Gln Thr
    50              55              60

Pro Arg Asn Arg Gly Met Phe Met Lys Pro Gly Thr Leu Tyr Val Tyr
65              70              75              80

Ile Ile Tyr Gly Met Tyr Phe Cys Met Asn Ile Ser Ser Gln Gly Asp
                85              90              95

Gly Ala Cys Val Leu Leu Arg Ala Leu Glu Pro Leu Glu Gly Leu Glu
            100             105             110

Thr Met Arg Gln Leu Arg Ser Thr Leu Arg Lys Gly Thr Ala Ser Arg
        115             120             125

Val Leu Lys Asp Arg Glu Leu Cys Ser Gly Pro Ser Lys Leu Cys Gln
    130             135             140
```

```
Ala Leu Ala Ile Asn Lys Ser Phe Asp Gln Arg Asp Leu Ala Gln Asp
145                 150                 155                 160

Glu Ala Val Trp Leu Glu Arg Gly Pro Leu Glu Pro Ser Glu Pro Ala
                165                 170                 175

Val Val Ala Ala Ala Arg Val Gly Val Gly His Ala Gly Glu Trp Ala
                180                 185                 190

Arg Lys Pro Leu Arg Phe Tyr Val Arg Gly Ser Pro Trp Val Ser Val
            195                 200                 205

Val Asp Arg Val Ala Glu Gln Asp Thr Gln Ala Ser Gly Ser Glu Thr
    210                 215                 220

Pro Gly Thr Ser Glu Ser Ala Thr Pro Glu Ser Asp Lys Lys Tyr Ser
225                 230                 235                 240

Ile Gly Leu Ala Ile Gly Thr Asn Ser Val Gly Trp Ala Val Ile Thr
                245                 250                 255

Asp Glu Tyr Lys Val Pro Ser Lys Lys Phe Lys Val Leu Gly Asn Thr
            260                 265                 270

Asp Arg His Ser Ile Lys Lys Asn Leu Ile Gly Ala Leu Leu Phe Asp
        275                 280                 285

Ser Gly Glu Thr Ala Glu Ala Thr Arg Leu Lys Arg Thr Ala Arg Arg
    290                 295                 300

Arg Tyr Thr Arg Arg Lys Asn Arg Ile Cys Tyr Leu Gln Glu Ile Phe
305                 310                 315                 320

Ser Asn Glu Met Ala Lys Val Asp Asp Ser Phe Phe His Arg Leu Glu
                325                 330                 335

Glu Ser Phe Leu Val Glu Glu Asp Lys Lys His Glu Arg His Pro Ile
            340                 345                 350

Phe Gly Asn Ile Val Asp Glu Val Ala Tyr His Glu Lys Tyr Pro Thr
            355                 360                 365

Ile Tyr His Leu Arg Lys Lys Leu Val Asp Ser Thr Asp Lys Ala Asp
    370                 375                 380

Leu Arg Leu Ile Tyr Leu Ala Leu Ala His Met Ile Lys Phe Arg Gly
385                 390                 395                 400

His Phe Leu Ile Glu Gly Asp Leu Asn Pro Asp Asn Ser Asp Val Asp
                405                 410                 415

Lys Leu Phe Ile Gln Leu Val Gln Thr Tyr Asn Gln Leu Phe Glu Glu
            420                 425                 430

Asn Pro Ile Asn Ala Ser Gly Val Asp Ala Lys Ala Ile Leu Ser Ala
            435                 440                 445

Arg Leu Ser Lys Ser Arg Arg Leu Glu Asn Leu Ile Ala Gln Leu Pro
    450                 455                 460

Gly Glu Lys Lys Asn Gly Leu Phe Gly Asn Leu Ile Ala Leu Ser Leu
465                 470                 475                 480

Gly Leu Thr Pro Asn Phe Lys Ser Asn Phe Asp Leu Ala Glu Asp Ala
                485                 490                 495

Lys Leu Gln Leu Ser Lys Asp Thr Tyr Asp Asp Asp Leu Asp Asn Leu
            500                 505                 510

Leu Ala Gln Ile Gly Asp Gln Tyr Ala Asp Leu Phe Leu Ala Ala Lys
        515                 520                 525

Asn Leu Ser Asp Ala Ile Leu Leu Ser Asp Ile Leu Arg Val Asn Thr
    530                 535                 540

Glu Ile Thr Lys Ala Pro Leu Ser Ala Ser Met Ile Lys Arg Tyr Asp
545                 550                 555                 560
```

-continued

```
Glu His His Gln Asp Leu Thr Leu Leu Lys Ala Leu Val Arg Gln Gln
                565                 570                 575

Leu Pro Glu Lys Tyr Lys Glu Ile Phe Phe Asp Gln Ser Lys Asn Gly
            580                 585                 590

Tyr Ala Gly Tyr Ile Asp Gly Gly Ala Ser Gln Glu Glu Phe Tyr Lys
            595                 600                 605

Phe Ile Lys Pro Ile Leu Glu Lys Met Asp Gly Thr Glu Glu Leu Leu
    610                 615                 620

Val Lys Leu Asn Arg Glu Asp Leu Leu Arg Lys Gln Arg Thr Phe Asp
625                 630                 635                 640

Asn Gly Ser Ile Pro His Gln Ile His Leu Gly Glu Leu His Ala Ile
                645                 650                 655

Leu Arg Arg Gln Glu Asp Phe Tyr Pro Phe Leu Lys Asp Asn Arg Glu
            660                 665                 670

Lys Ile Glu Lys Ile Leu Thr Phe Arg Ile Pro Tyr Tyr Val Gly Pro
            675                 680                 685

Leu Ala Arg Gly Asn Ser Arg Phe Ala Trp Met Thr Arg Lys Ser Glu
    690                 695                 700

Glu Thr Ile Thr Pro Trp Asn Phe Glu Glu Val Val Asp Lys Gly Ala
705                 710                 715                 720

Ser Ala Gln Ser Phe Ile Glu Arg Met Thr Asn Phe Asp Lys Asn Leu
                725                 730                 735

Pro Asn Glu Lys Val Leu Pro Lys His Ser Leu Leu Tyr Glu Tyr Phe
            740                 745                 750

Thr Val Tyr Asn Glu Leu Thr Lys Val Lys Tyr Val Thr Glu Gly Met
            755                 760                 765

Arg Lys Pro Ala Phe Leu Ser Gly Glu Gln Lys Lys Ala Ile Val Asp
    770                 775                 780

Leu Leu Phe Lys Thr Asn Arg Lys Val Thr Val Lys Gln Leu Lys Glu
785                 790                 795                 800

Asp Tyr Phe Lys Lys Ile Glu Cys Phe Asp Ser Val Glu Ile Ser Gly
                805                 810                 815

Val Glu Asp Arg Phe Asn Ala Ser Leu Gly Thr Tyr His Asp Leu Leu
            820                 825                 830

Lys Ile Ile Lys Asp Lys Asp Phe Leu Asp Asn Glu Glu Asn Glu Asp
            835                 840                 845

Ile Leu Glu Asp Ile Val Leu Thr Leu Thr Leu Phe Glu Asp Arg Glu
    850                 855                 860

Met Ile Glu Glu Arg Leu Lys Thr Tyr Ala His Leu Phe Asp Asp Lys
865                 870                 875                 880

Val Met Lys Gln Leu Lys Arg Arg Arg Tyr Thr Gly Trp Gly Arg Leu
                885                 890                 895

Ser Arg Lys Leu Ile Asn Gly Ile Arg Asp Lys Gln Ser Gly Lys Thr
            900                 905                 910

Ile Leu Asp Phe Leu Lys Ser Asp Gly Phe Ala Asn Arg Asn Phe Met
            915                 920                 925

Gln Leu Ile His Asp Asp Ser Leu Thr Phe Lys Glu Asp Ile Gln Lys
    930                 935                 940

Ala Gln Val Ser Gly Gln Gly Asp Ser Leu His Glu His Ile Ala Asn
945                 950                 955                 960

Leu Ala Gly Ser Pro Ala Ile Lys Lys Gly Ile Leu Gln Thr Val Lys
                965                 970                 975

Val Val Asp Glu Leu Val Lys Val Met Gly Arg His Lys Pro Glu Asn
```

-continued

```
                980                 985                 990
Ile Val Ile Glu Met Ala Arg Glu  Asn Gln Thr Thr Gln  Lys Gly Gln
        995                 1000                1005

Lys Asn  Ser Arg Glu Arg Met  Lys Arg Ile Glu Glu  Gly Ile Lys
    1010                1015                1020

Glu Leu  Gly Ser Gln Ile Leu  Lys Glu His Pro Val  Glu Asn Thr
    1025                1030                1035

Gln Leu  Gln Asn Glu Lys Leu  Tyr Leu Tyr Tyr Leu  Gln Asn Gly
    1040                1045                1050

Arg Asp  Met Tyr Val Asp Gln  Glu Leu Asp Ile Asn  Arg Leu Ser
    1055                1060                1065

Asp Tyr  Asp Val Asp Ala Ile  Val Pro Gln Ser Phe  Leu Lys Asp
    1070                1075                1080

Asp Ser  Ile Asp Asn Lys Val  Leu Thr Arg Ser Asp  Lys Asn Arg
    1085                1090                1095

Gly Lys  Ser Asp Asn Val Pro  Ser Glu Glu Val Val  Lys Lys Met
    1100                1105                1110

Lys Asn  Tyr Trp Arg Gln Leu  Leu Asn Ala Lys Leu  Ile Thr Gln
    1115                1120                1125

Arg Lys  Phe Asp Asn Leu Thr  Lys Ala Glu Arg Gly  Gly Leu Ser
    1130                1135                1140

Glu Leu  Asp Lys Ala Gly Phe  Ile Lys Arg Gln Leu  Val Glu Thr
    1145                1150                1155

Arg Gln  Ile Thr Lys His Val  Ala Gln Ile Leu Asp  Ser Arg Met
    1160                1165                1170

Asn Thr  Lys Tyr Asp Glu Asn  Asp Lys Leu Ile Arg  Glu Val Lys
    1175                1180                1185

Val Ile  Thr Leu Lys Ser Lys  Leu Val Ser Asp Phe  Arg Lys Asp
    1190                1195                1200

Phe Gln  Phe Tyr Lys Val Arg  Glu Ile Asn Asn Tyr  His His Ala
    1205                1210                1215

His Asp  Ala Tyr Leu Asn Ala  Val Val Gly Thr Ala  Leu Ile Lys
    1220                1225                1230

Lys Tyr  Pro Lys Leu Glu Ser  Glu Phe Val Tyr Gly  Asp Tyr Lys
    1235                1240                1245

Val Tyr  Asp Val Arg Lys Met  Ile Ala Lys Ser Glu  Gln Glu Ile
    1250                1255                1260

Gly Lys  Ala Thr Ala Lys Tyr  Phe Phe Tyr Ser Asn  Ile Met Asn
    1265                1270                1275

Phe Phe  Lys Thr Glu Ile Thr  Leu Ala Asn Gly Glu  Ile Arg Lys
    1280                1285                1290

Arg Pro  Leu Ile Glu Thr Asn  Gly Glu Thr Gly Glu  Ile Val Trp
    1295                1300                1305

Asp Lys  Gly Arg Asp Phe Ala  Thr Val Arg Lys Val  Leu Ser Met
    1310                1315                1320

Pro Gln  Val Asn Ile Val Lys  Lys Thr Glu Val Gln  Thr Gly Gly
    1325                1330                1335

Phe Ser  Lys Glu Ser Ile Leu  Pro Lys Arg Asn Ser  Asp Lys Leu
    1340                1345                1350

Ile Ala  Arg Lys Lys Asp Trp  Asp Pro Lys Lys Tyr  Gly Gly Phe
    1355                1360                1365

Asp Ser  Pro Thr Val Ala Tyr  Ser Val Leu Val Val  Ala Lys Val
    1370                1375                1380
```

```
Glu Lys  Gly Lys Ser Lys Lys  Leu Lys Ser Val Lys  Glu Leu Leu
    1385              1390              1395

Gly Ile  Thr Ile Met Glu Arg  Ser Ser Phe Glu Lys  Asn Pro Ile
    1400              1405              1410

Asp Phe  Leu Glu Ala Lys Gly  Tyr Lys Glu Val Lys  Lys Asp Leu
    1415              1420              1425

Ile Ile  Lys Leu Pro Lys Tyr  Ser Leu Phe Glu Leu  Glu Asn Gly
    1430              1435              1440

Arg Lys  Arg Met Leu Ala Ser  Ala Gly Glu Leu Gln  Lys Gly Asn
    1445              1450              1455

Glu Leu  Ala Leu Pro Ser Lys  Tyr Val Asn Phe Leu  Tyr Leu Ala
    1460              1465              1470

Ser His  Tyr Glu Lys Leu Lys  Gly Ser Pro Glu Asp  Asn Glu Gln
    1475              1480              1485

Lys Gln  Leu Phe Val Glu Gln  His Lys His Tyr Leu  Asp Glu Ile
    1490              1495              1500

Ile Glu  Gln Ile Ser Glu Phe  Ser Lys Arg Val Ile  Leu Ala Asp
    1505              1510              1515

Ala Asn  Leu Asp Lys Val Leu  Ser Ala Tyr Asn Lys  His Arg Asp
    1520              1525              1530

Lys Pro  Ile Arg Glu Gln Ala  Glu Asn Ile Ile His  Leu Phe Thr
    1535              1540              1545

Leu Thr  Asn Leu Gly Ala Pro  Ala Ala Phe Lys Tyr  Phe Asp Thr
    1550              1555              1560

Thr Ile  Asp Arg Lys Arg Tyr  Thr Ser Thr Lys Glu  Val Leu Asp
    1565              1570              1575

Ala Thr  Leu Ile His Gln Ser  Ile Thr Gly Leu Tyr  Glu Thr Arg
    1580              1585              1590

Ile Asp  Leu Ser Gln Leu Gly  Gly Asp
    1595              1600

<210> SEQ ID NO 5
<211> LENGTH: 1472
<212> TYPE: PRT
<213> ORGANISM: Artificial Sequence
<220> FEATURE:
<223> OTHER INFORMATION: Synthetic

<400> SEQUENCE: 5

Met Ser Ser Glu Thr Gly Pro Val Ala Val Asp Pro Thr Leu Arg Arg
1               5                  10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
            115                 120                 125
```

```
Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
                180                 185                 190

Leu Asn Ile Leu Arg Arg Lys Gln Pro Gln Leu Thr Phe Phe Thr Ile
                195                 200                 205

Ala Leu Gln Ser Cys His Tyr Gln Arg Leu Pro Pro His Ile Leu Trp
    210                 215                 220

Ala Thr Gly Leu Lys Ser Gly Ser Glu Thr Pro Gly Thr Ser Glu Ser
225                 230                 235                 240

Ala Thr Pro Glu Ser Ser Lys Leu Glu Lys Phe Thr Asn Cys Tyr Ser
                245                 250                 255

Leu Ser Lys Thr Leu Arg Phe Lys Ala Ile Pro Val Gly Lys Thr Gln
                260                 265                 270

Glu Asn Ile Asp Asn Lys Arg Leu Leu Val Glu Asp Glu Lys Arg Ala
    275                 280                 285

Glu Asp Tyr Lys Gly Val Lys Lys Leu Leu Asp Arg Tyr Tyr Leu Ser
    290                 295                 300

Phe Ile Asn Asp Val Leu His Ser Ile Lys Leu Lys Asn Leu Asn Asn
305                 310                 315                 320

Tyr Ile Ser Leu Phe Arg Lys Lys Thr Arg Thr Glu Lys Glu Asn Lys
                325                 330                 335

Glu Leu Glu Asn Leu Glu Ile Asn Leu Arg Lys Glu Ile Ala Lys Ala
                340                 345                 350

Phe Lys Gly Asn Glu Gly Tyr Lys Ser Leu Phe Lys Lys Asp Ile Ile
                355                 360                 365

Glu Thr Ile Leu Pro Glu Phe Leu Asp Asp Lys Asp Glu Ile Ala Leu
    370                 375                 380

Val Asn Ser Phe Asn Gly Phe Thr Thr Ala Phe Thr Gly Phe Phe Asp
385                 390                 395                 400

Asn Arg Glu Asn Met Phe Ser Glu Glu Ala Lys Ser Thr Ser Ile Ala
                405                 410                 415

Phe Arg Cys Ile Asn Glu Asn Leu Thr Arg Tyr Ile Ser Asn Met Asp
                420                 425                 430

Ile Phe Glu Lys Val Asp Ala Ile Phe Asp Lys His Glu Val Gln Glu
                435                 440                 445

Ile Lys Glu Lys Ile Leu Asn Ser Asp Tyr Asp Val Glu Asp Phe Phe
    450                 455                 460

Glu Gly Glu Phe Phe Asn Phe Val Leu Thr Gln Glu Gly Ile Asp Val
465                 470                 475                 480

Tyr Asn Ala Ile Ile Gly Gly Phe Val Thr Glu Ser Gly Glu Lys Ile
                485                 490                 495

Lys Gly Leu Asn Glu Tyr Ile Asn Leu Tyr Asn Gln Lys Thr Lys Gln
                500                 505                 510

Lys Leu Pro Lys Phe Lys Pro Leu Tyr Lys Gln Val Leu Ser Asp Arg
                515                 520                 525

Glu Ser Leu Ser Phe Tyr Gly Glu Gly Tyr Thr Ser Asp Glu Glu Val
    530                 535                 540
```

-continued

```
Leu Glu Val Phe Arg Asn Thr Leu Asn Lys Asn Ser Glu Ile Phe Ser
545                 550                 555                 560

Ser Ile Lys Lys Leu Glu Lys Leu Phe Lys Asn Phe Asp Glu Tyr Ser
                565                 570                 575

Ser Ala Gly Ile Phe Val Lys Asn Gly Pro Ala Ile Ser Thr Ile Ser
                580                 585                 590

Lys Asp Ile Phe Gly Glu Trp Asn Val Ile Arg Asp Lys Trp Asn Ala
                595                 600                 605

Glu Tyr Asp Asp Ile His Leu Lys Lys Lys Ala Val Val Thr Glu Lys
        610                 615                 620

Tyr Glu Asp Asp Arg Arg Lys Ser Phe Lys Lys Ile Gly Ser Phe Ser
625                 630                 635                 640

Leu Glu Gln Leu Gln Glu Tyr Ala Asp Ala Asp Leu Ser Val Val Glu
                645                 650                 655

Lys Leu Lys Glu Ile Ile Ile Gln Lys Val Asp Glu Ile Tyr Lys Val
                660                 665                 670

Tyr Gly Ser Ser Glu Lys Leu Phe Asp Ala Asp Phe Val Leu Glu Lys
        675                 680                 685

Ser Leu Lys Lys Asn Asp Ala Val Val Ala Ile Met Lys Asp Leu Leu
        690                 695                 700

Asp Ser Val Lys Ser Phe Glu Asn Tyr Ile Lys Ala Phe Phe Gly Glu
705                 710                 715                 720

Gly Lys Glu Thr Asn Arg Asp Glu Ser Phe Tyr Gly Asp Phe Val Leu
                725                 730                 735

Ala Tyr Asp Ile Leu Leu Lys Val Asp His Ile Tyr Asp Ala Ile Arg
                740                 745                 750

Asn Tyr Val Thr Gln Lys Pro Tyr Ser Lys Asp Lys Phe Lys Leu Tyr
                755                 760                 765

Phe Gln Asn Pro Gln Phe Met Gly Gly Trp Asp Lys Asp Lys Glu Thr
        770                 775                 780

Asp Tyr Arg Ala Thr Ile Leu Arg Tyr Gly Ser Lys Tyr Tyr Leu Ala
785                 790                 795                 800

Ile Met Asp Lys Lys Tyr Ala Lys Cys Leu Gln Lys Ile Asp Lys Asp
                805                 810                 815

Asp Val Asn Gly Asn Tyr Glu Lys Ile Asn Tyr Lys Leu Leu Pro Gly
                820                 825                 830

Pro Asn Lys Met Leu Pro Lys Val Phe Phe Ser Lys Lys Trp Met Ala
        835                 840                 845

Tyr Tyr Asn Pro Ser Glu Asp Ile Gln Lys Ile Tyr Lys Asn Gly Thr
        850                 855                 860

Phe Lys Lys Gly Asp Met Phe Asn Leu Asn Asp Cys His Lys Leu Ile
865                 870                 875                 880

Asp Phe Phe Lys Asp Ser Ile Ser Arg Tyr Pro Lys Trp Ser Asn Ala
                885                 890                 895

Tyr Asp Phe Asn Phe Ser Glu Thr Glu Lys Tyr Lys Asp Ile Ala Gly
                900                 905                 910

Phe Tyr Arg Glu Val Glu Glu Gln Gly Tyr Lys Val Ser Phe Glu Ser
        915                 920                 925

Ala Ser Lys Lys Glu Val Asp Lys Leu Val Glu Glu Gly Lys Leu Tyr
        930                 935                 940

Met Phe Gln Ile Tyr Asn Lys Asp Phe Ser Asp Lys Ser His Gly Thr
945                 950                 955                 960

Pro Asn Leu His Thr Met Tyr Phe Lys Leu Leu Phe Asp Glu Asn Asn
```

-continued

```
                965                 970                 975

His Gly Gln Ile Arg Leu Ser Gly Gly Ala Glu Leu Phe Met Arg Arg
            980                 985                 990

Ala Ser Leu Lys Lys Glu Glu Leu  Val Val His Pro Ala  Asn Ser Pro
        995                 1000                 1005

Ile Ala  Asn Lys Asn Pro Asp  Asn Pro Lys Lys Thr  Thr Thr Leu
    1010                 1015                 1020

Ser Tyr  Asp Val Tyr Lys Asp  Lys Arg Phe Ser Glu  Asp Gln Tyr
    1025                 1030                 1035

Glu Leu  His Ile Pro Ile Ala  Ile Asn Lys Cys Pro  Lys Asn Ile
    1040                 1045                 1050

Phe Lys  Ile Asn Thr Glu Val  Arg Val Leu Leu Lys  His Asp Asp
    1055                 1060                 1065

Asn Pro  Tyr Val Ile Gly Ile  Asp Arg Gly Glu Arg  Asn Leu Leu
    1070                 1075                 1080

Tyr Ile  Val Val Val Asp Gly  Lys Gly Asn Ile Val  Glu Gln Tyr
    1085                 1090                 1095

Ser Leu  Asn Glu Ile Ile Asn  Asn Phe Asn Gly Ile  Arg Ile Lys
    1100                 1105                 1110

Thr Asp  Tyr His Ser Leu Leu  Asp Lys Lys Glu Lys  Glu Arg Phe
    1115                 1120                 1125

Glu Ala  Arg Gln Asn Trp Thr  Ser Ile Glu Asn Ile  Lys Glu Leu
    1130                 1135                 1140

Lys Ala  Gly Tyr Ile Ser Gln  Val Val His Lys Ile  Cys Glu Leu
    1145                 1150                 1155

Val Glu  Lys Tyr Asp Ala Val  Ile Ala Leu Glu Asp  Leu Asn Ser
    1160                 1165                 1170

Gly Phe  Lys Asn Ser Arg Val  Lys Val Glu Lys Gln  Val Tyr Gln
    1175                 1180                 1185

Lys Phe  Glu Lys Met Leu Ile  Asp Lys Leu Asn Tyr  Met Val Asp
    1190                 1195                 1200

Lys Lys  Ser Asn Pro Cys Ala  Thr Gly Gly Ala Leu  Lys Gly Tyr
    1205                 1210                 1215

Gln Ile  Thr Asn Lys Phe Glu  Ser Phe Lys Ser Met  Ser Thr Gln
    1220                 1225                 1230

Asn Gly  Phe Ile Phe Tyr Ile  Pro Ala Trp Leu Thr  Ser Lys Ile
    1235                 1240                 1245

Asp Pro  Ser Thr Gly Phe Val  Asn Leu Leu Lys Thr  Lys Tyr Thr
    1250                 1255                 1260

Ser Ile  Ala Asp Ser Lys Lys  Phe Ile Ser Ser Phe  Asp Arg Ile
    1265                 1270                 1275

Met Tyr  Val Pro Glu Glu Asp  Leu Phe Glu Phe Ala  Leu Asp Tyr
    1280                 1285                 1290

Lys Asn  Phe Ser Arg Thr Asp  Ala Asp Tyr Ile Lys  Lys Trp Lys
    1295                 1300                 1305

Leu Tyr  Ser Tyr Gly Asn Arg  Ile Arg Ile Phe Arg  Asn Pro Lys
    1310                 1315                 1320

Lys Asn  Asn Val Phe Asp Trp  Glu Glu Val Cys Leu  Thr Ser Ala
    1325                 1330                 1335

Tyr Lys  Glu Leu Phe Asn Lys  Tyr Gly Ile Asn Tyr  Gln Gln Gly
    1340                 1345                 1350

Asp Ile  Arg Ala Leu Leu Cys  Glu Gln Ser Asp Lys  Ala Phe Tyr
    1355                 1360                 1365
```

-continued

```
Ser Ser  Phe Met Ala Leu Met  Ser Leu Met Leu Gln  Met Arg Asn
    1370             1375             1380

Ser Ile  Thr Gly Arg Thr Asp  Val Asp Phe Leu Ile  Ser Pro Val
    1385             1390             1395

Lys Asn  Ser Asp Gly Ile Phe  Tyr Asp Ser Arg Asn  Tyr Glu Ala
    1400             1405             1410

Gln Glu  Asn Ala Ile Leu Pro  Lys Asn Ala Asp Ala  Asn Gly Ala
    1415             1420             1425

Tyr Asn  Ile Ala Arg Lys Val  Leu Trp Ala Ile Gly  Gln Phe Lys
    1430             1435             1440

Lys Ala  Glu Asp Glu Lys Leu  Asp Lys Val Lys Ile  Ala Ile Ser
    1445             1450             1455

Asn Lys  Glu Trp Leu Glu Tyr  Ala Gln Thr Ser Val  Lys His
    1460             1465             1470

<210> SEQ ID NO 6
<211> LENGTH: 1619
<212> TYPE: PRT
<213> ORGANISM: Artificial Sequence
<220> FEATURE:
<223> OTHER INFORMATION: Synthetic

<400> SEQUENCE: 6

Met Ser Ser Glu Thr Gly Pro Val Ala Val Asp Pro Thr Leu Arg Arg
1               5                  10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg His Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Cys Ile Tyr Ile Ala Arg Leu Tyr His His Glu Asp Pro Arg Asn Arg
            115                 120                 125

Gln Gly Leu Arg Asp Leu Ile Ser Ser Gly Val Thr Ile Gln Ile Met
        130                 135                 140

Thr Glu Gln Glu Ser Gly Tyr Cys Trp Arg Asn Phe Val Asn Tyr Ser
145                 150                 155                 160

Pro Ser Asn Glu Ala Asn Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Ser Phe Thr Ile
            195                 200                 205

Ala Leu Gln Ser Cys His Tyr Gln Arg Leu Pro Pro His Ile Leu Trp
        210                 215                 220

Ala Thr Gly Leu Lys Ser Gly Ser Glu Thr Pro Gly Thr Ser Glu Ser
225                 230                 235                 240

Ala Thr Pro Glu Ser Glu Lys Lys Tyr Ser Ile Gly Leu Ala Ile Gly
                245                 250                 255
```

```
Thr Asn Ser Val Gly Trp Ala Val Ile Thr Asp Asp Tyr Lys Val Pro
            260                 265                 270

Ser Lys Lys Phe Lys Val Leu Gly Asn Thr Asn Arg Lys Ser Ile Lys
        275                 280                 285

Lys Asn Leu Met Gly Ala Leu Leu Phe Asp Ser Gly Glu Thr Ala Glu
    290                 295                 300

Ala Thr Arg Leu Lys Arg Thr Ala Arg Arg Tyr Thr Arg Arg Lys
305                 310                 315                 320

Asn Arg Ile Arg Tyr Leu Gln Glu Ile Phe Ala Asn Glu Met Ala Lys
                325                 330                 335

Leu Asp Asp Ser Phe Phe Gln Arg Leu Glu Glu Ser Phe Leu Val Glu
            340                 345                 350

Glu Asp Lys Lys Asn Glu Arg His Pro Ile Phe Gly Asn Leu Ala Asp
        355                 360                 365

Glu Val Ala Tyr His Arg Asn Tyr Pro Thr Ile Tyr His Leu Arg Lys
    370                 375                 380

Lys Leu Ala Asp Ser Pro Glu Lys Ala Asp Leu Arg Leu Ile Tyr Leu
385                 390                 395                 400

Ala Leu Ala His Ile Ile Lys Phe Arg Gly His Phe Leu Ile Glu Gly
                405                 410                 415

Lys Leu Asn Ala Glu Asn Ser Asp Val Ala Lys Leu Phe Tyr Gln Leu
            420                 425                 430

Ile Gln Thr Tyr Asn Gln Leu Phe Glu Glu Ser Pro Leu Asp Glu Ile
        435                 440                 445

Glu Val Asp Ala Lys Gly Ile Leu Ser Ala Arg Leu Ser Lys Ser Lys
    450                 455                 460

Arg Leu Glu Lys Leu Ile Ala Val Phe Pro Asn Glu Lys Lys Asn Gly
465                 470                 475                 480

Leu Phe Gly Asn Ile Ile Ala Leu Ala Leu Gly Leu Thr Pro Asn Phe
                485                 490                 495

Lys Ser Asn Phe Asp Leu Thr Glu Asp Ala Lys Leu Gln Leu Ser Lys
            500                 505                 510

Asp Thr Tyr Asp Asp Asp Leu Asp Glu Leu Leu Gly Gln Ile Gly Asp
        515                 520                 525

Gln Tyr Ala Asp Leu Phe Ser Ala Ala Lys Asn Leu Ser Asp Ala Ile
    530                 535                 540

Leu Leu Ser Asp Ile Leu Arg Ser Asn Ser Glu Val Thr Lys Ala Pro
545                 550                 555                 560

Leu Ser Ala Ser Met Val Lys Arg Tyr Asp Glu His His Gln Asp Leu
                565                 570                 575

Ala Leu Leu Lys Thr Leu Val Arg Gln Gln Phe Pro Glu Lys Tyr Ala
            580                 585                 590

Glu Ile Phe Lys Asp Asp Thr Lys Asn Gly Tyr Ala Gly Tyr Val Gly
        595                 600                 605

Ile Gly Ile Lys His Arg Lys Arg Thr Thr Lys Leu Ala Thr Gln Glu
    610                 615                 620

Glu Phe Tyr Lys Phe Ile Lys Pro Ile Leu Glu Lys Met Asp Gly Ala
625                 630                 635                 640

Glu Glu Leu Leu Ala Lys Leu Asn Arg Asp Asp Leu Leu Arg Lys Gln
                645                 650                 655

Arg Thr Phe Asp Asn Gly Ser Ile Pro His Gln Ile His Leu Lys Glu
            660                 665                 670
```

-continued

```
Leu His Ala Ile Leu Arg Arg Gln Glu Glu Phe Tyr Pro Phe Leu Lys
        675             680             685

Glu Asn Arg Glu Lys Ile Glu Lys Ile Leu Thr Phe Arg Ile Pro Tyr
    690             695             700

Tyr Val Gly Pro Leu Ala Arg Gly Asn Ser Arg Phe Ala Trp Leu Thr
705             710             715             720

Arg Lys Ser Glu Glu Ala Ile Thr Pro Trp Asn Phe Glu Glu Val Val
            725             730             735

Asp Lys Gly Ala Ser Ala Gln Ser Phe Ile Glu Arg Met Thr Asn Phe
            740             745             750

Asp Glu Gln Leu Pro Asn Lys Lys Val Leu Pro Lys His Ser Leu Leu
        755             760             765

Tyr Glu Tyr Phe Thr Val Tyr Asn Glu Leu Thr Lys Val Lys Tyr Val
    770             775             780

Thr Glu Arg Met Arg Lys Pro Glu Phe Leu Ser Gly Glu Gln Lys Lys
785             790             795             800

Ala Ile Val Asp Leu Leu Phe Lys Thr Asn Arg Lys Val Thr Val Lys
            805             810             815

Gln Leu Lys Glu Asp Tyr Phe Lys Lys Ile Glu Cys Phe Asp Ser Val
        820             825             830

Glu Ile Ile Gly Val Glu Asp Arg Phe Asn Ala Ser Leu Gly Thr Tyr
        835             840             845

His Asp Leu Leu Lys Ile Ile Lys Asp Lys Asp Phe Leu Asp Asn Glu
    850             855             860

Glu Asn Glu Asp Ile Leu Glu Asp Ile Val Leu Thr Leu Thr Leu Phe
865             870             875             880

Glu Asp Arg Glu Met Ile Glu Glu Arg Leu Lys Thr Tyr Ala His Leu
            885             890             895

Phe Asp Asp Lys Val Met Lys Gln Leu Lys Arg Arg His Tyr Thr Gly
            900             905             910

Trp Gly Arg Leu Ser Arg Lys Met Ile Asn Gly Ile Arg Asp Lys Gln
        915             920             925

Ser Gly Lys Thr Ile Leu Asp Phe Leu Lys Ser Asp Gly Phe Ser Asn
    930             935             940

Arg Asn Phe Met Gln Leu Ile His Asp Asp Ser Leu Thr Phe Lys Glu
945             950             955             960

Glu Ile Glu Lys Ala Gln Val Ser Gly Gln Gly Asp Ser Leu His Glu
            965             970             975

Gln Ile Ala Asp Leu Ala Gly Ser Pro Ala Ile Lys Lys Gly Ile Leu
        980             985             990

Gln Thr Val Lys Ile Val Asp Glu  Leu Val Lys Val Met  Gly His Lys
        995             1000            1005

Pro Glu  Asn Ile Val Ile Glu  Met Ala Arg Glu Asn  Gln Thr Thr
    1010            1015            1020

Thr Lys  Gly Leu Gln Gln Ser  Arg Glu Arg Lys Lys  Arg Ile Glu
    1025            1030            1035

Glu Gly  Ile Lys Glu Leu Glu  Ser Gln Ile Leu Lys  Glu Asn Pro
    1040            1045            1050

Val Glu  Asn Thr Gln Leu Gln  Asn Glu Lys Leu Tyr  Leu Tyr Tyr
    1055            1060            1065

Leu Gln  Asn Gly Arg Asp Met  Tyr Val Asp Gln Glu  Leu Asp Ile
    1070            1075            1080

Asn Arg  Leu Ser Asp Tyr Asp  Val Asp Ala Ile Val  Pro Gln Ser
```

-continued

```
        1085                    1090                    1095

Phe Ile  Lys Asp Asp Ser Ile  Asp Asn Lys Val Leu  Thr Arg Ser
    1100                    1105                    1110

Val Glu  Asn Arg Gly Lys Ser  Asp Asn Val Pro Ser  Glu Glu Val
    1115                    1120                    1125

Val Lys  Lys Met Lys Asn Tyr  Trp Arg Gln Leu Leu  Asn Ala Lys
    1130                    1135                    1140

Leu Ile  Thr Gln Arg Lys Phe  Asp Asn Leu Thr Lys  Ala Glu Arg
    1145                    1150                    1155

Gly Gly  Leu Ser Glu Ala Asp  Lys Ala Gly Phe Ile  Lys Arg Gln
    1160                    1165                    1170

Leu Val  Glu Thr Arg Gln Ile  Thr Lys His Val Ala  Arg Ile Leu
    1175                    1180                    1185

Asp Ser  Arg Met Asn Thr Lys  Arg Asp Lys Asn Asp  Lys Pro Ile
    1190                    1195                    1200

Arg Glu  Val Lys Val Ile Thr  Leu Lys Ser Lys Leu  Val Ser Asp
    1205                    1210                    1215

Phe Arg  Lys Asp Phe Gln Leu  Tyr Lys Val Arg Asp  Ile Asn Asn
    1220                    1225                    1230

Tyr His  His Ala His Asp Ala  Tyr Leu Asn Ala Val  Val Gly Thr
    1235                    1240                    1245

Ala Leu  Ile Lys Lys Tyr Pro  Lys Leu Glu Ser Glu  Phe Val Tyr
    1250                    1255                    1260

Gly Asp  Tyr Lys Val Tyr Asp  Val Arg Lys Met Ile  Ala Lys Ser
    1265                    1270                    1275

Glu Gln  Glu Ile Gly Lys Ala  Thr Ala Lys Arg Phe  Phe Tyr Ser
    1280                    1285                    1290

Asn Ile  Met Asn Phe Phe Lys  Thr Glu Val Lys Leu  Ala Asn Gly
    1295                    1300                    1305

Glu Ile  Arg Lys Arg Pro Leu  Ile Glu Thr Asn Gly  Glu Thr Gly
    1310                    1315                    1320

Glu Val  Val Trp Asn Lys Glu  Lys Asp Phe Ala Thr  Val Arg Lys
    1325                    1330                    1335

Val Leu  Ala Met Pro Gln Val  Asn Ile Val Lys Lys  Thr Glu Val
    1340                    1345                    1350

Gln Thr  Gly Gly Phe Ser Lys  Glu Ser Ile Leu Ser  Lys Arg Glu
    1355                    1360                    1365

Ser Ala  Lys Leu Ile Pro Arg  Lys Lys Gly Trp Asp  Thr Arg Lys
    1370                    1375                    1380

Tyr Gly  Gly Phe Gly Ser Pro  Thr Val Ala Tyr Ser  Ile Leu Val
    1385                    1390                    1395

Val Ala  Lys Val Glu Lys Gly  Lys Ala Lys Lys Leu  Lys Ser Val
    1400                    1405                    1410

Lys Val  Leu Val Gly Ile Thr  Ile Met Glu Lys Gly  Ser Tyr Glu
    1415                    1420                    1425

Lys Asp  Pro Ile Gly Phe Leu  Glu Ala Lys Gly Tyr  Lys Asp Ile
    1430                    1435                    1440

Lys Lys  Glu Leu Ile Phe Lys  Leu Pro Lys Tyr Ser  Leu Phe Glu
    1445                    1450                    1455

Leu Glu  Asn Gly Arg Arg Arg  Met Leu Ala Ser Ala  Thr Glu Leu
    1460                    1465                    1470

Gln Lys  Ala Asn Glu Leu Val  Leu Pro Gln His Leu  Val Arg Leu
    1475                    1480                    1485
```

-continued

```
Leu Tyr  Tyr Thr Gln Asn Ile  Ser Ala Thr Thr Gly  Ser Asn Asn
    1490             1495             1500

Leu Gly  Tyr Ile Glu Gln His  Arg Glu Glu Phe Lys  Glu Ile Phe
    1505             1510             1515

Glu Lys  Ile Ile Asp Phe Ser  Glu Lys Tyr Ile Leu  Lys Asn Lys
    1520             1525             1530

Val Asn  Ser Asn Leu Lys Ser  Ser Phe Asp Glu Gln  Phe Ala Val
    1535             1540             1545

Ser Asp  Ser Ile Leu Leu Ser  Asn Ser Phe Val Ser  Leu Leu Lys
    1550             1555             1560

Tyr Thr  Ser Phe Gly Ala Ser  Gly Gly Phe Thr Phe  Leu Asp Leu
    1565             1570             1575

Asp Val  Lys Gln Gly Arg Leu  Arg Tyr Gln Thr Val  Thr Glu Val
    1580             1585             1590

Leu Asp  Ala Thr Leu Ile Tyr  Gln Ser Ile Thr Gly  Leu Tyr Glu
    1595             1600             1605

Thr Arg  Thr Asp Leu Ser Gln  Leu Gly Gly Asp
    1610             1615
```

```
<210> SEQ ID NO 7
<211> LENGTH: 1619
<212> TYPE: PRT
<213> ORGANISM: Artificial Sequence
<220> FEATURE:
<223> OTHER INFORMATION: Synthetic

<400> SEQUENCE: 7

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg His Phe Cys Pro Asn Thr
65                  70                  75                  80

Arg Cys Ser Ile Thr Trp Phe Leu Ser Trp Ser Pro Cys Gly Glu Cys
            85                  90                  95

Ser Arg Ala Ile Thr Glu Phe Leu Ser Arg Tyr Pro His Val Thr Leu
            100                 105                 110

Cys Ile Tyr Ile Ala Arg Leu Tyr His His Glu Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala Asn Trp Pro Arg Tyr Pro His Leu Trp Val Arg
                165                 170                 175

Leu Tyr Val Leu Glu Leu Tyr Cys Ile Ile Leu Gly Leu Pro Pro Cys
                180                 185                 190

Leu Asn Ile Leu Arg Arg Lys Gln Pro Gln Leu Thr Ser Phe Thr Ile
        195                 200                 205

Ala Leu Gln Ser Cys His Tyr Gln Arg Leu Pro Pro His Ile Leu Trp
    210                 215                 220
```

-continued

```
Ala Thr Gly Leu Lys Ser Gly Ser Glu Thr Pro Gly Thr Ser Glu Ser
225             230             235             240

Ala Thr Pro Glu Ser Glu Lys Lys Tyr Ser Ile Gly Leu Ala Ile Gly
            245             250             255

Thr Asn Ser Val Gly Trp Ala Val Ile Thr Asp Asp Tyr Lys Val Pro
            260             265             270

Ser Lys Lys Phe Lys Val Leu Gly Asn Thr Asn Arg Lys Ser Ile Lys
            275             280             285

Lys Asn Leu Met Gly Ala Leu Leu Phe Asp Ser Gly Glu Thr Ala Glu
            290             295             300

Ala Thr Arg Leu Lys Arg Thr Ala Arg Arg Arg Tyr Thr Arg Arg Lys
305             310             315             320

Asn Arg Ile Arg Tyr Leu Gln Glu Ile Phe Ala Asn Glu Met Ala Lys
            325             330             335

Leu Asp Asp Ser Phe Phe Gln Arg Leu Glu Glu Ser Phe Leu Val Glu
            340             345             350

Glu Asp Lys Lys Asn Glu Arg His Pro Ile Phe Gly Asn Leu Ala Asp
            355             360             365

Glu Val Ala Tyr His Arg Asn Tyr Pro Thr Ile Tyr His Leu Arg Lys
            370             375             380

Lys Leu Ala Asp Ser Pro Glu Lys Ala Asp Leu Arg Leu Ile Tyr Leu
385             390             395             400

Ala Leu Ala His Ile Ile Lys Phe Arg Gly His Phe Leu Ile Glu Gly
            405             410             415

Lys Leu Asn Ala Glu Asn Ser Asp Val Ala Lys Leu Phe Tyr Gln Leu
            420             425             430

Ile Gln Thr Tyr Asn Gln Leu Phe Glu Glu Ser Pro Leu Asp Glu Ile
            435             440             445

Glu Val Asp Ala Lys Gly Ile Leu Ser Ala Arg Leu Ser Lys Ser Lys
            450             455             460

Arg Leu Glu Lys Leu Ile Ala Val Phe Pro Asn Glu Lys Lys Asn Gly
465             470             475             480

Leu Phe Gly Asn Ile Ile Ala Leu Ala Leu Gly Leu Thr Pro Asn Phe
            485             490             495

Lys Ser Asn Phe Asp Leu Thr Glu Asp Ala Lys Leu Gln Leu Ser Lys
            500             505             510

Asp Thr Tyr Asp Asp Asp Leu Asp Glu Leu Leu Gly Gln Ile Gly Asp
            515             520             525

Gln Tyr Ala Asp Leu Phe Ser Ala Ala Lys Asn Leu Ser Asp Ala Ile
            530             535             540

Leu Leu Ser Asp Ile Leu Arg Ser Asn Ser Glu Val Thr Lys Ala Pro
545             550             555             560

Leu Ser Ala Ser Met Val Lys Arg Tyr Asp Glu His His Gln Asp Leu
            565             570             575

Ala Leu Leu Lys Thr Leu Val Arg Gln Gln Phe Pro Glu Lys Tyr Ala
            580             585             590

Glu Ile Phe Lys Asp Asp Thr Lys Asn Gly Tyr Ala Gly Tyr Val Gly
            595             600             605

Ile Gly Ile Lys His Arg Lys Arg Thr Thr Lys Leu Ala Thr Gln Glu
            610             615             620

Glu Phe Tyr Lys Phe Ile Lys Pro Ile Leu Glu Lys Met Asp Gly Ala
625             630             635             640
```

```
Glu Glu Leu Leu Ala Lys Leu Asn Arg Asp Asp Leu Leu Arg Lys Gln
            645             650             655

Arg Thr Phe Asp Asn Gly Ser Ile Pro His Gln Ile His Leu Lys Glu
            660             665             670

Leu His Ala Ile Leu Arg Arg Gln Glu Glu Phe Tyr Pro Phe Leu Lys
            675             680             685

Glu Asn Arg Glu Lys Ile Glu Lys Ile Leu Thr Phe Arg Ile Pro Tyr
    690             695             700

Tyr Val Gly Pro Leu Ala Arg Gly Asn Ser Arg Phe Ala Trp Leu Thr
705             710             715             720

Arg Lys Ser Glu Glu Ala Ile Thr Pro Trp Asn Phe Glu Glu Val Val
            725             730             735

Asp Lys Gly Ala Ser Ala Gln Ser Phe Ile Glu Arg Met Thr Asn Phe
            740             745             750

Asp Glu Gln Leu Pro Asn Lys Lys Val Leu Pro Lys His Ser Leu Leu
            755             760             765

Tyr Glu Tyr Phe Thr Val Tyr Asn Glu Leu Thr Lys Val Lys Tyr Val
    770             775             780

Thr Glu Arg Met Arg Lys Pro Glu Phe Leu Ser Gly Glu Gln Lys Lys
785             790             795             800

Ala Ile Val Asp Leu Leu Phe Lys Thr Asn Arg Lys Val Thr Val Lys
            805             810             815

Gln Leu Lys Glu Asp Tyr Phe Lys Lys Ile Glu Cys Phe Asp Ser Val
            820             825             830

Glu Ile Ile Gly Val Glu Asp Arg Phe Asn Ala Ser Leu Gly Thr Tyr
            835             840             845

His Asp Leu Leu Lys Ile Ile Lys Asp Lys Asp Phe Leu Asp Asn Glu
    850             855             860

Glu Asn Glu Asp Ile Leu Glu Asp Ile Val Leu Thr Leu Thr Leu Phe
865             870             875             880

Glu Asp Arg Glu Met Ile Glu Glu Arg Leu Lys Thr Tyr Ala His Leu
            885             890             895

Phe Asp Asp Lys Val Met Lys Gln Leu Lys Arg Arg His Tyr Thr Gly
            900             905             910

Trp Gly Arg Leu Ser Arg Lys Met Ile Asn Gly Ile Arg Asp Lys Gln
            915             920             925

Ser Gly Lys Thr Ile Leu Asp Phe Leu Lys Ser Asp Gly Phe Ser Asn
    930             935             940

Arg Asn Phe Met Gln Leu Ile His Asp Asp Ser Leu Thr Phe Lys Glu
945             950             955             960

Glu Ile Glu Lys Ala Gln Val Ser Gly Gln Gly Asp Ser Leu His Glu
            965             970             975

Gln Ile Ala Asp Leu Ala Gly Ser Pro Ala Ile Lys Lys Gly Ile Leu
            980             985             990

Gln Thr Val Lys Ile Val Asp Glu  Leu Val Lys Val Met  Gly His Lys
            995             1000            1005

Pro Glu  Asn Ile Val Ile Glu  Met Ala Arg Glu Asn  Gln Thr Thr
    1010            1015            1020

Thr Lys  Gly Leu Gln Gln Ser  Arg Glu Arg Lys Lys  Arg Ile Glu
    1025            1030            1035

Glu Gly  Ile Lys Glu Leu Glu  Ser Gln Ile Leu Lys  Glu Asn Pro
    1040            1045            1050

Val Glu  Asn Thr Gln Leu Gln  Asn Glu Lys Leu Tyr  Leu Tyr Tyr
```

|  |  |  |  |  |  |  |  |  |  |  |  |
|---|---|---|---|---|---|---|---|---|---|---|---|
| 1055 | | | 1060 | | | | | | 1065 | | |

Leu Gln Asn Gly Arg Asp Met Tyr Val Asp Gln Glu Leu Asp Ile
 1070        1075          1080

Asn Arg Leu Ser Asp Tyr Asp Val Asp His Ile Val Pro Gln Ser
 1085        1090          1095

Phe Ile Lys Asp Asp Ser Ile Asp Asn Lys Val Leu Thr Arg Ser
 1100        1105          1110

Val Glu Asn Arg Gly Lys Ser Asp Asn Val Pro Ser Glu Glu Val
 1115        1120          1125

Val Lys Lys Met Lys Asn Tyr Trp Arg Gln Leu Leu Asn Ala Lys
 1130        1135          1140

Leu Ile Thr Gln Arg Lys Phe Asp Asn Leu Thr Lys Ala Glu Arg
 1145        1150          1155

Gly Gly Leu Ser Glu Ala Asp Lys Ala Gly Phe Ile Lys Arg Gln
 1160        1165          1170

Leu Val Glu Thr Arg Gln Ile Thr Lys His Val Ala Arg Ile Leu
 1175        1180          1185

Asp Ser Arg Met Asn Thr Lys Arg Asp Lys Asn Asp Lys Pro Ile
 1190        1195          1200

Arg Glu Val Lys Val Ile Thr Leu Lys Ser Lys Leu Val Ser Asp
 1205        1210          1215

Phe Arg Lys Asp Phe Gln Leu Tyr Lys Val Arg Asp Ile Asn Asn
 1220        1225          1230

Tyr His His Ala His Asp Ala Tyr Leu Asn Ala Val Val Gly Thr
 1235        1240          1245

Ala Leu Ile Lys Lys Tyr Pro Lys Leu Glu Ser Glu Phe Val Tyr
 1250        1255          1260

Gly Asp Tyr Lys Val Tyr Asp Val Arg Lys Met Ile Ala Lys Ser
 1265        1270          1275

Glu Gln Glu Ile Gly Lys Ala Thr Ala Lys Arg Phe Phe Tyr Ser
 1280        1285          1290

Asn Ile Met Asn Phe Phe Lys Thr Glu Val Lys Leu Ala Asn Gly
 1295        1300          1305

Glu Ile Arg Lys Arg Pro Leu Ile Glu Thr Asn Gly Glu Thr Gly
 1310        1315          1320

Glu Val Val Trp Asn Lys Glu Lys Asp Phe Ala Thr Val Arg Lys
 1325        1330          1335

Val Leu Ala Met Pro Gln Val Asn Ile Val Lys Lys Thr Glu Val
 1340        1345          1350

Gln Thr Gly Gly Phe Ser Lys Glu Ser Ile Leu Ser Lys Arg Glu
 1355        1360          1365

Ser Ala Lys Leu Ile Pro Arg Lys Lys Gly Trp Asp Thr Arg Lys
 1370        1375          1380

Tyr Gly Gly Phe Gly Ser Pro Thr Val Ala Tyr Ser Ile Leu Val
 1385        1390          1395

Val Ala Lys Val Glu Lys Gly Lys Ala Lys Lys Leu Lys Ser Val
 1400        1405          1410

Lys Val Leu Val Gly Ile Thr Ile Met Glu Lys Gly Ser Tyr Glu
 1415        1420          1425

Lys Asp Pro Ile Gly Phe Leu Glu Ala Lys Gly Tyr Lys Asp Ile
 1430        1435          1440

Lys Lys Glu Leu Ile Phe Lys Leu Pro Lys Tyr Ser Leu Phe Glu
 1445        1450          1455

-continued

```
Leu Glu  Asn Gly Arg Arg Arg  Met Leu Ala Ser Ala  Thr Glu Leu
    1460                1465                1470

Gln Lys  Ala Asn Glu Leu Val  Leu Pro Gln His Leu  Val Arg Leu
    1475                1480                1485

Leu Tyr  Tyr Thr Gln Asn Ile  Ser Ala Thr Thr Gly  Ser Asn Asn
    1490                1495                1500

Leu Gly  Tyr Ile Glu Gln His  Arg Glu Glu Phe Lys  Glu Ile Phe
    1505                1510                1515

Glu Lys  Ile Ile Asp Phe Ser  Glu Lys Tyr Ile Leu  Lys Asn Lys
    1520                1525                1530

Val Asn  Ser Asn Leu Lys Ser  Ser Phe Asp Glu Gln  Phe Ala Val
    1535                1540                1545

Ser Asp  Ser Ile Leu Leu Ser  Asn Ser Phe Val Ser  Leu Leu Lys
    1550                1555                1560

Tyr Thr  Ser Phe Gly Ala Ser  Gly Gly Phe Thr Phe  Leu Asp Leu
    1565                1570                1575

Asp Val  Lys Gln Gly Arg Leu  Arg Tyr Gln Thr Val  Thr Glu Val
    1580                1585                1590

Leu Asp  Ala Thr Leu Ile Tyr  Gln Ser Ile Thr Gly  Leu Tyr Glu
    1595                1600                1605

Thr Arg  Thr Asp Leu Ser Gln  Leu Gly Gly Asp
    1610                1615
```

COMPOSITIONS, METHODS, AND SYSTEMS FOR GENOME EDITING TECHNOLOGY

CROSS REFERENCE TO RELATED APPLICATIONS

This application claims priority to and the benefit of U.S. Provisional Patent Application No. 62/988,262 filed Mar. 11, 2020, which is incorporated herein by reference in its entirety for all purposes.

GOVERNMENT FUNDING

This invention was made with government support under grant number R35 GM119561 awarded by the National Institutes of Health (NIH). The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 98,126 Byte ASCII (Text) file named "2021-03-09_38270-601_SQL_ST25.txt," created on Mar. 9, 2021.

FIELD

The present disclosure provides compositions, methods, and systems related to genome editing technology. In particular, the present disclosure provides a novel CRISPR-based genome editing technology that involves the generation of abasic sites to facilitate genetic recombination, without the need for breaks in the target DNA. The compositions, methods, and systems described herein address many of the drawbacks of currently available approaches, including off-target effects and cellular toxicity.

BACKGROUND

CRISPR-based genome editing tools have found widespread application, relying on their easily programmable targeting and robust activity. Early use of these CRISPR-based tools has focused on the ability of Cas nucleases to cleave DNA, which involves a double-stranded break that severs the polymer chains linking DNA. In the process of repairing the cleaved DNA, a genomic edit is introduced. DNA cleavage is, however, among the most toxic cellular events; DNA cleavage sets off cellular alarm systems which lead to mutations, DNA re-arrangements, and/or loss of cellular viability. Therefore, there is a need for efficient CRISPR-Cas gene editing platforms that do not rely on introducing double-stranded breaks as part of CRISPR-Cas genome editing applications.

SUMMARY

Embodiments of the present disclosure include compositions for targeted editing of a nucleic acid. In accordance with these embodiments, the compositions include a gap editor complex comprising a DNA-recognition domain and a DNA-modifying domain, and at least one guide RNA molecule. In some embodiments, the gap editor complex binds a DNA target sequence and induces formation of at least one abasic site in the DNA target.

In some embodiments, the DNA-recognition domain comprises at least one Cas protein or fragment thereof lacking deoxyribonuclease activity. In some embodiments, the DNA-recognition domain comprises a complex of Cas proteins lacking deoxyribonuclease activity. In some embodiments, the Cas protein or Cas protein complex comprises a Type I Cascade, a Type II Cas9, a Type IV effector module, a Type V Cas12, and combinations thereof. In some embodiments, the DNA-recognition domain comprises a deoxyribonuclease-inactivated Cas9. In some embodiments, the Cas protein or Cas protein complex comprises a catalytically active Cas protein combined with a truncated guide RNA that allows DNA binding but not cleavage.

In some embodiments, the DNA-modifying domain catalyzes formation of the at least one abasic site in the DNA target sequence. In some embodiments, the DNA-modifying domain comprises glycosylase activity, deaminase activity, oxidase activity, nucleosidase activity, hydroxylase, hydrolase activity, and combinations thereof. In some embodiments, the DNA-modifying domain comprises a cytidine deaminase.

In some embodiments, the DNA-recognition domain comprises a Cas protein or fragment thereof having nickase activity. In some embodiments, the DNA-recognition domain and the DNA-modifying domain are functionally coupled. In some embodiments, functionally coupled includes polypeptide fusions, peptide tags, peptide linkers, RNA tags, and combinations thereof.

In some embodiments, the at least one guide RNA comprises a handle sequence and a targeting sequence. In some embodiments, the targeting sequence in the at least one guide RNA is complementary to the DNA target sequence. In some embodiments, the composition comprises one guide RNA. In some embodiments, the composition comprises at least a first and a second guide RNA. In some embodiments, the first guide RNA is complementary to a first DNA target sequence and the second guide RNA is complementary to a second DNA target sequence. In some embodiments, the first and the second DNA target sequences are on opposite strands of a double-stranded DNA molecule.

In some embodiments, the at least one abasic site is generated in the DNA strand complementary to the DNA target sequence. In some embodiments, the at least one abasic site is generated outside the DNA target sequence. In some embodiments, the gap editor complex induces formation of at least two abasic sites in two distinct DNA target sequences on opposite strands of a double-stranded DNA molecule.

In some embodiments, the compositions further include a donor nucleic acid template. In some embodiments, the presence of the donor nucleic acid template facilitates homology-directed gap recombination or oligonucleotide-mediated recombination, wherein the donor nucleic acid template or a fragment thereof is recombined into the double-stranded DNA molecule.

In some embodiments, the composition further comprises at least one gap editor accessory factor. In some embodiments, the at least one gap editor accessory factor comprises a protein involved in DNA modification or repair. In some embodiments, the at least one gap editor accessory factor is recruited to the gap editor complex via interaction with the DNA-modifying domain, the DNA-recognition domain, and/or the at least one guide RNA. In some embodiments, the at least one gap editor accessory factor comprises Rap, lambda Beta, lambda Orf, RecT, a reverse transcriptase (e.g., MMLV, Ec86), a deactivated or dominant-negative abasic site exonuclease (e.g., Exonuclease III, APE1), YedK, HMCES, ExoI, Exonuclease III, PRIMPOL, RecJ, RECQ1, Uracil DNA glycosylase, and combinations thereof. In some embodiments, the at least one gap editor accessory factor comprises a protein or RNA having or conferring deoxyribonuclease activity, wherein the deoxyribonuclease activity counter-selects against cells in which template-mediated editing of the DNA target has not occurred.

Embodiments of the present disclosure also include a kit or system for targeted editing of a nucleic acid. In accordance with these embodiments, the kit or system includes a gap editor complex comprising a DNA-recognition domain and a DNA-modifying domain, and at least one guide RNA molecule. In some embodiments, the gap editor complex binds a DNA target sequence and induces formation of at least one abasic site in the DNA target. In some embodiments, the kit or system further includes a donor nucleic acid template, and/or a gap editor accessory factor.

Embodiments of the present disclosure also include methods for targeted editing of a nucleic acid. In accordance with these embodiments, the methods include introducing a gap editor complex comprising a DNA-recognition domain and a DNA-modifying domain, and at least one guide RNA molecule into a cell, and assessing the cell for presence of a desired genetic alteration.

In some embodiments of the method, the gap editor complex and the guide RNA molecule are introduced into the cell as a polypeptide(s), mRNA(s), and/or DNA expression construct(s). In some embodiments, the method further includes introducing a donor nucleic acid template into the cell. In some embodiments, the method further includes introducing at least one gap editor accessory factor into the cell as a polypeptide(s), mRNA(s), and/or DNA expression construct(s). In some embodiments of the method, at least one of these components is introduced into the cell as part of a gene drive system.

In some embodiments, the cell is a prokaryotic cell or a eukaryotic cell. In some embodiments, the cell is a bacterial cell. In some embodiments, the cell is a mammalian cell. In some embodiments, the cell is a plant cell.

In some embodiments, the method leads to a reduced degree of indel formation, chromosomal inversions, or DNA duplications.

In some embodiments, cell viability is enhanced and/or cell toxicity is reduced.

In some embodiments, endogenous nuclease activity in the cell is attenuated.

Other aspects and embodiments of the disclosure will be apparent in light of the following detailed description.

BRIEF DESCRIPTION OF THE DRAWINGS

FIGS. 1A-1B include representative schematic diagrams of site-specific introduction of abasic sites to create a long duration gap in genomic DNA (FIG. 1A), and successful genome editing that repairs the function of a gene target (FIG. 1B).

FIGS. 4A-4B include representative results of experiments demonstrating that targeting an essential gene, rpoB, produces a defined mutation conferring resistance to the antibiotic rifampicin (FIG. 4A), which was confirmed by sequencing (FIG. 4B).

FIG. 5B demonstrates gap editor-directed recombination involving only a single guide RNA, for which rates of genome editing are significantly enhanced, albeit to less of a degree as compared to using two guide RNAs.

DETAILED DESCRIPTION

The present disclosure provides compositions, methods, and systems related to genome editing technology. In particular, the present disclosure provides a novel CRISPR-based genome editing technology that involves the generation of abasic sites to facilitate genetic recombination, without introducing DNA breaks. The compositions, methods, and systems described herein are designed to leverage a DNA gap repair pathway to edit genomic DNA with minimal toxic side-effects. Single-stranded gaps in DNA regularly occur as a byproduct of environmental DNA damage. These gaps are often repaired by homologous recombination, a commonly used pathway for editing genomic DNA.

Figure 1B:
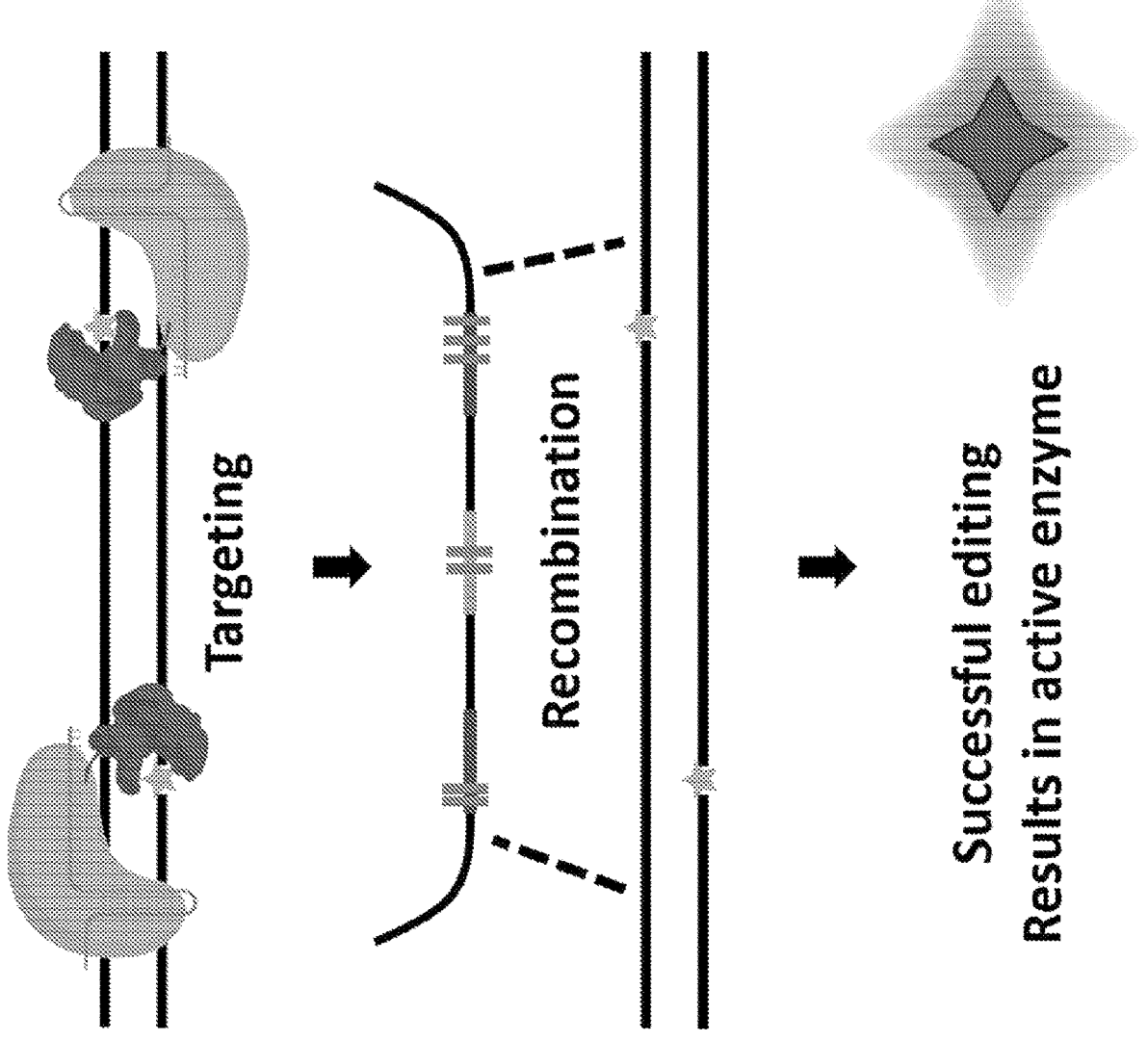

Recent work has shown that damaged nucleotides, arranged in a particular order on the DNA, leads to a long duration gap in DNA. As described further herein, it was discovered that certain enzymes fused to a nuclease-inactive Cas protein (referred to herein as "gap editors") can be used to introduce this DNA damage in a site-specific manner and subsequently drive homologous recombination with a supplied DNA repair template. The nucleotide damage caused by gap editors will take the form of an abasic site. Abasic sites in the correct orientation can create a long-duration DNA gap in a desired location (FIG. 1), which is then repaired by a synthetic DNA repair template encoding a desired edit. This approach does not involve active induction of single-stranded or double-stranded breaks in the DNA target molecule.

Compositions, methods, and systems related to the gap editors of the present disclosure are distinct from currently available gene editing technologies. For example, the original and most widely used CRISPR-Cas genome editing technology relies on Cas nucleases introducing a double-stranded break which is then repaired through homologous recombination via an editing template, similar to gap editors. While broadly applied, the toxicity of double-stranded breaks is a consistent worry for therapeutic applications. These DNA breaks are highly toxic (particularly in bacteria), and often lead to error prone repair via non-homologous end joining pathways. Cleave and repair is potentially the best known way to insert large segments of DNA, which is important for many scientific and industrial applications.

Additionally, base editors are an effort to avoid toxicity by enzymatically converting nucleotides from one to another. To data, cytosine can be converted to thymine and adenine can be converted to guanine. Base editors have a major advantage over other techniques in that they are relatively efficient, and do not inherently require DNA breaks. However, base editors can only change a few nucleotides at a time within a small editing window, and other nucleotides can be inserted non-specifically. The restraints on the types of edits in particular means that base editors are only effective for a subset of applications, therapeutic or industrial.

Prime editors have only recently been described. Based on this work, it seems that prime editors are relatively efficient, and they have a major advantage in that they use a very small repair template which is encoded on the backbone of the Cas9 single guide RNA. While touted as a "double-strand break free" technique, efficient prime editing still involves nicking both strands of DNA in relatively close (<200 bp) proximity to achieve efficient editing. This dual nicking is only moderately less toxic than the 'cleave and repair' approach. Error-prone insertions and deletions still occur in mammalian cells as a result of dual nicking. It is unclear to what degree prime editors will function in prokaryotes. It also unclear whether any mutagenic side-affects might occur in their application, though their CRISPR-dependent off-target activity is muted.

Unlike the above technologies, gap editors of the present disclosure exhibit minimal toxic effects, which has important therapeutic implications. Low toxicity typically indicates a low rate of undesired mutations, DNA insertions or DNA re-arrangements, as well as loss of viability. Original CRISPR-Cas genome editing technologies relying on DNA cleavage and subsequent repair are especially vulnerable to DNA re-arrangements, multiple unintended DNA insertions, and toxic side-effects of DNA cleavage. Also, multiplex engineering is commonly hampered by the toxicity. An exemplary comparison of these technologies is provided in Table 1 below.

TABLE 1

| | Cleave & Repair | Base Editors | Primer Editors | Gap Editors |
|---|---|---|---|---|
| Avoiding Indels | + | +++ | + | +++ |
| 1-2 nt edits | +++ | +++ | +++ | +++ |
| Large Insertions | ++ | − | − | ++? |
| In vivo editing | + | ++? | ++? | ? |
| High-throughput | + | + | +++ | +++ |
| Multiplex | + | ++ | + | ++ |
| Non-mutagenic | ++ | − | ? | ++? |
| Toxicity | − | − | +? | +++? |
| Non-growing cells | − | + | ++ | ? |
| Targeting Scope | ++ | + | +++ | +++ |

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Correlated to" as used herein refers to compared to.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoiso-cytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inos-ine, N6-isopentenyladenine, 1-methyladenine, 1-methylp-seudouracil, 1-methylguanine, 1-methylinosine, 2,2-dimeth-ylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-manno-sylqueosine, 5'-methoxycarbonylmethyluracil, 5-methoxyu-racil, 2-methylthio-N6-isopentenyl adenine, uracil-5-oxy-acetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methylu-racil, N-uracil-5-oxyacetic acid methylester, uracil-5-oxy-acetic acid, pseudouracil, queosine, 2-thiocytosine, and 2,6-diaminopurine.

The term "gene" refers to a nucleic acid (e.g., DNA) sequence that comprises coding sequences for the produc-tion of a polypeptide, precursor, or RNA (e.g., rRNA, tRNA, sRNA, microRNA, lincRNA). The polypeptide can be encoded by a full-length coding sequence or by any portion of the coding sequence so long as the desired activity or functional properties (e.g., enzymatic activity, ligand bind-ing, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the mes-senger RNA (mRNA) transcript. The mRNA functions dur-ing translation to specify the sequence or order of amino acids in a nascent polypeptide.

As used herein, the term "heterologous gene" refers to a gene that is not in its natural environment. For example, a heterologous gene includes a gene from one species intro-duced into another species. A heterologous gene also includes a gene native to an organism that has been altered in some way (e.g., mutated, added in multiple copies, linked to non-native regulatory sequences, etc.). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligo-nucleotides are typically less than about 300 residues long (e.g., between 15 and 100), however, as used herein, the term is also intended to encompass longer polynucleotide chains. Oligonucleotides are often referred to by their length. For example, a 24-residue oligonucleotide is referred to as a "24-mer." Oligonucleotides can form secondary and tertiary structures by self-hybridizing or by hybridizing to other polynucleotides. Such structures can include, but are not limited to, duplexes, hairpins, cruciforms, bends, and tri-plexes.

The term "homology" and "homologous" refers to a degree of identity. There may be partial homology or com-plete homology. A partially homologous sequence is one that is less than 100% identical to another sequence.

As used herein, the terms "complementary" or "comple-mentarity" are used in reference to polynucleotides (e.g., a sequence of nucleotides such as an oligonucleotide or a target nucleic acid) related by the base-pairing rules. For example, for the sequence "5'-A-G-T-3'" is complementary to the sequence "3'-T-C-A-S'." Complementarity may be "partial," in which only some of the nucleic acids' bases are matched according to the base pairing rules. Or there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

In some contexts, the term "complementarity" and related terms (e.g., "complementary", "complement") refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. The percentage complementarity need not be calculated over the entire length of a nucleic acid sequence. The percentage of complementarity may be limited to a specific region of which the nucleic acid sequences that are base-paired, e.g., starting from a first base-paired nucleotide and ending at a last base-paired nucleotide. The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mis-matched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Thus, in some embodiments, "complementary" refers to a first nucleobase sequence that is at least 60%, 65%, 70%, 75%, 80%, 85%, 90%, 95%, 97%, 98%, or 99% identical to the complement of a second nucleobase sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases, or that the two sequences hybridize under stringent hybridization conditions. "Fully complementary" means each nucleobase of a first nucleic acid is capable of pairing with each nucleobase at a corresponding position in a second nucleic acid. For example, in certain embodiments, an oligonucleotide wherein each nucleobase has complementarity to a nucleic acid has a nucleobase sequence that is identical to the complement of the nucleic acid over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more nucleobases.

As used herein, a "double-stranded nucleic acid" may be a portion of a nucleic acid, a region of a longer nucleic acid, or an entire nucleic acid. A "double-stranded nucleic acid" may be, e.g., without limitation, a double-stranded DNA, a double-stranded RNA, a double-stranded DNA/RNA hybrid, etc. A single-stranded nucleic acid having secondary structure (e.g., base-paired secondary structure) and/or higher order structure comprises a "double-stranded nucleic acid". For example, triplex structures are considered to be "double-stranded". In some embodiments, any base-paired nucleic acid is a "double-stranded nucleic acid"

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

2. Gap Editors

Embodiments of the present disclosure include compositions, systems, and methods for targeted editing of a nucleic acid. In accordance with these embodiments, the present disclosure provides gap editors and gap editor complexes that generally include a DNA-recognition domain and a DNA-modifying domain. As described further in the Examples provided herein, gap editors and gap editor complexes facilitate programmable DNA targeting with a DNA-recognition domain that is functionally coupled to a DNA-modifying domain to drive genome editing via homology-directed gap repair. In some embodiments, the DNA-modifying domain introduces abasic sites in a target nucleic acid (e.g., oxidized nucleotides, nucleotide dimers, or other "damaged" nucleotides for the purposes of genome editing). In some embodiments, the DNA-recognition domain facilitates the targeting of the gap editor to a site in a nucleic acid. Targeting of gap editors in a specific orientation generates persistent DNA gaps, thereby improving gap editor efficiency.

In some embodiments, the DNA-recognition domain and the DNA-modifying domain are functionally coupled. Functionally coupled includes any means for integrating the DNA-recognition domain and the DNA-modifying domain at a specific target site for the purposes of functioning as genome editors. In some embodiments, "functionally coupled," includes but is not limited to polypeptide fusions, peptide tags, peptide linkers, RNA tags, and any combinations thereof. For example, a gap editor or gap editor complex can include a DNA-recognition domain that is fused to a DNA-modifying domain (e.g., a fusion polypeptide). The DNA-recognition domain of the gap editor fusion protein recognizes a specific site (e.g., nucleic acid sequence) in a target nucleic acid, and the DNA-modifying domain is then capable of modifying one or more nucleic acids in or around the target site to facilitate genome editing.

In some embodiments, the DNA-recognition domain and the DNA-modifying domain do not comprise a fusion polypeptide (e.g., do not form a single fusion polypeptide or protein). In some embodiments, the DNA-modifying domain is recruited to the gap editor or gap editor complex by the DNA-recognition domain. For example, the DNA-recognition domain of the gap editor can recruit the DNA-modifying domain via a protein-protein interaction. In some embodiments, this recruitment is facilitated by a tag or linker that serves to recruit and functionally couple the DNA-modifying domain to the DNA-recognition domain at a specific site of a target nucleic acid. Other means for recruiting and functionally coupling the DNA-modifying domain to the DNA-recognition domain based on protein-protein interactions can also be used, including but not limited to, antigen-antibody interactions (e.g., the DNA-modifying domain fused to an antigen binding domain and the DNA-recognition domain fused to the corresponding antigen), protein tags (e.g., a streptavidin-biotin interaction), a peptide and single chain variable antibody fragment, a split-protein system, or any ligand-receptor interaction.

In other embodiments, the DNA-modifying domain is recruited to the gap editor or gap editor complex by an interaction with a nucleic acid. For example, a guide RNA molecule that interacts with the DNA-recognition domain to bind a site in a target nucleic acid can include a sequence and/or structure that binds the DNA-modifying domain (e.g., a scaffold domain). In some embodiments, the sequence and/or structure on the guide RNA includes domains that are recognized by RNA binding proteins. In some embodiments, the DNA-modifying domain is fused to an RNA-binding protein that is recruited to the gap editor or gap editor complex via binding to the domain on the guide RNA. Other means for recruiting and functionally coupling the DNA-modifying domain to the DNA-recognition domain based on RNA-binding interactions can also be used. In some embodiments, the guide RNA is extended to encode an RNA aptamer that recognizes different proteins or protein domains, such as the MS2 coat protein, Tat, or Rev. The recognized protein or protein domain is then fused to the DNA-modifying domain. The guide RNA can encode multiple copies of the same protein-binding domain or different protein-binding domains. These protein-binding domains can be incorporated into different parts of the gRNA, such as through the loop of the gRNA or sgRNA or at the 3' end of the sgRNA.

In accordance with these embodiments, the DNA-recognition domains of the gap editors or gap editor complexes of the present disclosure include use of a sequence-specific nucleic acid binding component (e.g., molecule, biomolecule, or complex of one or more molecules and/or biomolecules) to target a specific nucleic acid target site. In some embodiments, the DNA-recognition domain includes at least one Cas protein or fragment thereof lacking nuclease or deoxyribonuclease activity. In some embodiments, the DNA-recognition domain comprises a complex of Cas proteins lacking nuclease or deoxyribonuclease activity. In some embodiments, the DNA-recognition domain includes at least one Cas protein or a complex of Cas proteins that exhibit nickase activity, including but not limited to, a Cas9 or a Cas12a with nickase activity. In some embodiments, the DNA-recognition domain induces a single-stranded break in the DNA target strand (e.g., via nickase activity), and the DNA-modifying domain adds an abasic site to at least one nucleotide in the DNA strand complementary to the DNA target sequence.

In some embodiments, the Cas protein or Cas protein complex comprises a Type I Cascade, a Type II Cas9, a Type IV effector module, a Type V Cas12, and combinations thereof. Cascade is a set of Cas proteins that form a stable complex in different proportions with the guide RNA. The gRNA is normally encoded within a CRISPR array, where the Cas6 protein of the complex cleaves a hairpin in the transcribed repeat. The other proteins then form around the freed RNA. The fully-formed complex binds target DNA flanked by a protospacer-adjacent motif (PAM) encoded on the 5' end of the non-target strand. Upon target recognition, the complex then recruits the Type I endonuclease Cas3 to nick and processively degrade the non-target strand in the 3'-to-5' direction, although the complex will stably bind target DNA in the absence of Cas3. The specific number and stoichiometry of the proteins in Cascade varies between CRISPR-Cas sub-types, such as Cas8c(1):Cas5c(1):Cas7(7) for the I-C sub-type and Cse1(1):Cse2(2):Cas5e(1):Cas7(6):Cas6e(1) for the I-E sub-type. Furthermore, these proteins can be fused to recapitulate the complex with fewer expressed polypeptides, and the Cas6 protein is dispensable if the guide RNA is expressed as a processed CRISPR RNA. Varying the length of the guide sequence within the gRNA can further alter the protein stoichiometry of Cascade and can change the length of the R-loop and displaced DNA strand. Cas9 is a single-effector nuclease that binds target DNA with a PAM encoded on the 3' end of the non-target strand. Bound DNA is then nicked on opposite strands through the HNH and RuvC domains of Cas9, resulting in a double-stranded break. The gRNA utilized by Cas9 is normally encoded with a CRISPR array, where a transactivating crRNA (tracrRNA) pairs with the transcribed repeat, and the RNA duplex is cleaved by the endoribonuclease RNase III. The resulting processed crRNA:tracrRNA duplex is bound by Cas9 and directs DNA targeting. The crRNA:tracrRNA duplex can be fused to form a single guide RNA (sgRNA). Cas12 represents a diverse family of Cas nucleases designated by their sub-type (e.g. Cas12a, Cas12e) and have been given alternative names such as Cpf1, C2c1, CasX, or Cas14a. Cas12 nucleases target DNA with a PAM encoded on the 5' end of the non-target strand, with the nuclease's RuvC domain nicking the both the target and non-target stranded to create a staggered double-stranded break with a 5' overhang. The gRNA is encoded within a CRISPR array and can be processed from the transcribed CRISPR array through one of two mechanisms depending on the nuclease: cleavage of a hairpin within the repeat by a riboendonucleolytic domain with the Cas12 nuclease (e.g. Cas12a), or pairing of the transcribed repeat with a tracrRNA that is subsequently cleaved by RNase III. As a result, the gRNA can be readily expressed in its processed form when the nuclease alone is responsible for crRNA processing, the gRNA can be expressed as an sgRNA when a tracrRNA is involved in crRNA processing.

In some embodiments, the DNA-recognition domain comprises a deoxyribonuclease-inactivated Cas9 ("dCas9"), which can be generated by introducing deactivating mutations within the HNH domain and the RuvC domain of the protein. In some embodiments, the DNA-recognition domain comprises a deoxyribonuclease-inactivated Cas12a ("dCas12a"), which can be generated by introducing deactivating mutations within at least one of the RuvC domains, such as RuvC-I. Alternatively, a guide RNA that is truncated on the PAM-distal end or contains mismatches with the target can allow DNA binding but not DNA nicking or cleavage by an otherwise catalytically active Cas nuclease.

In some embodiments, the DNA-modifying domain catalyzes formation of the at least one abasic site in the DNA target sequence. In some embodiments, the DNA-modifying domain comprises glycosylase activity, deaminase activity, oxidase activity, nucleosidase activity, hydroxylase, hydrolase activity, and combinations thereof. In some embodiments, the DNA-modifying domain comprises a cytidine deaminase, a guanine deaminase, an adenine deaminase, a xanthine oxidase, a uracil DNA glycosylase, a cytidine DNA glycosylase, a thymidine DNA glycosylase, a 3-methyladenine DNA glycosylase, or a thymidine hydroxylase. A DNA-modifying domain comprised of a glycosylase will directly excise DNA targeted by the DNA-recognition domain, resulting in an abasic site. Other DNA modifying enzymes, including deaminases, hydroxylases, oxidases, nucleosidases, and hydrolases modify DNA in such a way that natively expressed cellular factors will excise the modified DNA, producing an abasic site and thus can be used as part of gap editors.

As described further in the Examples provided herein, the gap editor and gap editor complexes of the present disclosure include a DNA-recognition domain and a DNA-modifying domain that are functionally coupled. Exemplary embodiments of gap editors are provided as SEQ ID NO: 1 (rAPOBEC1-dCas9 deaminase gap editor), SEQ ID NO: 2

(Cytosine DNA glycosylase-dCas9), SEQ ID NO: 3 (MAG1 glycosylase-dCas9), SEQ ID NO: 4 (hAAG glycosylase-dCas9).

Embodiments of the present disclosure also include gap editors and gap editor complexes that include at least one guide RNA molecule. In accordance with these embodiments, the guide RNA molecule comprises a handle sequence and a targeting sequence. The targeting sequence interacts with a sequence in the target nucleic acid, and the handle sequence facilitates binding of the gap editor or gap editor complex. As would be recognized by one of ordinary skill in the art based on the present disclosure, a single chimeric guide RNA (sgRNA) can mimic the structure of an annealed crRNA/tracrRNA; this type of guide RNA has become more widely used than crRNA/tracrRNA because the gRNA approach provides a simplified system with only two components (e.g., the Cas9 and the sgRNA). Thus, sequence-specific binding to a nucleic acid target can be guided by a natural dual-RNA complex (e.g., comprising a crRNA, a tracrRNA, and Cas9) or a chimeric single-guide RNA (e.g., a sgRNA and Cas9). (see, e.g., Jinek et al. (2012) "A Programmable Dual-RNA-Guided DNA Endonuclease in Adaptive Bacterial Immunity" Science 337:816-821). As used herein, the targeting region of a crRNA (2-RNA system) or a sgRNA (single guide system) is referred to as the "guide RNA" (gRNA). Multiple gRNAs can be further expressed using CRISPR arrays that naturally encode the crRNA utilized by the nucleases. The gRNAs can also be expressed separately by being operably linked to a promoter and terminator. The gRNAs can also be fused in a single transcript by including intervening RNA cleavages sites, such as ribozymes or sites recognized by RNA-cleaving enzymes such as RNase P, RNase Z, RNase III, or Csy4.

In some embodiments, the compositions and systems of the present disclosure comprise one guide RNA, which is sufficient to facilitate genome editing (FIG. 3B). In some embodiments, the compositions and systems include at least a first and a second guide RNA, which bind distinct sites in a target nucleic acid. In some embodiments, the first guide RNA is complementary to a first DNA target sequence and the second guide RNA is complementary to a second DNA target sequence. In some embodiments, the first and the second DNA target sequences are on opposite strands of a double-stranded DNA molecule. In accordance with these embodiments, at least one abasic site is generated in the DNA strand complementary to the DNA target sequence. In other embodiments, the at least one abasic site is generated outside the DNA target sequence.

In some embodiments, the gap editor complex of the present disclosure induces formation of at least one abasic site in a DNA target sequence on a strand of a double-stranded DNA molecule. In some embodiments, the gap editor complex of the present disclosure induces formation of at least two abasic sites in two distinct DNA target sequences on opposite strands of a double-stranded DNA molecule. In accordance with these embodiments, the presence of a donor nucleic acid template facilitates homology-directed gap recombination or oligonucleotide-mediated recombination, which includes the donor nucleic acid template or a fragment thereof being recombined into the double-stranded target DNA molecule. The donor nucleic acid template can be single-stranded or double-stranded. The donor nucleic acid may be delivered as plasmid or linear DNA. A donor nucleic acid may also be generated in vivo from a template ribonucleic acid by a reverse transcriptase. In other implementations, the donor nucleic acid may itself be a ribonucleic acid. The donor nucleic acid can also contain chemical modifications.

In some embodiments, the compositions and systems of the present disclosure further comprise a one gap editor accessory factor. In some embodiments, the at least one gap editor accessory factor includes a protein involved in DNA modification or repair (see, e.g., FIG. 5). In some embodiments, the gap editor accessory factor can be recruited to the gap editor complex via interaction with the DNA-modifying domain, the DNA-recognition domain, and/or the at least one guide RNA (as described above). In some embodiments, the at least one gap editor accessory factor comprises Rap, lambda Beta, lambda Orf, RecT, a reverse transcriptase (e.g., MMLV, Ec86), a deactivated or dominant-negative abasic site exonuclease (e.g., Exonuclease III, APE1), YedK, HMCES, ExoI, PRIMPOL, RecJ, RECQ1, Uracil DNA glycosylase, and any combinations thereof.

In some embodiments, the accessory factors may be mutated or engineered. For example, YedK and/or RecQ can be mutated in a manner that renders them catalytically inactive. The Rap protein serves to resolve holliday junction intermediates during homologous recombination, stimulating recombination. YedK and HMCES bind to abasic sites and protect them from apurinic/apyrimidinic endonucleases and translesion polymerases. Additionally, a de-activated AP endonuclease, such as but not limited to, Exonuclease III or APE1 from eukaryotes can be used to bind to and protect an abasic site. Typically, these AP endonucleases aid in the removal of abasic sites; however, adding a mutation that renders them catalytically inactive produces an endonucleases that binds to, but does not process, the abasic site. Through this binding action, a deactivated nuclease acts as an abasic site protector. In some embodiments, the accessory factor can include an exonuclease, such as but not limited to, ExoI and RecJ. ExoI and RecJ, as well as other exonucleases, are involved in increasing the sizes of DNA gaps by digesting DNA. In some embodiments, the accessory factor can include a helicase, such as but not limited to, RecQ. RecQ and other helicases are involved in formation of long DNA gaps, replication fork decision-making upon encountering a DNA lesion such as an abasic site, and regulation of recombinase filaments formed by RecA and Rad51.

In some embodiments, the at least one gap editor accessory factor comprises a protein or RNA-directing deoxyribonuclease having nuclease activity, wherein the deoxyribonuclease activity counter-selects against cells in which template-mediated editing of the DNA target has not occurred. In some embodiments, the accessory factor is a separate Cas nuclease directed to cleave a site that is edited by the gap editor. The unedited site but not the edited site can be effectively targeted by this nuclease, thereby selecting for edited cells. Edits known to disrupt targeting can be present within the PAM and/or the target sequence. The accessory factor can be the same core nuclease used for the gap editor, such as using dCas9 for the gap editor and Cas9 for counter-selection, with this setup allowing the use of the same gRNAs for editing as well as counter-selection. Alternatively, the accessory factor can be an entirely different Cas nuclease, such as using dCas9 for the gap editor and Cas12a for counter-selection. In other embodiments, gRNAs with truncated guides and/or guides containing mismatches to the target are combined with a gap editor relying on a catalytically-active Cas nuclease. These gRNAs then direct DNA binding but not cleavage, facilitating gap editing. Different gRNAs with guides that are full-length and/or mostly or perfectly match the target are then expressed to direct the gap editor to cleave unedited targets.

As would be recognized by one of ordinary skill in the art based on the present disclosure, methods for delivering gap editors and gap editor complexes into a cell include any currently known methods and systems for delivering polynucleotides and/or polypeptides/proteins. For example, gap editors and gap editor complexes can be delivered using plasmid DNA, ssDNA, RNA, or other means for delivering polynucleotide molecules, including but not limited to, lipid-based delivery systems (e.g., using cationic lipids), conjugation from a donor cell, viral/bacteriophage-based delivery systems, and chemical-based systems (e.g., calcium phosphate precipitation, DEAE-dextran, polybrene). In some embodiments, the delivery system can include mechanical and/or electrical devices and methods for delivering the gap editors and gap editor complexes of the present disclosure as polynucleotides and/or as polypeptides/proteins (or any combinations thereof). In some embodiments, gap editors and gap editor complexes are delivered using a gene gun (e.g., bombardment and *Agrobacterium* transformation as used for plant cells), and electroporation-based methods, as well as any other physical methods (e.g., mechanical, electrical, thermal, optical, chemical stimulation, and the like) that use membrane disruption as a means for delivering polynucleotides and polypeptides/proteins (see, e.g., Sun et al., Recent advances in micro/nanoscale intracellular delivery, Nanotechnology and Precision Engineering 3, 18 (2020)). In accordance with these embodiments, the gap editors and gap editor complexes and compositions of the present disclosure can be delivered (e.g., in situ) in a manner that is suitable for genetically modifying a plurality of target cells (e.g., a microbial community or microbiome), with significantly reduced cellular toxicity, as described further herein.

3. Kits, Systems, and Methods

Embodiments of the present disclosure also include kits and systems for targeted editing of a nucleic acid. In accordance with these embodiments, the kits and systems include a gap editor or gap editor complex. As described above, gap editors and gap editor complexes include a DNA-recognition domain and a DNA-modifying domain, and at least one guide RNA molecule. The gap editor complex binds a nucleic acid target sequence and induces formation of at least one abasic site in or around the nucleic acid target. As would be recognized by one of ordinary skill based on the present disclosure, the kits and systems can also include one or more of the other components of the gene editing compositions described herein (e.g., gap editor accessory factors). In some embodiments of the kit, the composition further comprises a donor nucleic acid template. In some embodiments of the kit, the presence of the donor nucleic acid template facilitates homology-directed gap repair and/or recombination.

In some embodiments of the kit, the DNA-recognition domain comprises at least one Cas protein or fragment thereof lacking deoxyribonuclease activity. In some embodiments of the kit, the DNA-recognition domain comprises at least one Cas protein or fragment thereof having nickase activity. In some embodiments, the Cas protein or Cas protein complex comprises a Type I Cascade, a Type II Cas9, a Type IV effector module, a Type V Cas12, and combinations thereof. In some embodiments of the kit, the DNA-recognition domain and the DNA-modifying domain are functionally coupled. In some embodiments of the kit, the DNA-recognition domain induces a single-stranded break in the DNA target strand, and the DNA-modifying domain adds an abasic site to at least one nucleotide in the DNA strand complementary to the DNA target sequence.

Embodiments of the present disclosure also include methods for targeted editing of a nucleic acid. In accordance with these embodiments, the methods include introducing any of the components of the gene editing compositions described herein, and assessing the cell for presence of a desired genetic alteration using techniques known in the art. In some embodiments of the method, the components include gap editors and gap editor complexes comprising a DNA-recognition domain and a DNA-modifying domain, at least one guide RNA molecule, and a donor nucleic acid template. In some embodiments, one or more gap editor accessory factors can also be included. One or more of these factors can be introduced into a cell or organism as a polypeptide(s), mRNA(s), and/or DNA expression construct(s), or any combination thereof, by means known in the art. As would be recognized by one of ordinary skill in the art based on the present disclosure, the gap editor compositions, systems, and methods can be used to facilitate the editing of whole organisms, including but not limited to, humans, plants, livestock, and the like.

In some embodiments of the method, at least one of these components are introduced into the cell as part of a gene drive system. In a gene drive system, all or some of genome editing components such as the DNA-recognition domain, DNA-modifying domain, gRNA, and accessory factors are encoded within the donor nucleic acid sequence present in one copy of a chromosome. The gRNA directs the DNA-modifying domain to the sister chromosome in the region where the donor nucleic acid sequence would reside. Upon targeting by the gap editor proteins or complexes, the donor nucleic acid (which also encodes the gap editor system) is copied over to a new chromosome. Thus, the gap editor system becomes self-propagating, efficiently forming homozygously edited organisms. Example organisms in which gene drives can be implemented include fungi, flatworms, mosquitos, and mice.

In some embodiments, the compositions, systems, and methods of the present disclosure include one or more components that enhance or improve one or more aspects of gene editing. In some embodiments, improving or enhancing one or more aspects of gene editing includes the use of a gap editor accessory factor(s), as described above. In some embodiments, methods that enhance or improve one or more aspects of gene editing include reducing or attenuating nuclease activity in a cell in which genome editing is desired. Reducing nuclease activity in a cell can lead to enhanced or improved editing frequency and/or efficiency. In some embodiments, reducing nuclease activity in a cell includes reducing activity of an endogenous AP endonuclease (e.g., xthA) by any means known in the art. In some embodiments, nuclease activity in a cell can be reduced via genetic means and/or by pharmacological means (e.g., treatment with endonuclease inhibitors including but not limited to AJAY-4, CRT0044876, aurintricarboxylic acid, 6-hydroxy-DL-DOPA, Reactive Blue 2, myricetin, mitoxantrone, methyl-3,4-dephostatin, thiolactomycin, and (2E)-3-[5-(2,3-dimethoxy-6-methyl-1,4-benzoquinoyl)]-2-nonyl-2-propenoic acid (E3330)).

Embodiments of the compositions, systems, and methods provided herein are used to edit the genome of a cell. The cell can be a prokaryotic cell, a eukaryotic cell, or a plant cell. In some embodiments, the cell is a mammalian cell. The present disclosure also provides an isolated cell comprising any of the components or systems described herein. Exemplary cells can include those that can be easily and reliably grown, have reasonably fast growth rates, have well characterized expression systems, and can be transformed or transfected easily and efficiently. Examples of suitable prokaryotic cells include, but are not limited to, cells from the genera *Bacillus* (such as *Bacillus subtilis* and *Bacillus brevis*), Clostridia (such as *Clostridium difficile* or *Clostridium autoethanogenum*), *Escherichia* (such as *E. coli*), Lactobacilli, *Klebsiella, Myxobacteria, Pseudomonas, Streptomyces, Salmonella, Vibrio* (such as *Vibrio cholerae* or *Vibrio nutrifaciens*) and Envinia. Suitable eukaryotic cells are known in the art and include, for example, yeast cells, insect cells, and mammalian cells. Examples of suitable yeast cells include those from the genera *Kluyveromyces, Pichia, Rhino-sporidium, Saccharomyces*, and *Schizosaccharomyces*. Exemplary insect cells include Sf-9 and HIS (Invitrogen, Carlsbad, Calif.) and are described in, for example, Kitts et al., Biotechniques, 14: 810-817 (1993); Lucklow, *Curr. Opin. Biotechnol.*, 4: 564-572 (1993); and Lucklow et al., *J. Virol.*, 67: 4566-4579 (1993).

In some embodiments, the cell can also be a cell that is used for therapeutic purposes. The cell can be a mammalian cell, and in some embodiments, the cell is a human cell. A number of suitable mammalian and human cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., Proc. Natl. Acad. Sci. USA, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian cells include primate, rodent, and human cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, HEK, A549, HepG2, mouse L-929 cells, and BHK or HaK hamster cell lines. Methods for selecting suitable cells and methods for transformation, culture, amplification, screening, and purification of cells are known in the art. Examples of suitable plant cell lines are derived from plants such as *Arabidopsis* (such as the Landsberg erecta cell line), sugarcane, tomato, pea, rice, wheat, tobacco (such as the BY-2 cell line).

In accordance with the methods described above embodiments, the compositions and systems of the present disclosure can be used to edit a genome of a cell in a manner that reduces the degree of indel formation, chromosomal inversions, or DNA duplications. In some embodiments, the compositions, systems, and methods described herein reduce cell toxicity as compared to currently available methods, at least in part due to the lack of single or double-stranded breaks in the target nucleic acid. This aspect of the inventive subject matter of the present disclosure is an unexpected improvement over current technology.

4. Materials and Methods

Gap editing in *E. coli* at the lacZ gene was performed by first transforming the gRNA and nucleic acid donor into *E. coli* by electroporation and plated on LB agar plus the appropriate antibiotic(s). The resulting strain was next transformed with plasmids encoding the accessory factors if used. The resulting strain was further transformed with the gap editor-expressing plasmid and plated with appropriate antibiotic(s). The resulting colonies were picked and inoculated into 750 mL of liquid LB media in a deep well plate shaking at 900 rpm and 37° C. for 12 to 16 hours overnight. Overnight culture was serially diluted and 5 μL of each dilution for each sample was plated onto LB agar plates with antibiotic, IPTG, and x-gal. Gap editor expression was induced by diluting overnight culture 1:500 into 750 mL of liquid LB media with antibiotics, 1 mM IPTG and 33 mM arabinose and shaken at 900 rpm for 8 hours. If accessory factors were used, 125 ng/mL of anhydrotetracycline was added. After 8 hours, samples were removed for spot plating on LB agar with antibiotics, IPTG, and X-gal. Samples were further back diluted 1:500 into LB with antibiotics and inducers prior to culturing for an additional 16 hours. After 16 hours, samples were removed for spot plating on LB agar with antibiotics, IPTG, and X-gal. Plates were incubated at 37° C. overnight. The next day, white and blue colonies were counted to determine frequency of lacZ recombination and repair. Repair was confirmed by Sanger sequencing.

Gap editing in *E. coli* at the rpoB gene was performed by first transforming the gRNA and nucleic acid donor into SPC1195 by electroporation and plated on LB agar plus the appropriate antibiotic(s). The resulting strain was next transformed with plasmids encoding the accessory factors if used. The resulting strain was further transformed with the gap editor expressing plasmid and plated with appropriate antibiotic(s). The resulting colonies were picked and inoculated into 750 mL of liquid LB media in a deep well plate shaking at 900 rpm and 37° C. for 12 to 16 hours overnight. Overnight culture was serially diluted and 5 μL of each dilution for each sample was plated onto either LB agar plates with and without rifampicin to quantify the rate of genome editing, plus antibiotics for plasmid maintenance. Gap editor expression was induced by diluting overnight culture 1:500 into 750 mL of liquid LB media with antibiotics, 1 mM IPTG and 33 mM arabinose and shaken at 900 rpm for 8 hours. If accessory factors were used, 125 ng/mL of anhydrotetracycline was added. This culture was serially diluted and 5 μL of each dilution for each sample was plated onto either LB agar plates with and without rifampicin to quantify the rate of genome editing, plus antibiotics for plasmid maintenance. Samples were further back diluted 1:500 into LB with antibiotics and inducers prior to culturing for an additional 16 hours. After 16 hours, samples were removed for spot onto LB agar plates with and without rifampicin to quantify the rate of genome editing, plus antibiotics for plasmid maintenance. The rate of rifampicin resistance, and thus the rate of genome editing, was quantified as the fraction of CFU/mL counted from plates containing rifampicin divided by the CFU/mL counted from plates lacking rifampicin. Genome editing was confirmed by Sanger sequencing.

For genome editing in yeast, the gap editor plasmid was transformed into strains ISA608 and ISA609 and plated on CSM-Leu with 0.4% w/v glucose. The resulting strains were further transformed with the sgRNA and donor repair template plasmids and plated on CSM-Leu-Trp with 0.4% glucose and 0.2% raffinose. The resulting strains were inoculated into CSM-Leu-Trp with 2% w/v galactose to induce expression of the gap editor complex. These strains were cultured in deep well plates at 30 C, shaking at 900 rpm for 24 hours before being plated on either CSM-Leu-Trp or CSM-Leu-Trp-Ura. Genome editing frequency was calculated as the CFU/mL present on the plates lacking uracil divided by the CFU/mL on plates containing uracil.

TABLE 2

Figures 2A, 2B, 2C:
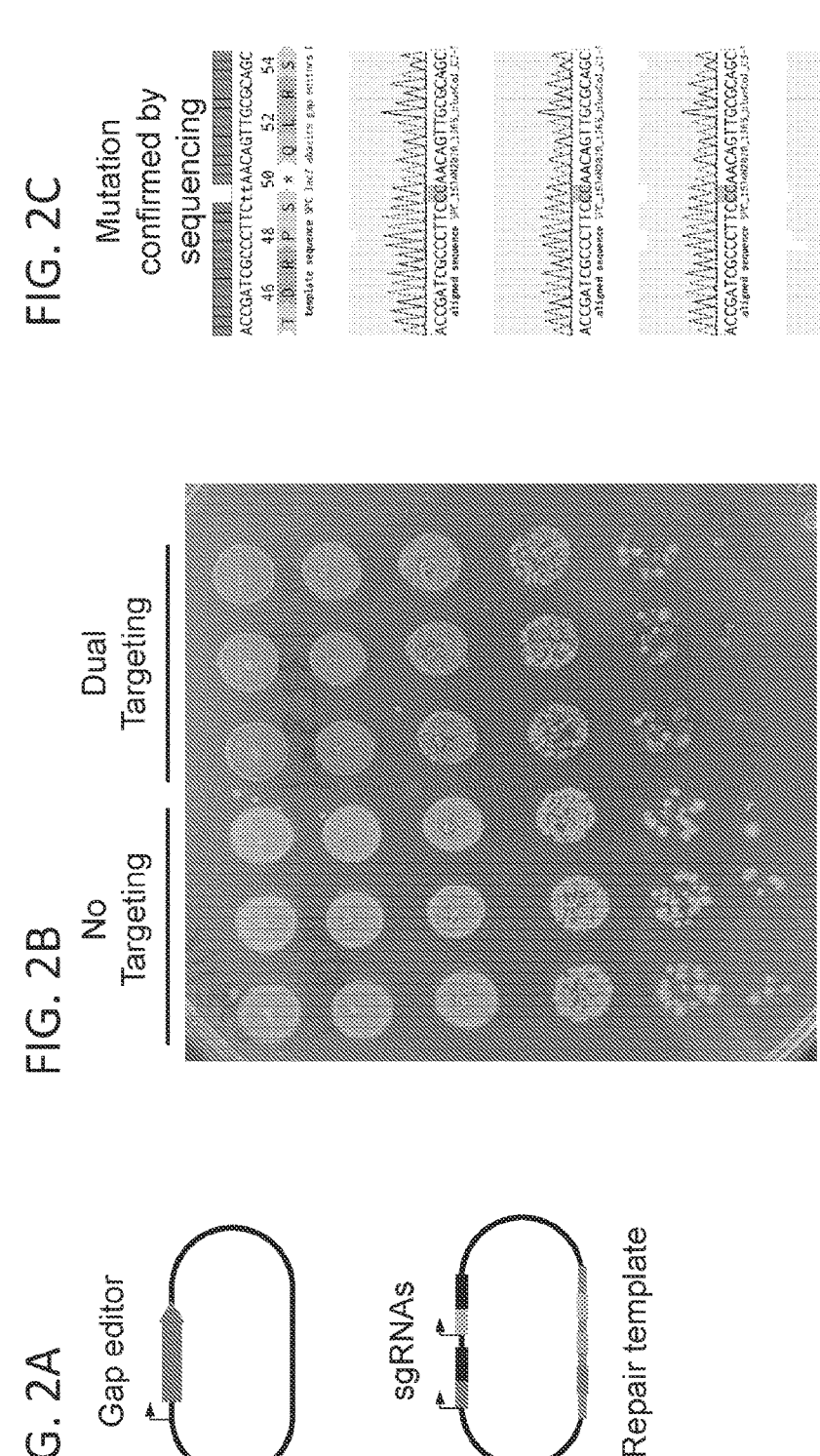
FIGS. 2A-2C include representative diagrams of plasmids used for genome editing (FIG. 2A) and representative results of experiments demonstrating that gap editor targeting leads to efficient and extensive genome editing after 24 hours of induction (FIG. 2B), with confirmation of gene repair by DNA sequencing (FIG. 2C).
Figure 3:
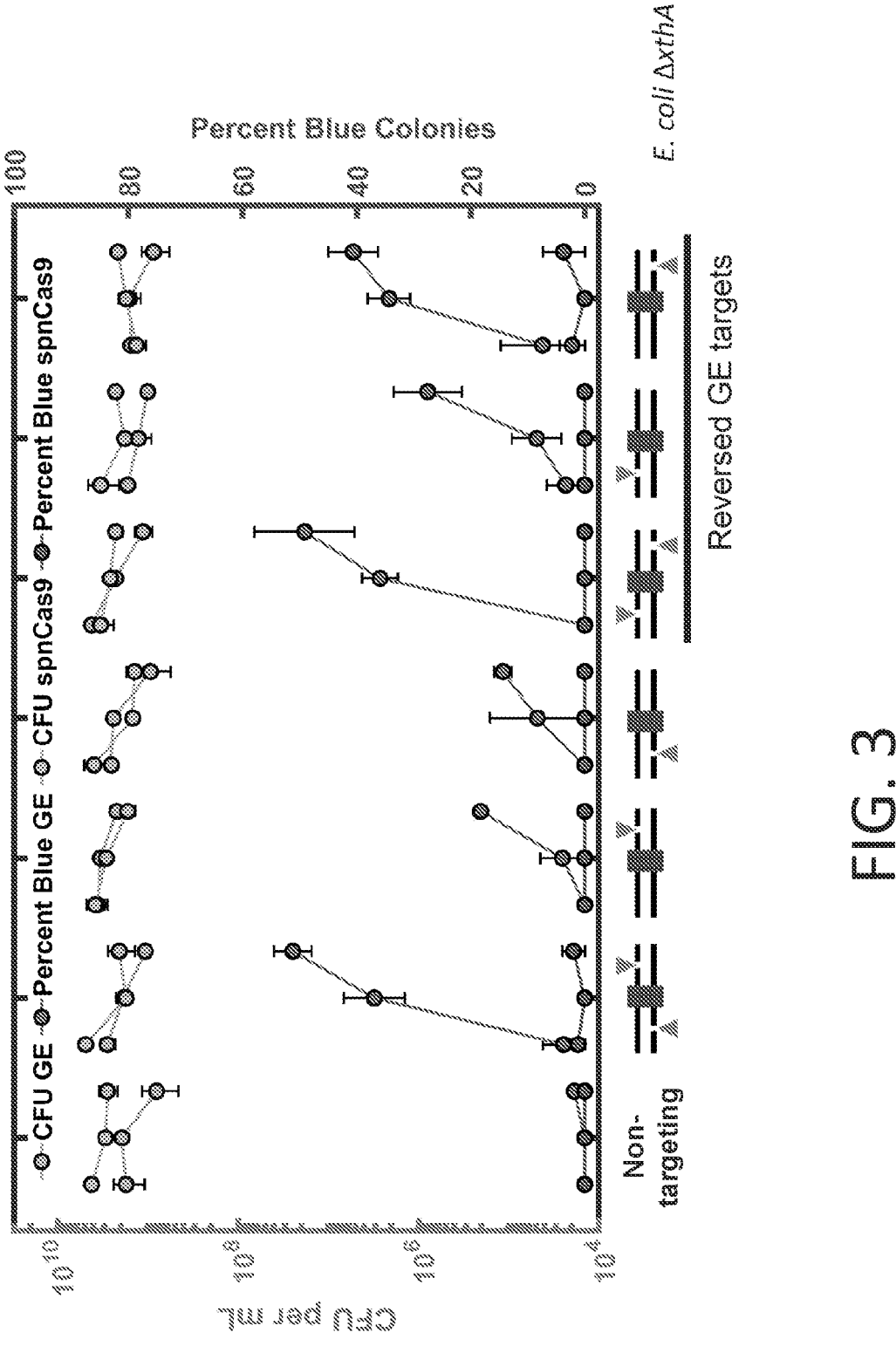
FIG. 3 includes representative results of experiments demonstrating that targeting a gap editor complex adjacent to the desired editing location produces editing (GE=gap editor) which far outperforms controls from an SpCas9 nickase (spnCas9) using identical sgRNAs and repair templates.
Figure 5A:
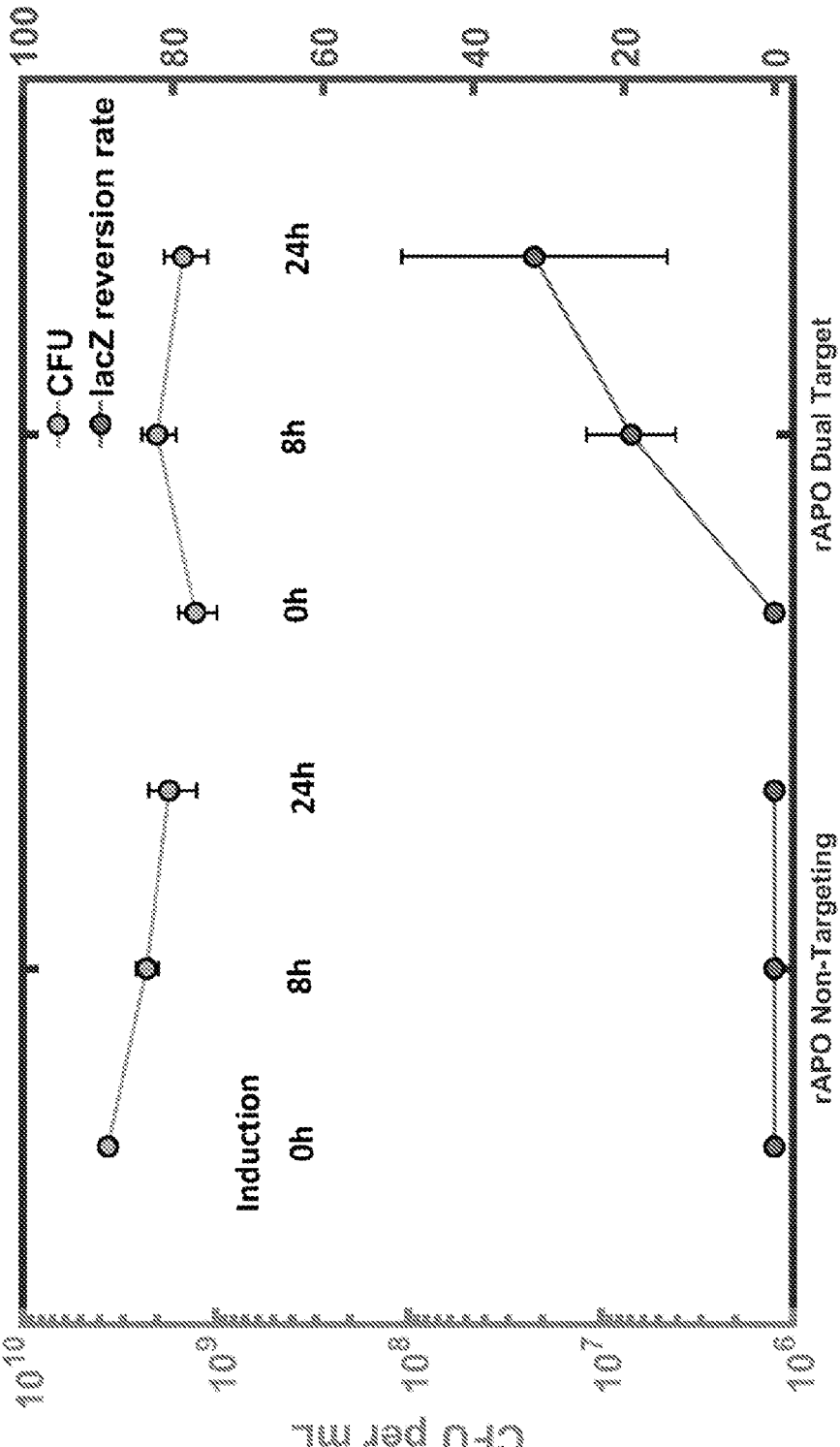
FIGS. 5A-5B include representative results of experiments demonstrating that targeting two genomic sites flanking the desired editing location triggers homologous recombination in *E. coli* without any significant decrease in viability (FIG. 5A).
Figure 5B:
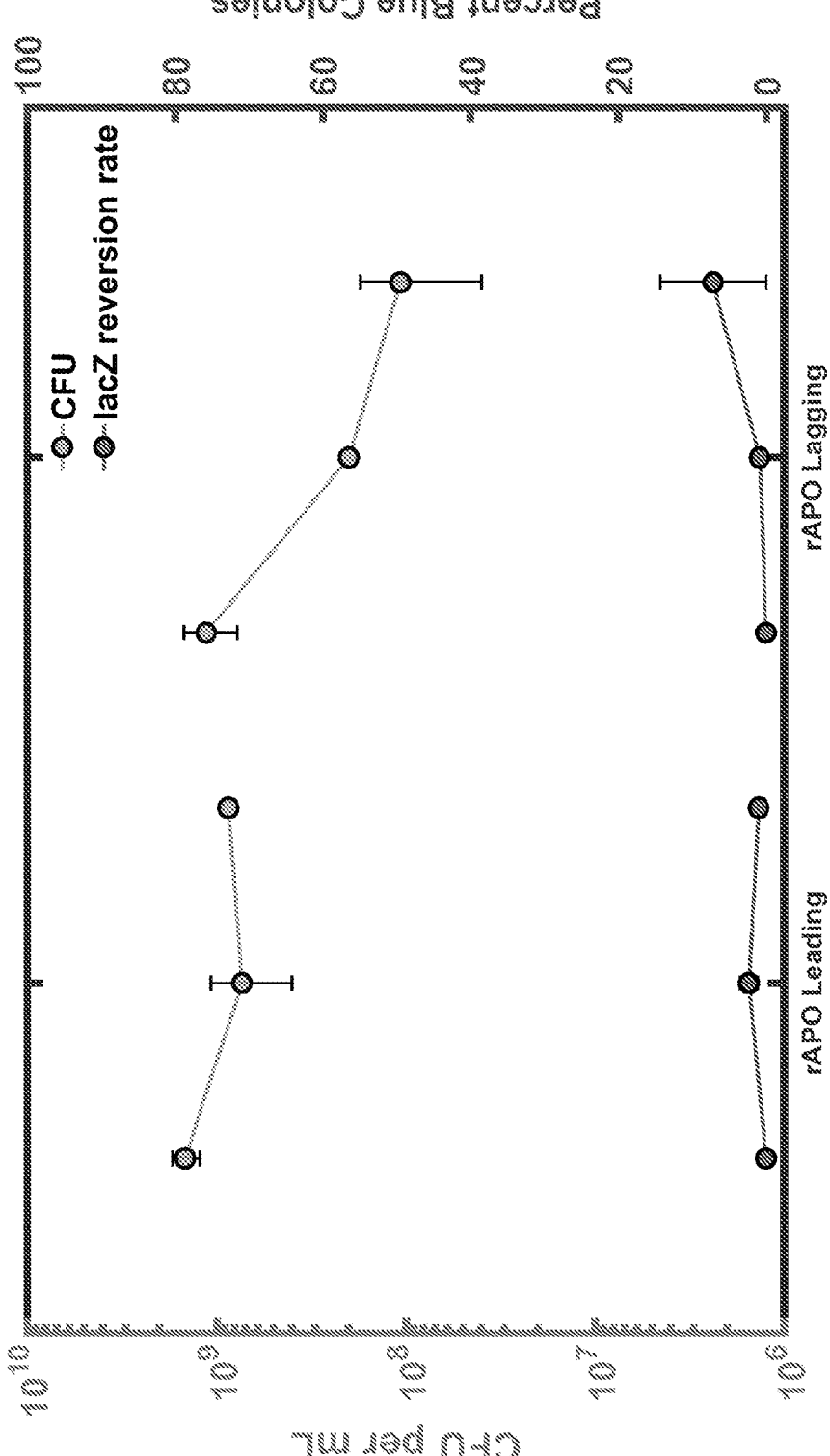
Figure 6:
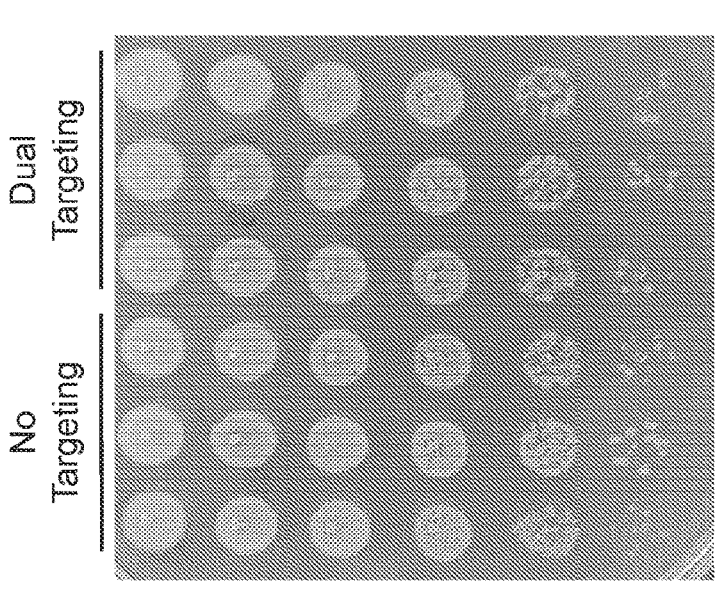
FIG. 6 includes representative results of experiments demonstrating that RecF is required for genome editing by a gap editor complex.
Figure 6:
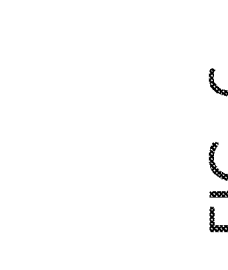
Figure 6:
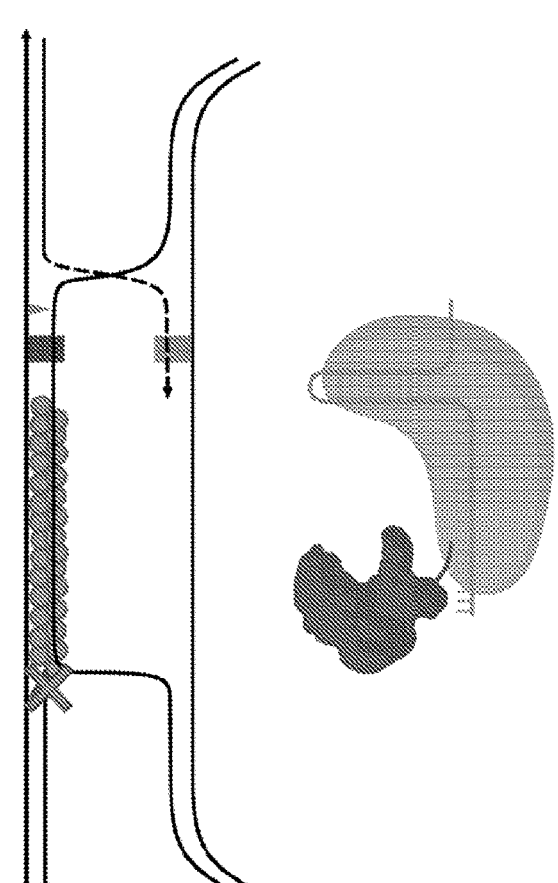
Figure 7:
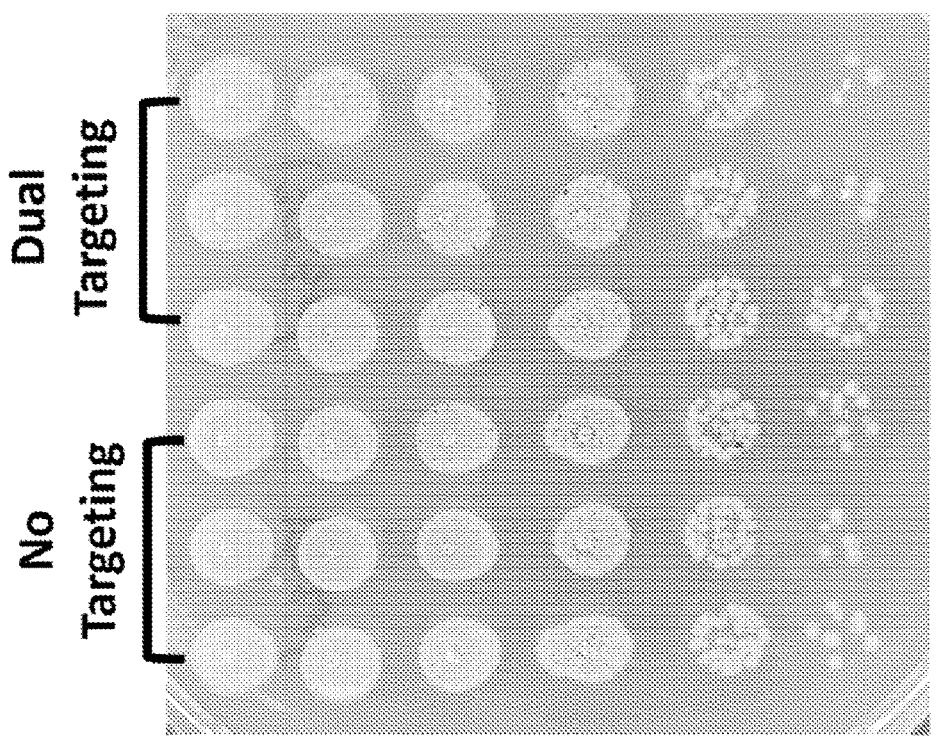
FIG. 7 includes representative results of experiments demonstrating that use of a typical base editor, which included a cytidine deaminase domain as well as a uracil glycosylase inhibitory domain (UGI), inhibited repair above a non-targeting control.
Figure 7:
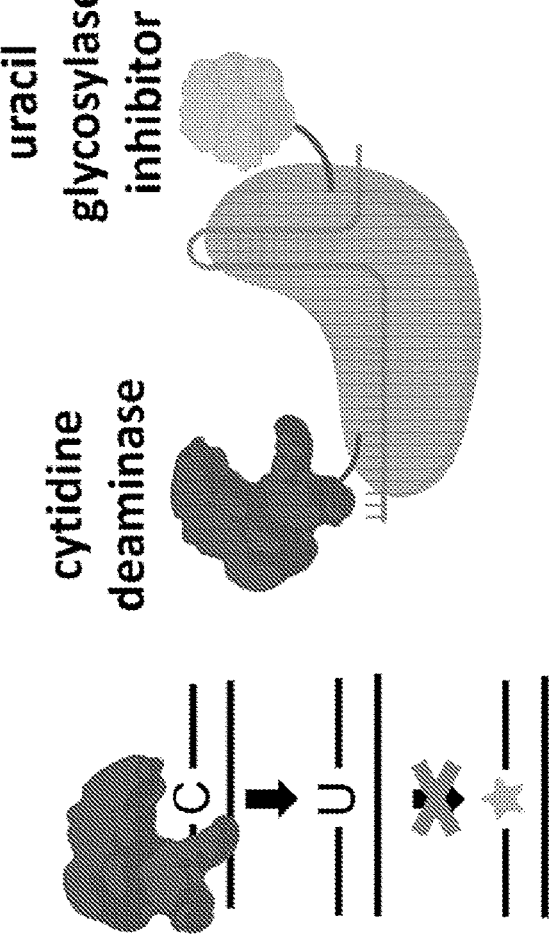
Figure 8:
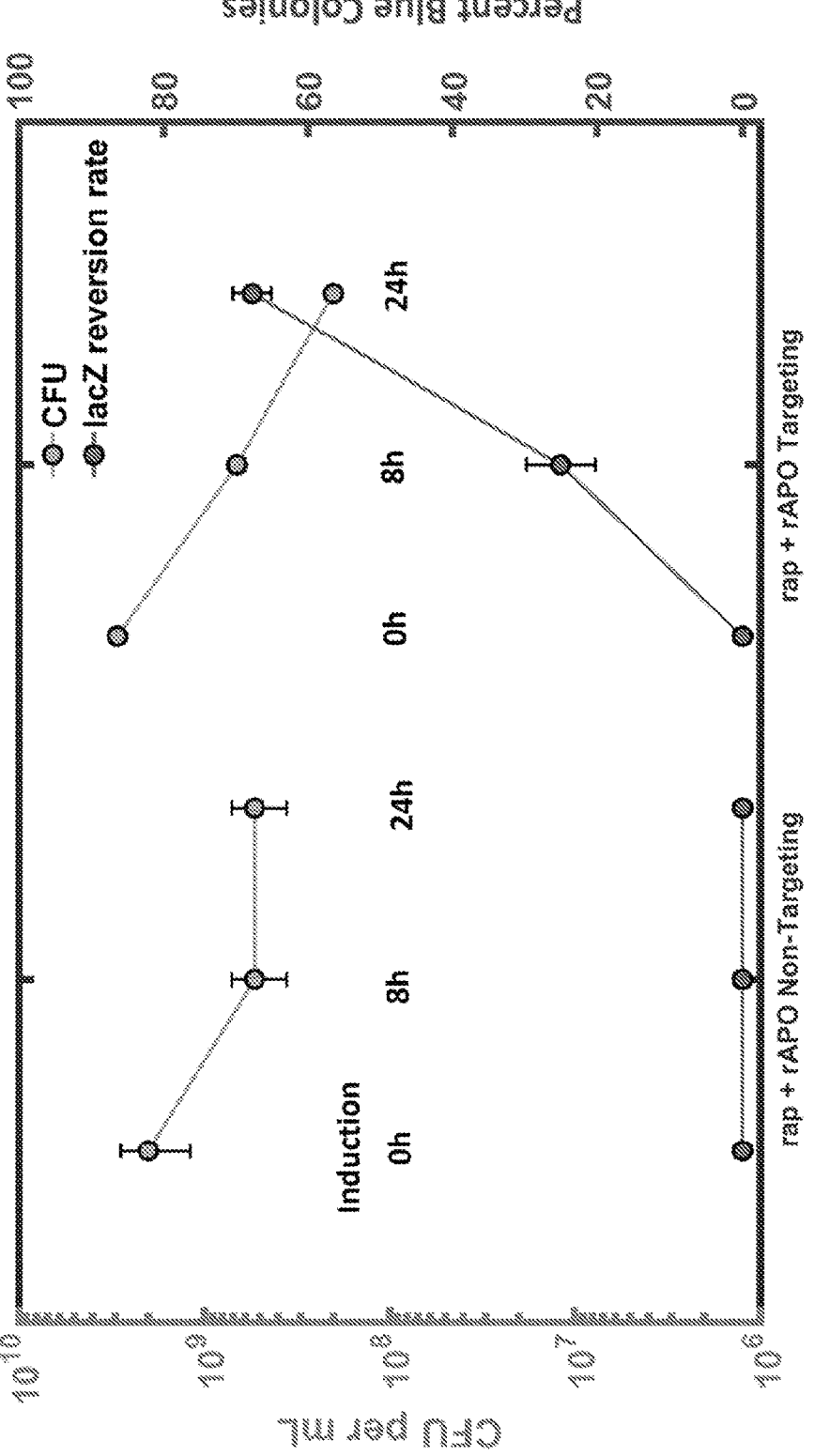
FIG. 8 includes representative results of experiments demonstrating the enhancement of gap editor genome editing activity via co-expression of Rap resolvase.
Figure 9:
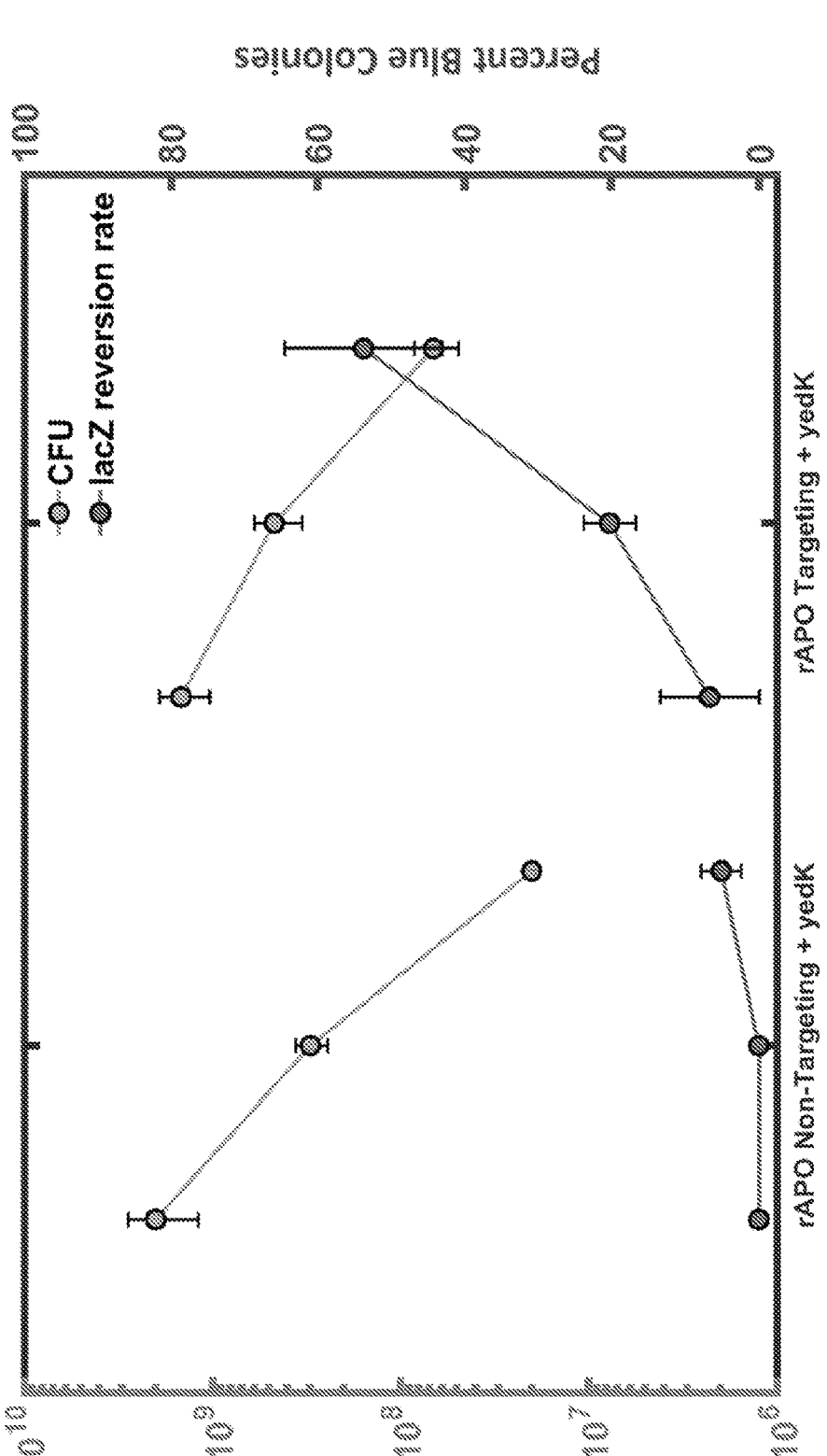
FIG. 9 includes representative results of experiments demonstrating that YedK co-expression increased gap editor-dependent genome editing and gap editor-independent editing.
Figure 10:
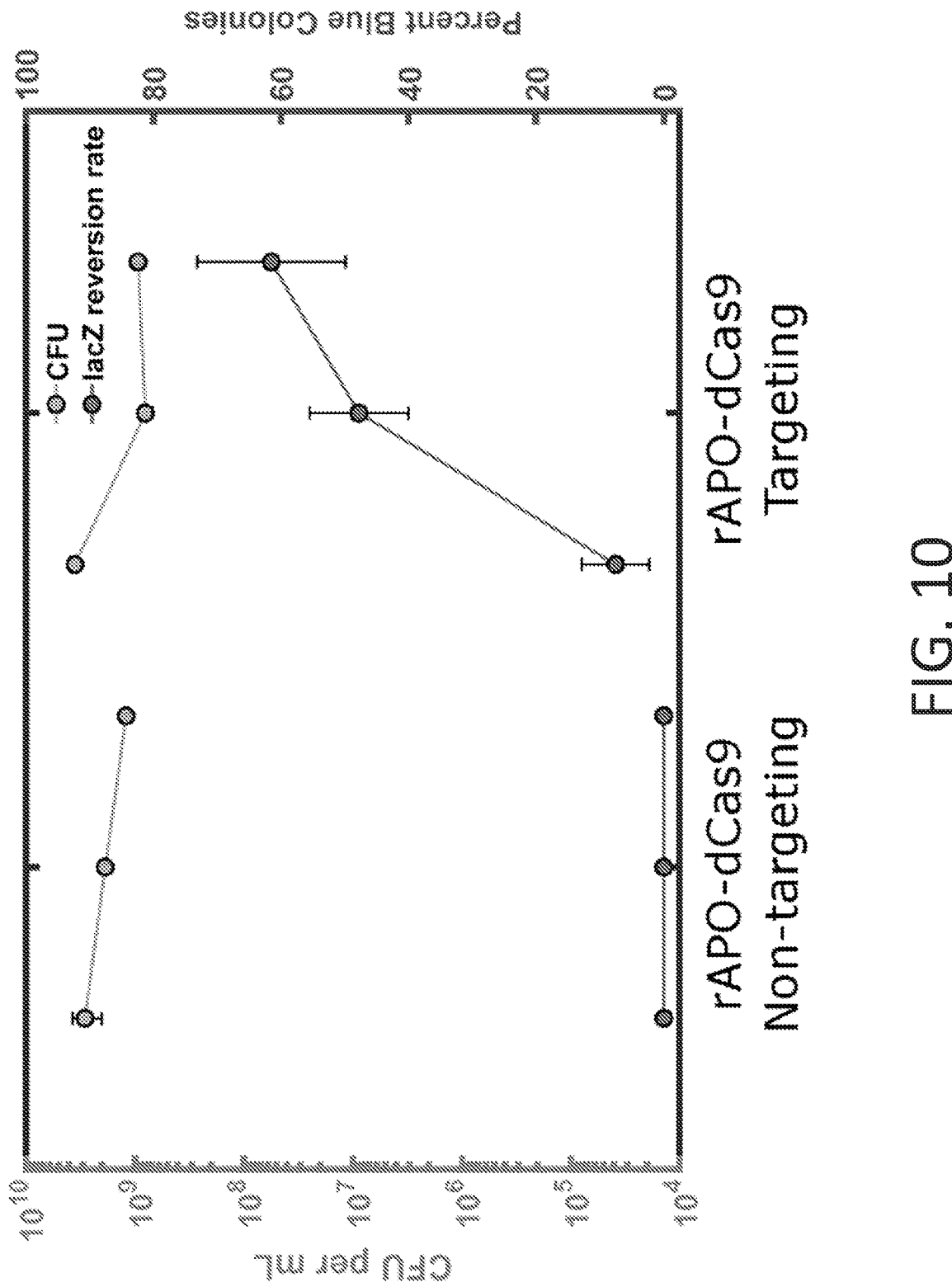
FIG. 10 includes representative results of experiments demonstrating elevated targeted gap repair activity in a recJ-deletion strain.
Figure 11:
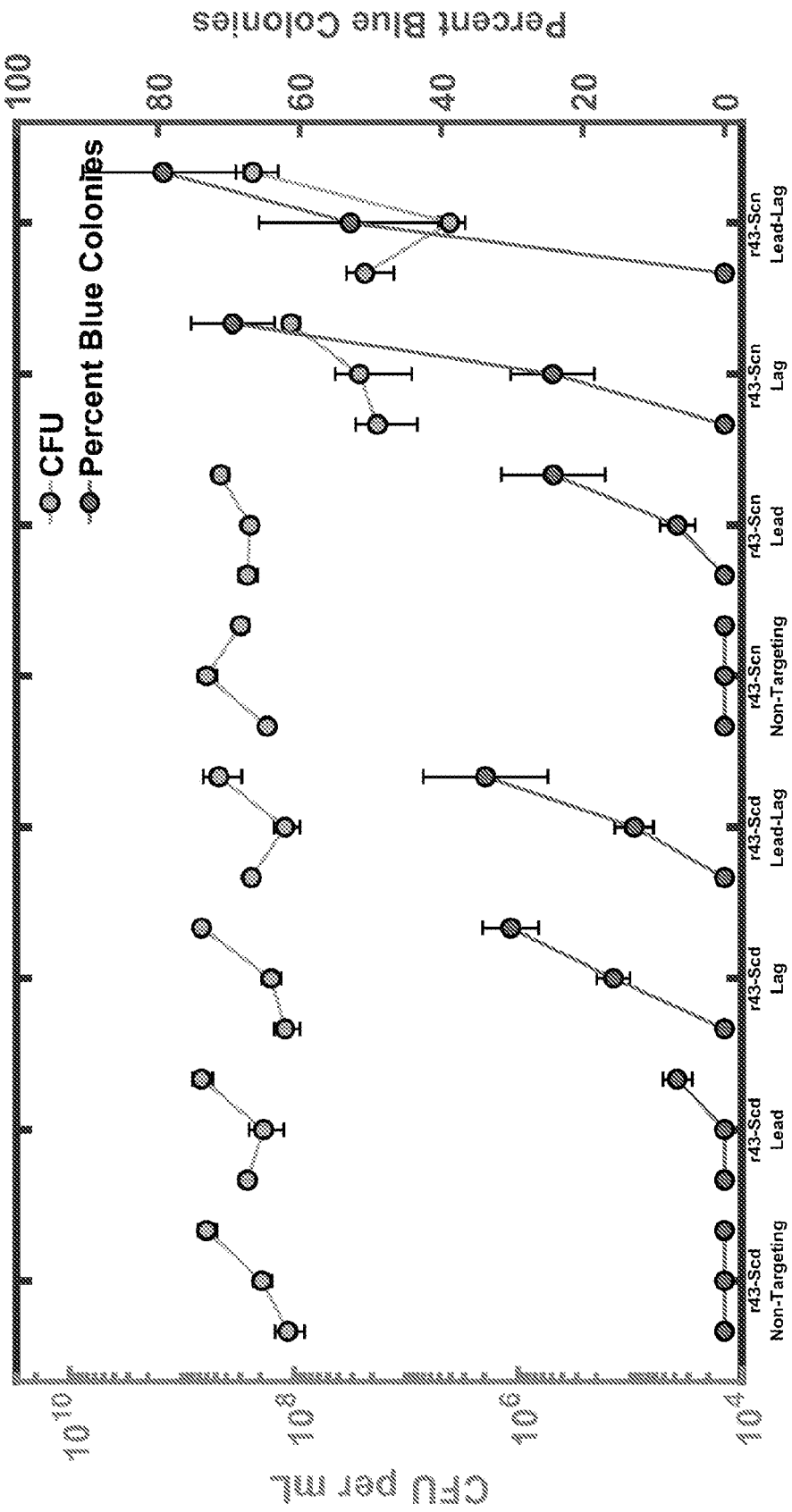
FIG. 11 includes representative results of experiments demonstrating that introducing nicking activity to a gap editor increased the rate of genome editing activity at a lacZ gene.
Figure 12:
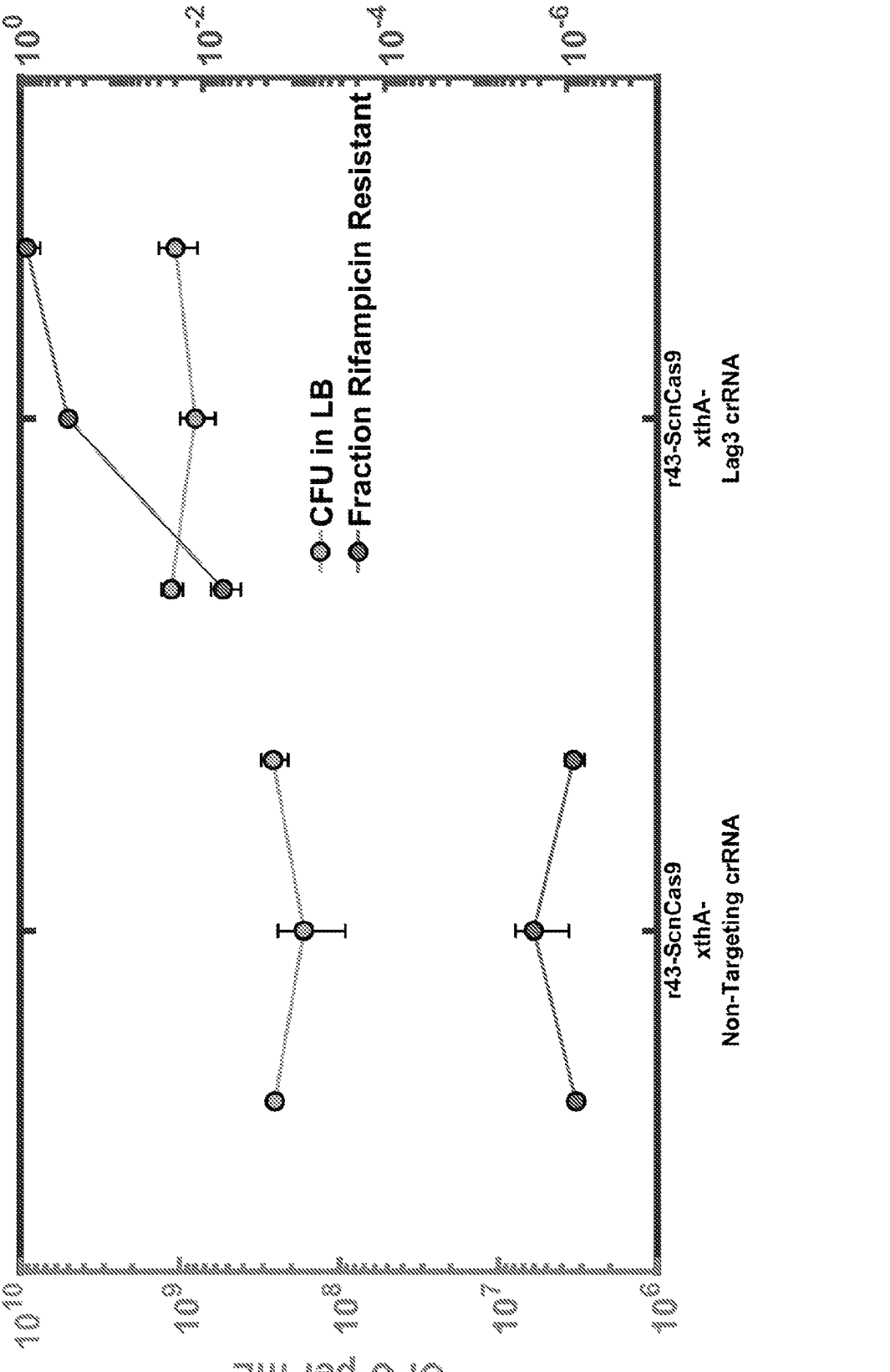
FIG. 12 includes representative results of experiments demonstrating that introducing nicking activity to a gap editor increased the rate of genome editing activity at a rpoB gene.
Figure 13:
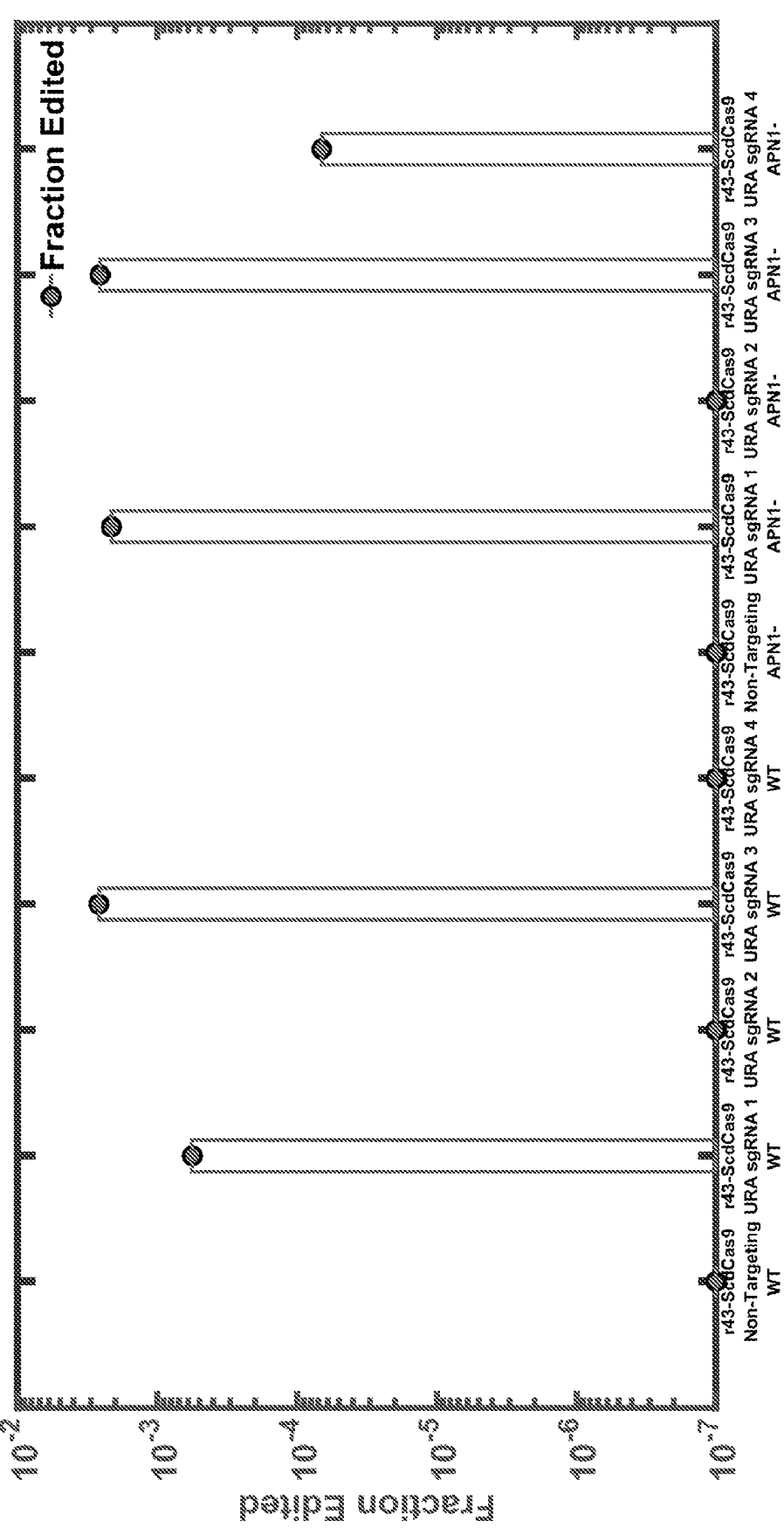
FIG. 13 includes representative results of experiments demonstrating that gap editor complexes can effectuate targeted genome editing in eukaryotes.

| DNA or Strain Name | Composition | Function | FIG.: |
|---|---|---|---|
| SPC673 | rAPO-dCas9 LacI araC pAra Lac CmR p15a | DNA Recognition and DNA Modifying, nuclease-free gap editor with SpCas9 | FIGS. 2, 5, 7 |
| SPC1243 | lacZ lead v1 lag v4 repair template kanR CloDF13 | donor nucleic acid template for lacZ repair | FIG. 5 |
| SPC1205 | lead 1st v1 single lesion Cas9 crRNA L2/RE AmpR ColE1 | single gRNA, leading strand targeting lacZ | FIG. 5 |
| SPC1207 | lag 1st v4 single lesion Cas9 crRNA L2/RE AmpR ColE1 | single gRNA, lagging strand targeting lacZ | FIG. 5 |
| SPC1322 | non-targeting crRNA and lead1 lag5 lacZ reversion template AmpR ColE1 | gRNA control and donor nucleic acid for lacZ repair | FIGS. 2, 3, 5-11, 15 |
| SPC1323 | lead1 lag5 crRNA and lead1 lag5 lacZ reversion template AmpR ColE1 | dual gRNA and donor nucleic acid for lacZ repair | FIGS. 2, 3, 5-9, 11, 15 |
| SPC1367 | rap pTET tetR kanR sc101 | accessory factor | FIGS. 2, 8 |
| SPC1377 | yedK pTET tetR kanR sc101 | accessory factor | FIGS. 9 |
| SPC1195 | MG1655 araF__pCON ΔaraBAD ΔxthA lacZ__sg705- | *E. coli* for genome editing | FIGS. 2-9, 11, 12 14, 15 |
| SPC1877 | r43__1-ScdCas9 pBAD araC CmR p15a | DNA recognition and modifying, nuclease-free gap editor with ScCas9 | FIG. 11 |
| SPC1882 | r43__1-ScnCas9 pBAD araC CmR p15a | DNA recognition and modifying, target strand nicking gap editor with ScCas9 | FIG. 11, 12 |
| SPC1534 | spnCas9 H840A pBAD CmR p15a | SpCas9 nickase control for comparison with gap editors | FIG. 3 |
| SPC1440 | lead1 crRNA and lead1 lag5 lacZ reversion template AmpR ColE1 | Single gRNA leading strand targeting lacZ, with lacZ repair donor template | FIG. 3, FIG. 11 |
| SPC1441 | lag5 crRNA and lead1 lag5 lacZ reversion template AmpR ColE1 | Single gRNA lagging strand targeting lacZ, with lacZ repair donor template | FIG. 3, FIG. 11 |
| SPC1426 | lead4 lacZ crRNA AmpR ColE1 | Single gRNA leading strand targeting lacZ, with lacZ repair donor template | FIG. 3 |
| SPC1427 | lag7 lacZ crRNA AmpR ColE1 | Single gRNA lagging strand targeting lacZ, with lacZ repair donor template | FIG. 3 |
| SPC1429 | lead4 then lag7 lacZ GE crRNA AmpR ColE1 | Dual gRNA targeting lacZ, with lacZ repair donor template | FIG. 3 |
| SPC1568 | Cas9 rpoB lag3 crRNA w/ tracr leader rpoB res RT L2/RE AmpR ColE1 | crRNA targeting rpoB and donor template mutating rpoB to confer rifampicin resistance | FIGS. 4, 12 |
| SPC1569 | rpoB lead1 then lag3 crRNA w/tracr leader rpoB res RT L2/RE AmpR ColE1 | Dual targeting crRNA targeting rpoB and donor template mutating rpoB to confer rifampicin resistance | FIG. 4 |
| SPC1565 | Non-Targeting crRNA rpoB res mut RT AmpR ColE1 | Non-targeting crRNA and rpoB donor template mutating rpoB to confer rifampicin resistance | FIGS. 4, 12 |
| SPC1402 | MG1655 araF__pCON ΔaraBAD ΔxthA ΔrecF lacZ__sg705- | *E. coli* without recF for genome editing | FIG. 6 |
| SPC1416 | MG1655 araF__pCON ΔaraBAD ΔxthA ΔrecJ lacZ__sg705- | *E. coli* without recJ for genome editing | FIG. 10 |
| SPC1437 | rAPO-dCas9 pBAD araC CmR p15a | DNA Recognition and DNA Modifying, nuclease-free gap editor with SpCas9 | FIGS. 3, 4 |
| SPC1438 | rAPO-dCas9-UGI pBAD araC CmR p15a | Deaminase and Uracil Glycosylase inhibitor fused to spdCas9 for investigating importance of abasic sites in editing | FIG. 7 |
| ISA662 | URA repair Template pSNR52 sgRNA (non-targeting) TRP1 2 micron, AmpR, ColE1 LS/R1 | Non-targeting control sgRNA with URA3 gene repair DNA donor template for targeted genome editing by a gap editor complex in yeast | FIG. 13 |
| ISA636 | URA repair Template pSNR52 sgRNA1 TRP1 2 micron, AmpR, ColE1 LS/R1 | sgRNA with URA3 gene repair DNA donor template for targeted genome editing by a gap editor complex in yeast | FIG. 13 |
| ISA637 | URA repair Template pSNR52 sgRNA2 TRP1 2 micron, AmpR, ColE1 LS/R1 | sgRNA with URA3 gene repair DNA donor template for targeted genome editing by a gap editor complex in yeast | FIG. 13 |
| ISA638 | URA repair Template pSNR52 sgRNA3 TRP1 2 micron, AmpR, ColE1 LS/R1 | sgRNA with URA3 gene repair DNA donor template for targeted genome editing by a gap editor complex in yeast | FIG. 13 |

TABLE 2-continued

Figure 14:
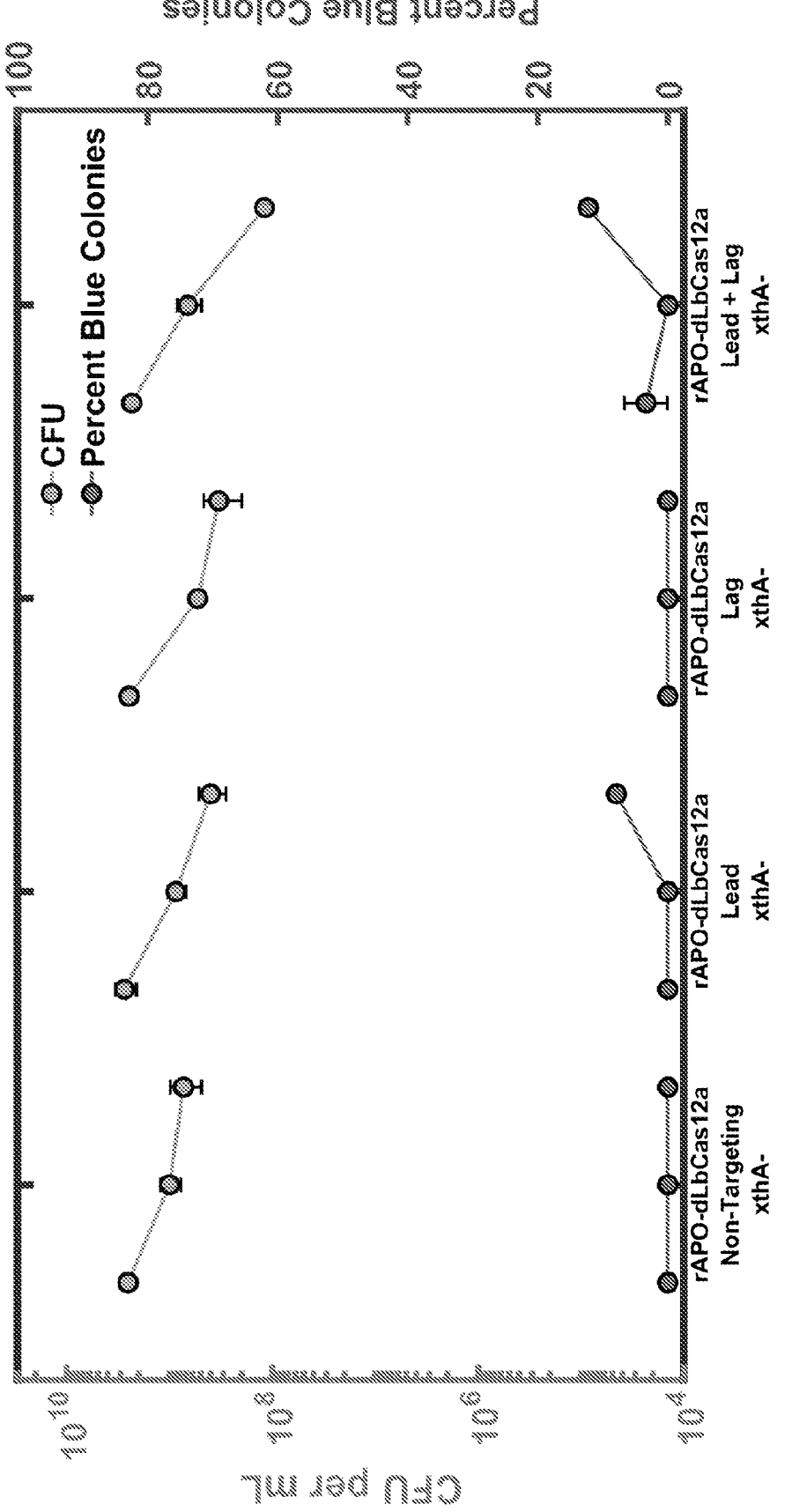
FIG. 14 includes representative results of experiments demonstrating that gap editor complexes can use DNA binding proteins other than Cas9 (e.g., Cas12a).
Figure 15:
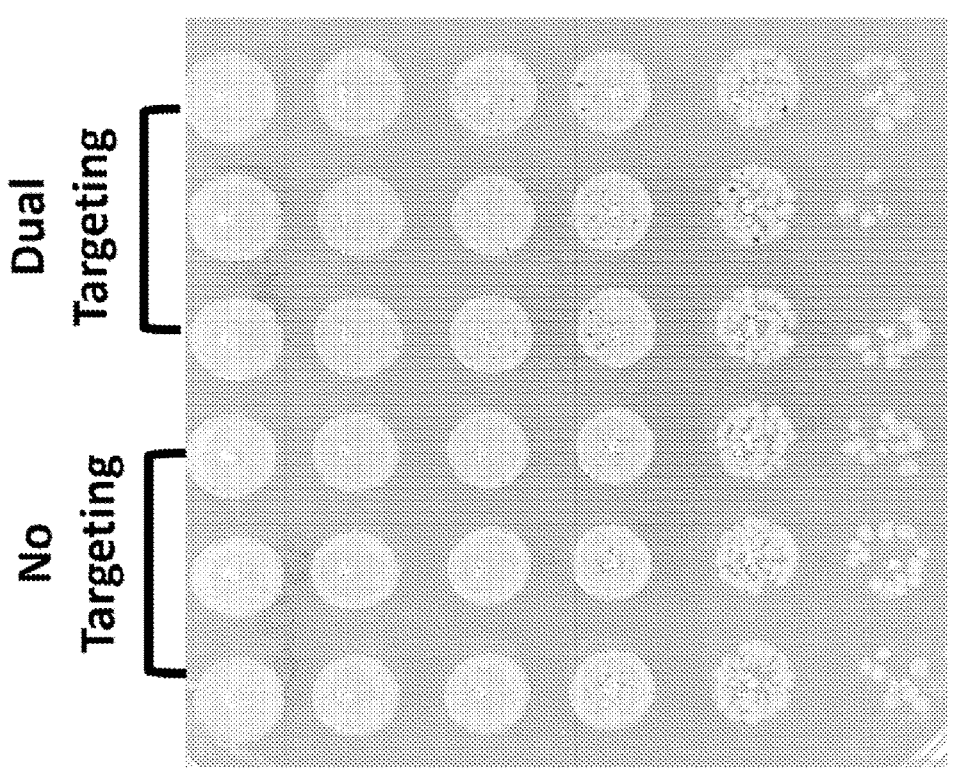
FIG. 15 includes representative results of experiments demonstrating detectable gap editing using a cytosine DNA glycosylase fused to dCas9 (SEQ ID NO: 2) in a lacZ gene repair assay.
Figure 15:
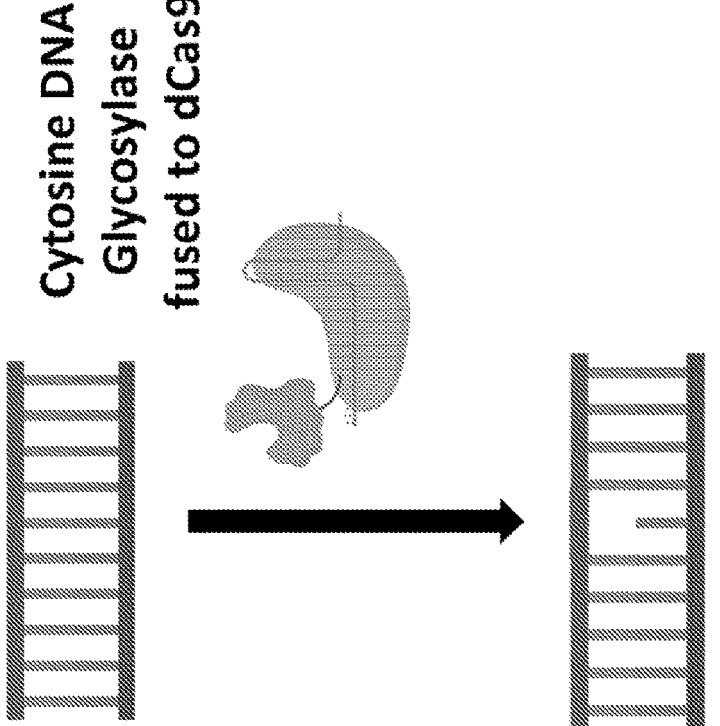

| DNA or Strain Name | Composition | Function | FIG.: |
|---|---|---|---|
| ISA639 | URA repair Template pSNR52 sgRNA4 TRP1 2 micron, AmpR, ColE1 LS/R1 | sgRNA with URA3 gene repair DNA donor template for targeted genome editing by a gap editor complex in yeast | FIG. 13 |
| ISA608 | BY4741 trp knockout URA3 Dbl Stop IS1 Integration | Yeast for testing genome editing using gap editor complex | FIG. 13 |
| ISA609 | BY4741 ΔAPN1 trp knockout URA3 Dbl Stop IS1 Integration | Yeast for testing genome editing using gap editor complex | FIG. 13 |
| SPC1590 | rAPO-dLbCas12a pBAD CmR p15a | Gap editor complex using CRISPR-Cas12a | FIG. 14 |
| SPC1613 | Non-Targeting crRNA LbCas12a lacZ RT AmpR ColE1 | Non-targeting control crRNA with lacZ gene repair DNA donor template for targeted genome editing by a gap editor complex using Cas12a | FIG. 14 |
| SPC1614 | lacZ lead1 crRNA LbCas12a lacZ RT AmpR ColE1 | Single lacZ targeting crRNA with lacZ gene repair DNA donor template for targeted genome editing by a gap editor complex using Cas12a | FIG. 14 |
| SPC1615 | lacZ lag1 crRNA LbCas12a lacZ RT AmpR ColE1 | Single lacZ targeting crRNA with lacZ gene repair DNA donor template for targeted genome editing by a gap editor complex using Cas12a | FIG. 14 |
| SPC1616 | lacZ lead1 lag1 dual crRNA LbCas12a lacZ RT AmpR ColE1 | Dual lacZ targeting crRNAs with lacZ gene repair DNA donor template for targeted genome editing by a gap editor complex using Cas12a | FIG. 14 |
| SPC1419 | CDG-dCas9 3k TIR LacI araC pAra Lac CmR p15a | Gap editor complex using a glycosylase for a DNA modification domain, fused to a nuclease inactive Cas9 | FIG. 15 |

5. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Experiments were conducted using *Escherichia coli* in which a chromosomal gene (lacZ) encoding an enzyme capable of producing a blue pigment was initially inactive due to two point mutations that introduce a premature stop codon. A plasmid-encoded DNA repair template was introduced into the cells, which included the sequence for the corrected lacZ gene. If the repair template successfully recombines with the chromosomal DNA, the gene will become active and the cells will turn blue. If unsuccessful, the cells will remain white.

As shown in FIGS. 2A-2C, experimental results demonstrated that gap editor targeting leads to efficient and extensive genome editing after 24 hours of induction. To direct editing and gene repair, plasmids were provided, which express a rAPOBEC1-dCas9 gap editor, and guide RNAs that direct the gap editor towards the gene to be repaired (FIG. 2A). In the absence of gap-editor targeting, genome editing rates are minimal (FIG. 2B; left three rows). Homologous recombination rates in bacteria tend to be low, so this not unexpected. Upon directing the gap editor to the target site, genome editing became significant and extensive (FIG. 2B; right three rows). Colonies were sequenced, which verified that lacZ was repaired with the desired sequence (FIG. 2C).

Gap editing was compared against one of the current best options for low toxicity genome editing, CRISPR-Cas9 nicking. The rate of lacZ gene repair by the gap editors far outstripped nickase editing at all tested targets (FIG. 3). There was also no evidence of lost viability (FIGS. 2 and 3), whereas genome targeting with fully nuclease-active Cas9 has been previously shown to be heavily cytotoxic. These data also demonstrate that gap editing can function on either the leading or lagging strand of replication, and only a single target is necessary for efficient editing. However, two targets increased the rate of editing (FIG. 3).

Figures 4A, 4B:
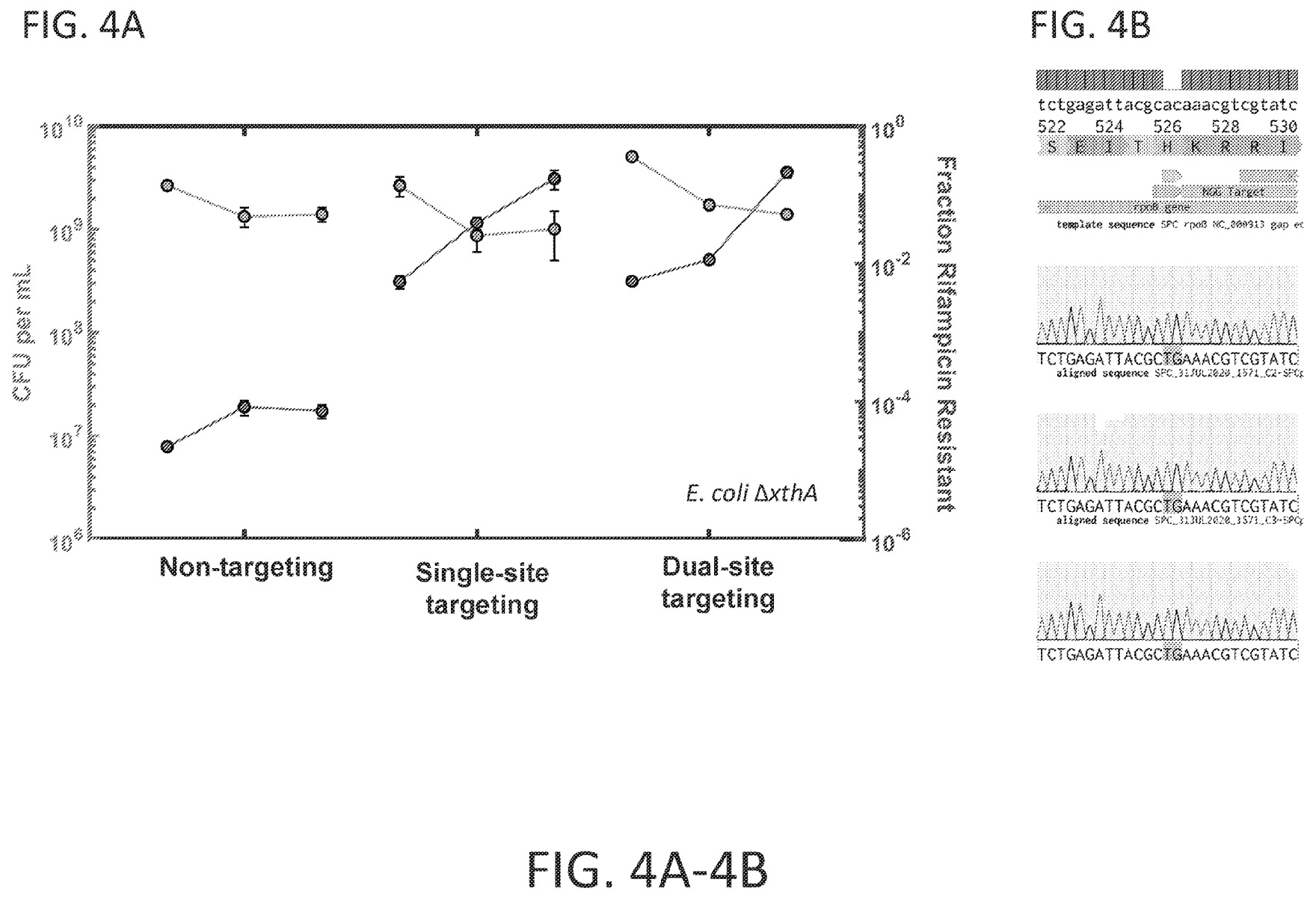

To demonstrate that gap editors could modify a diverse range of sequences, gap editors were targeted to the rpoB gene in *E. coli* to mutate amino acid H526, generating a mutant protein which confers resistance to the antibiotic rifampicin. In the absence of targeting, gap editors and the repair template produced minimal editing, but upon targeting rpoB, the rate of genome editing increased by more than 10,000 fold (FIG. 4A). Sanger sequencing was used to confirm the identity of the desired mutation (FIG. 4B).

Targeted gene repair of lacZ, with minimal cytotoxicity and using either one or two targets, was confirmed (FIG. 5A-5B).

To help validate the proposed mechanism through which gap editors function, gap editor directed recombination was tested with a lacZ gene repair assay in a recF-deficient strain. RecF facilitates loading of RecA to ssDNA-dsDNA junctions at replication forks disrupted by DNA lesions (e.g. abasic sites), for homologous recombination and repair. As shown in FIG. 6, no evidence of lacZ gene repair was seen with or without DNA targeting by the gap editor complex in the absence of recF.

Further experiments were conducted to investigate whether a typical base editor, which include a cytidine deaminase domain as well as a uracil glycosylase inhibitory domain (UGI), could also drive recombination. The expectation was that the base editor would not drive recombination, as UGI would block the excision of the modified uracil, thereby preventing formation of the abasic site. Using the same lacZ gene repair assay with the base editor BE3, results demonstrate that the base editor completely inhibited repair above a non-targeting control (FIG. 7).

Example 2

In an effort to both better understand gap editor mechanisms and to improve genome editing rates, experiments were conducted to test gap editors with a variety of cofactors. Experiments focused on the following: stabilizing abasic sites to increase the likelihood of two abasic sites being introduced simultaneously; increasing the rate of abasic site production; and accelerating the homologous-recombination process.

Homologous recombination involves a number of proteins acting in concert to re-arrange and copy DNA. Phage proteins have served as a reservoir of cofactors to enhance recombination and genome editing. However, using recombinases did not improve gap editor activity in this context. In the present disclosure, a Rap resolvase encoded by lambda phage was identified as a candidate gap editor accessory factor that could enhance recombination in genome editing technologies. Co-expression of Rap was tested along with the gap editors in the same experiment as previously described. Co-expression of Rap substantially improved gap editor-dependent editing, as shown in FIG. 8.

Scientific understanding of DNA repair is still evolving, and a recently described DNA repair protein, YedK, may have a significant impact on gap editor functionality. Evidence suggests that this protein, and its eukaryotic equivalent, HMCES, binds to abasic sites, protecting them for DNA repair by an as yet unclear mechanism. As shown in FIG. 9, co-expression of YedK along with gap editors of the present disclosure increased editing rates.

After introduction of a DNA gap, various different factors are involved in the digestion of DNA to facilitate recombination. In E. coli, two of these factors include the helicase, RecJ, and the helicase, RecQ. Inhibiting these factors could impact editing. Using the lacZ repair assay, gap editing activity in a recJ-deletion strain was tested. It was found that this strain exhibited elevated targeted gap repair activity, likely due to preventing excessive digestions that would lead to a mismatch between repair template length and the size of the DNA gap to repair (FIG. 10).

Example 3

Repair of DNA lesions by the sister chromatid is counterproductive for genome editing. In order to improve the efficiency of gap editing, methods of disrupting the sister chromatid strand, were explored (excluding targeting with a second gap editor). Experiments were conducted to test the hypothesis that by nicking the DNA strand opposite the induced DNA gap, repair of the gap by the endogenous sister chromatid could be reduced or prevented. As demonstrated in FIG. 11 (right side), the use of target strand nickase activity of the gap editor yielded a significant increase in genome editing. The increase occurred whether targeting the leading strand, lagging strand, or both strands in relation to DNA replication.

To confirm the increased rate of genome editing by a gap editor with nickase activity, a single target at the rpoB gene was tested with a repair template conferring a mutation for antibiotic resistance. As demonstrated in FIG. 12, after 24 hours of induction, the rate of targeted genome editing approached 100%, and site-specific targeting of the gap editor demonstrated a more than 1,000,000-fold increase in rates of templated homologous recombination at the rpoB gene.

Example 4

In order to demonstrate that gap editing could function in eukaryotic cells, a gap editing construct for yeast expression was generated, which is induced by the addition of galactose. A nuclease-free rAPOBEC1-dCas9 gap editor, a targeting or non-targeting sgRNA, and a plasmid-borne repair template were transformed into yeast. The repair template encoded a DNA sequence to repair a defunct URA3 gene housed in the Saccaromyces cerevisiae genome. After induction of the gap editor for 24 hours, approximately a 700 to 20,000 fold increase in genome editing over the non-target control was observed for some targets (FIG. 13). Thus, gap editors function in multiple organisms, including eukaryotes. Knockout of the endogenous AP endonuclease, APN1, conferred an increase in rates of genome editing (FIG. 13, right side). The homologous recombination machinery in yeast has close homologs in higher eukaryotes, including mammals and plants; therefore, gap editing will likely function in higher eukaryotes as well.

Example 5

To show that alternative DNA binding domains besides Cas9 could be used, the rAPOBEC1 deaminase was fused to the nuclease inactive dLbCas12a enzyme. This gap editor was tested by expressing a crRNA targeting a defunct lacZ gene on the E. coli genome, and a repair template encoding a sequence to repair lacZ to its functional state. As demonstrated in FIG. 14, inducing the gap editor for 24 hours produced measurable levels of genome editing in the lacZ targeting condition and no editing in the non-targeting control.

Example 6

To demonstrate an alternative DNA modification domain for gap editing, a cytosine DNA glycosylase fused to dCas9 (SEQ ID NO: 2) was utilized in a lacZ gene repair assay. In this format, it was expected that cytosine could be directly removed from the DNA backbone, as opposed to the deaminase system, which first converts cytosine to uracil, and then uracil is excised by uracil DNA glycosylase. As shown in FIG. 15, after inducing the glycosylase-dCas9 for lacZ gene repair, gap editing was detectable, but at a much lower frequency than for the deaminase fusion.

Sequences of exemplary gap editors as described herein are provided in the sequence listing, and include the following: rAPOBEC1-dCas9 deaminase gap editor (SEQ ID NO: 1); Cytosine DNA glycosylase-dCas9 (SEQ ID NO: 2);

MAG1 glycosylase-dCas9 (SEQ ID NO: 3); hAAG glycosylase-dCas9 (SEQ ID NO: 4); SPC1590 rAPO-dLbCas12a pBAD CmR p15a (SEQ ID NO: 5); SPC1877 r43_1-ScdCas9 pBAD araC CmR p15a (SEQ ID NO: 6); and SPC1882 r43_1-ScnCas9 pBAD araC CmR p15a (SEQ ID NO: 7).

It is understood that the foregoing detailed description and accompanying examples are merely illustrative and are not to be taken as limitations upon the scope of the disclosure, which is defined solely by the appended claims and their equivalents.

All publications and patents mentioned in the above specification are herein incorporated by reference as if expressly set forth herein. Various changes and modifications to the disclosed embodiments will be apparent to those skilled in the art and may be made without departing from the spirit and scope thereof.

What is claimed is:

1. A composition for targeted editing of a nucleic acid, the composition comprising:
   a) a gap editor complex comprising a DNA-recognition domain and a DNA-modifying domain, wherein the gap editor complex induces formation of at least one abasic site in a target sequence of a double-stranded DNA molecule;
   b) at least one guide RNA molecule; and
   c) a donor nucleic acid template, wherein the presence of the donor nucleic acid template facilitates homology-directed recombination, and wherein the donor nucleic acid template or a fragment thereof is recombined into the double-stranded DNA molecule.

2. The composition of claim 1, wherein the DNA-recognition domain comprises at least one Cas protein or fragment thereof lacking deoxyribonuclease activity.

3. The composition of claim 1, wherein the DNA-recognition domain comprises a complex of Cas proteins lacking deoxyribonuclease activity.

4. The composition of claim 2 or claim 3, wherein the Cas protein or Cas proteinthe complex of Cas proteins comprises a Type I Cascade, a Type II Cas9, a Type IV effector module, or a Type V Cas 12.

5. The composition of claim 1, wherein the DNA-modifying domain catalyzes formation of the at least one abasic site in the DNA target sequence.

6. The composition of claim 1, wherein the DNA-recognition domain comprises a Cas protein or fragment thereof having nickase activity.

7. The composition of claim 1, wherein the DNA-recognition domain and the DNA-modifying domain comprise a functional coupling.

8. The composition of claim 7, wherein the DNA-recognition domain comprises a deoxyribonuclease-inactivated Cas9.

9. The composition of claim 7, wherein the functional coupling comprises polypeptide fusions, peptide tags, peptide linkers, or RNA tags.

10. The composition of claim 1, wherein the DNA-modifying domain comprises glycosylase activity, deaminase activity, oxidase activity, nucleosidase activity, hydroxylase, hydrolase activity, and combinations thereof.

11. The composition of claim 10, wherein the DNA-modifying domain comprises a cytidine deaminase.

12. The composition of claim 1, wherein the at least one guide RNA comprises a handle sequence and a targeting sequence.

13. The composition of claim 12, wherein the targeting sequence in the at least one guide RNA is complementary to the DNA target sequence.

14. The composition of claim 1, wherein the composition comprises at least a first and a second guide RNA.

15. The composition of claim 14, wherein the first guide RNA is complementary to a first DNA target sequence and the second guide RNA is complementary to a second DNA target sequence.

16. The composition of claim 15, wherein the first and the second DNA target sequences are on opposite strands of a double-stranded DNA molecule.

17. The composition of claim 1, wherein the at least one abasic site is generated in the DNA strand complementary to the DNA target sequence.

18. The composition of claim 17, wherein the at least one abasic site is generated outside the DNA target sequence.

19. The composition of claim 1, wherein the gap editor complex induces formation of the at least one abasic site in the target sequence without inducing a double-stranded or single-stranded break.

20. The composition of claim 1, wherein the gap editor complex induces formation of at least two abasic sites in two distinct target sequences on opposite strands of the double-stranded DNA molecule without inducing a double-stranded or single-stranded break.

21. The composition of claim 1, wherein the composition further comprises at least one gap editor accessory factor.

22. The composition of claim 21, wherein the at least one gap editor accessory factor comprises a protein involved in DNA modification or repair.

23. The composition of claim 21, wherein the at least one gap editor accessory factor is recruited to the gap editor complex via interaction with the DNA-modifying domain, the DNA-recognition domain, and/or the at least one guide RNA.

24. The composition of claim 21, wherein the at least one gap editor accessory factor comprises Rap, lambda Beta, lambda Orf, RecT, a reverse transcriptase (MMLV, Ec86), a deactivated or dominant-negative abasic site exonuclease (Exonuclease III, APE1), YedK, HMCES, ExoI, PRIMPOL, RecJ, RECQ1, or Uracil DNA glycosylase.

25. The composition of claim 21, wherein the at least one gap editor accessory factor comprises a protein or RNA directing deoxyribonuclease activity, wherein the activity counter-selects against cells in which template-mediated editing of the DNA target has not occurred.

26. A method for targeted editing of a nucleic acid, the method comprising:
    introducing components (a), (b), and (c) of claim 1 into a cell; and
    assessing the cell for presence of a desired genetic altera-tion.

27. The method of claim 26, wherein the component (a) is introduced into the cell as a polypeptide(s), mRNA(s), and/or DNA expression construct(s).

28. The method of claim 26, wherein the method further comprises introducing at least one gap editor accessory factor into the cell as a polypeptide(s), mRNA(s), and/or DNA expression construct(s).

29. The method of claim 26, wherein the cell is a prokaryotic cell or a eukaryotic cell.

30. The method of claim 26, wherein the cell is a mammalian cell.

31. The method of claim 26, wherein the cell is a plant cell.

32. The method of claim 26, wherein the method leads to a reduced degree of indel formation, chromosomal inversions, or DNA duplications.

33. The method of claim 26, wherein cell viability is enhanced and/or cell toxicity is reduced.

34. The method of claim 26, wherein endogenous nuclease activity in the cell is attenuated.

35. A kit for targeted editing of a nucleic acid, the kit comprising:
    a) a gap editor complex comprising a DNA-recognition domain and a DNA-modifying domain, wherein the gap editor complex induces formation of at least one abasic site in a target sequence of a double-stranded DNA molecule;
    b) at least one guide RNA molecule; and
    c) a donor nucleic acid template, wherein the presence of the donor nucleic acid template facilitates homology-directed recombination, and wherein the donor nucleic acid template or a fragment thereof is recombined into the double-stranded DNA molecule.

36. A system for targeted editing of a nucleic acid, the system comprising:
    a) a gap editor complex comprising a DNA-recognition domain and a DNA-modifying domain, wherein the gap editor complex induces formation of at least one abasic site in a target sequence of a double-stranded DNA molecule;
    b) at least one guide RNA molecule; and
    c) a donor nucleic acid template, wherein the presence of the donor nucleic acid template facilitates homology-directed recombination, and wherein the donor nucleic acid template or a fragment thereof is recombined into the double-stranded DNA molecule.

37. The system of claim 36, wherein the system further comprises at least one gap editor accessory factor.

38. The method of claim 35 or claim 36, wherein the gap editor complex induces formation of that at least one abasic site in the target sequence without inducing a double-stranded or single-stranded break.

* * * * *